US012622891B2

(12) United States Patent
Nakata et al.

(10) Patent No.: US 12,622,891 B2
(45) Date of Patent: May 12, 2026

(54) AMP-ACTIVATED PROTEIN KINASE ACTIVATOR

(71) Applicant: KYOTO PHARMACEUTICAL UNIVERSITY, Kyoto (JP)

(72) Inventors: Susumu Nakata, Kyoto (JP); Naoto Kojima, Kyoto (JP)

(73) Assignee: KYOTO PHARMACEUTICAL UNIVERSITY, Kyoto (JP)

( * ) Notice: Subject to any disclaimer, the term of this patent is extended or adjusted under 35 U.S.C. 154(b) by 371 days.

(21) Appl. No.: 18/566,730

(22) PCT Filed: Jun. 3, 2022

(86) PCT No.: PCT/JP2022/023390
§ 371 (c)(1),
(2) Date: Dec. 4, 2023

(87) PCT Pub. No.: WO2022/255499
PCT Pub. Date: Dec. 8, 2022

(65) Prior Publication Data

US 2024/0277657 A1 Aug. 22, 2024

(30) Foreign Application Priority Data

Jun. 4, 2021 (JP) ................................ 2021-094481

(51) Int. Cl.
*A61K 31/381* (2006.01)
*A61K 31/415* (2006.01)
(Continued)

(52) U.S. Cl.
CPC .......... *A61K 31/381* (2013.01); *A61K 31/415* (2013.01); *A61P 35/00* (2018.01); *C07D 231/14* (2013.01); *C07D 333/38* (2013.01)

(58) Field of Classification Search
CPC .. A61K 31/381; A61K 31/415; C07D 231/14; C07D 333/38
See application file for complete search history.

(56) References Cited

U.S. PATENT DOCUMENTS 7,071,219 B2 7/2006 Fertig et al.
7,501,451 B2 3/2009 Fertig et al.
(Continued)

FOREIGN PATENT DOCUMENTS

JP 2006-516553 A 7/2006
JP 2007-510626 A 4/2007
(Continued)

OTHER PUBLICATIONS

Pilkington-Miksa, et al., "Design, synthesis, and biological evaluation of novel cRGD-Paclitaxel conjugates for integrin-assisted drug delivery", Bioconjugate Chemistry, vol. 23, No. 8, pp. 1610-1622 (2012).

(Continued)

*Primary Examiner* — Brandon J Fetterolf
(74) *Attorney, Agent, or Firm* — MARSHALL, GERSTEIN & BORUN LLP

(57) ABSTRACT

The present invention aims to provide a novel AMP-activated protein kinase activator.
The present invention relates to a compound represented by the formula (I):

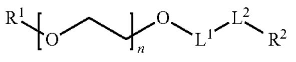

(I)

wherein each symbol is as described in the specification, or a salt thereof, or a hydrate thereof. In addition, the present
(Continued)

Proliferation suppressive action on murine glioblastoma stem cells

*, $p<0.05$, Student's T-test, (vs control)

invention relates to an AMP-activated protein kinase activator containing the aforementioned compound, and a medicament containing the aforementioned compound for the prophylaxis and/or treatment of cancer.

11 Claims, 11 Drawing Sheets

(51) Int. Cl.

| | |
|---|---|
| ***A61P 35/00*** | (2006.01) |
| ***C07D 231/14*** | (2006.01) |
| ***C07D 333/38*** | (2006.01) |

(56) References Cited

U.S. PATENT DOCUMENTS

| | | | | |
|---|---|---|---|---|
| 7,579,349 | B2 | 8/2009 | Nowak et al. | |
| 7,868,005 | B2 | 1/2011 | Rosenblum et al. | |
| 9,603,852 | B2 | 3/2017 | Schuster et al. | |
| 11,319,347 | B2 | 5/2022 | Inoue et al. | |
| 2004/0162317 | A1 | 8/2004 | Fertig et al. | |
| 2005/0090529 | A1 | 4/2005 | McAlpine et al. | |
| 2006/0089403 | A1 | 4/2006 | Fertig et al. | |
| 2007/0037888 | A1 | 2/2007 | Nowak et al. | |
| 2007/0054919 | A1 | 3/2007 | Rosenblum et al. | |
| 2008/0293696 | A1 | 11/2008 | Brennan et al. | |
| 2013/0345243 | A1 | 12/2013 | Bouillot et al. | |
| 2016/0113933 | A1 | 4/2016 | Schuster et al. | |
| 2020/0040039 | A1 | 2/2020 | Inoue et al. | |
| 2020/0339742 | A1 * | 10/2020 | Martin ................. | C08G 61/126 |

FOREIGN PATENT DOCUMENTS

| | | | |
|---|---|---|---|
| JP | 2008-504285 | A | 2/2008 |
| JP | 2011-178728 | A | 9/2011 |
| JP | 2014-507453 | A | 3/2014 |
| JP | 2020-083811 | A | 6/2020 |
| WO | 2006/062224 | A1 | 6/2006 |
| WO | 2006/088921 | A2 | 8/2006 |
| WO | 2011/162267 | A1 | 12/2011 |
| WO | 2014/069426 | A1 | 5/2014 |
| WO | 2014/204895 | A1 | 12/2014 |
| WO | 2018/174078 | A1 | 9/2018 |

OTHER PUBLICATIONS

Extended European Search Report dated May 14, 2025 in European Patent Application No. 22816244.2.

International Application No. PCT/JP2022/023390, International Preliminary Report on Patentability, mailed May 29, 2023.

Kim et al., AMPK activators: mechanisms of action and physiological activities, Experim. Mol. Med., 48:e224 (2016).

Martin et al., An Elastomeric Poly(Thiophene-EDOT) Composite with a Dynamically Variable Permeability Towards Organic and Water Vapors, Adv. Func. Mat., 22(15):3116-3127 (2012).

Motoshima et al., AMPK and cell proliferation—AMPK as a therapeutic target for atherosclerosis and cancer, J. Physiol., 574(Pt 1):63-71 (2006).

O'Neiii, AMPK and Exercise: Glucose Uptake and Insulin Sensitivity, Diab. Metab. J., 7(1):1-21 (2013).

Ruderman et al., AMPK, insulin resistance, and the metabolic syndrome, J. Clin. Invest., 123(7):2764-2772 (2013).

* cited by examiner

[Fig. 1]
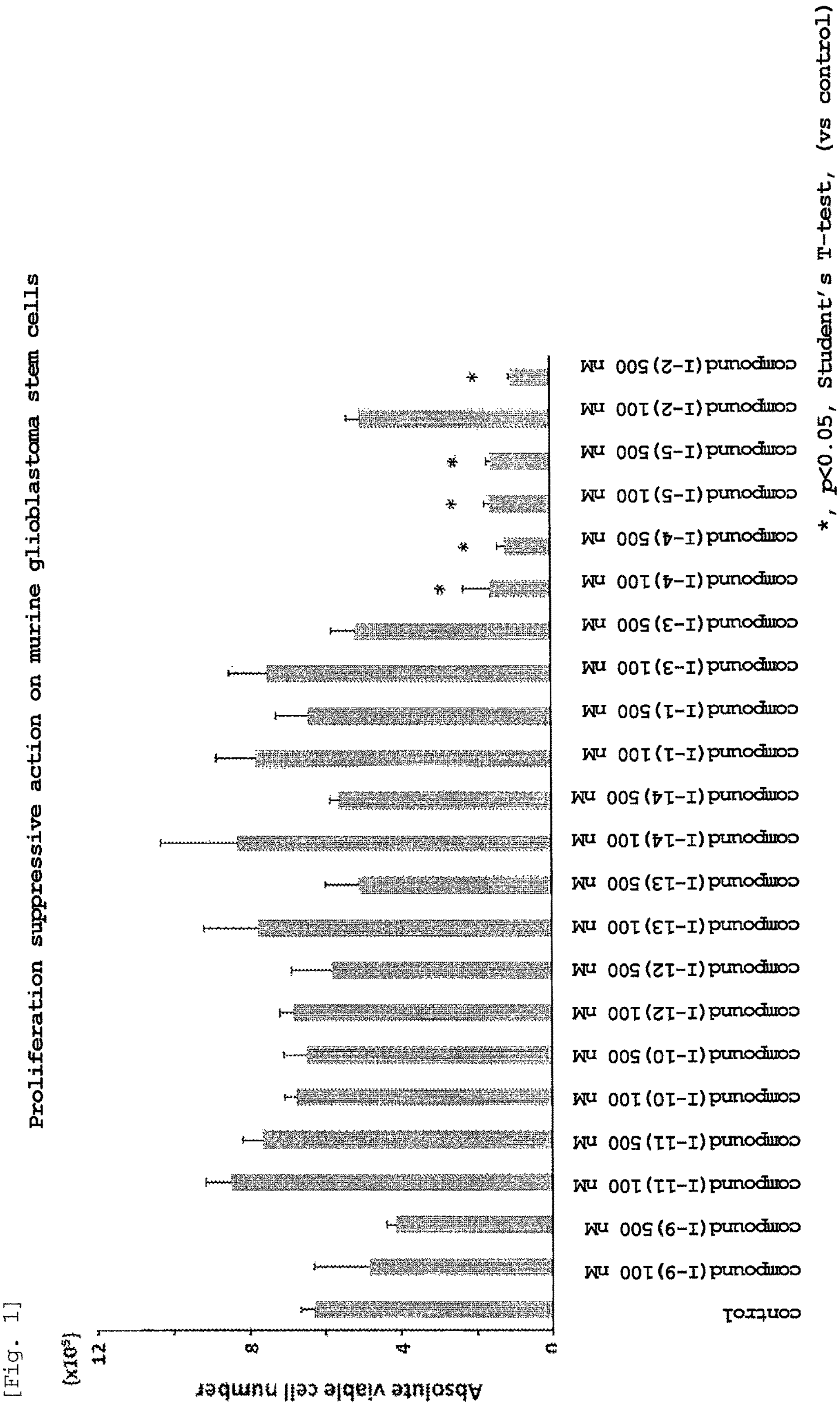

[Fig. 2]
Synergistic effect of alkylating agent temozolomide and compound (I-5) on human glioblastoma cell line U251
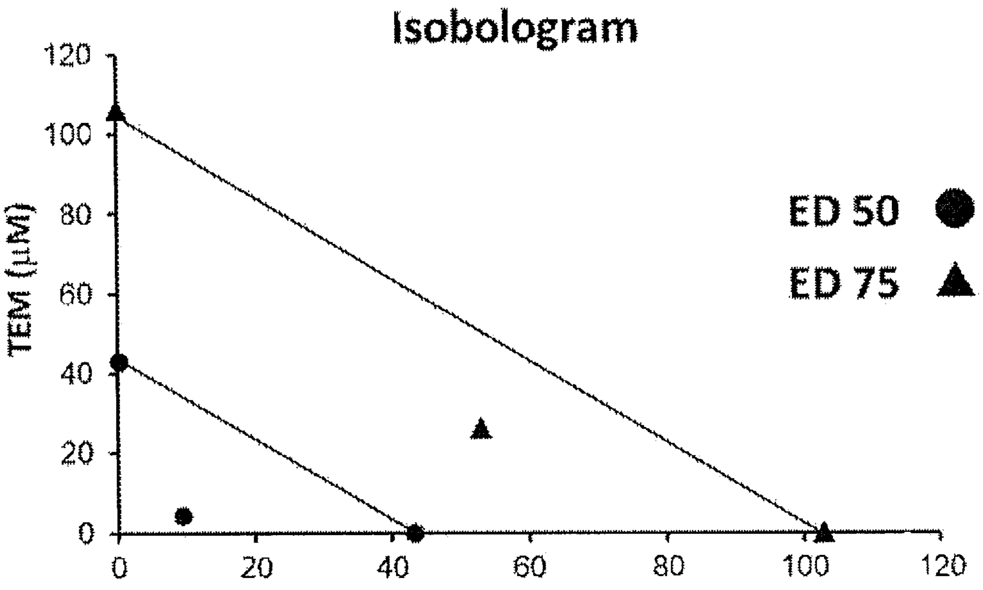
compound (I-5) (nM)
| |
|---|
| CI=0.325 at ED50 value |
| CI=0.765 at ED75 value |
| CI=0.415 for combined use of TEM 12.5 μM and compound (I-5) 25 nM |

[Fig. 3]
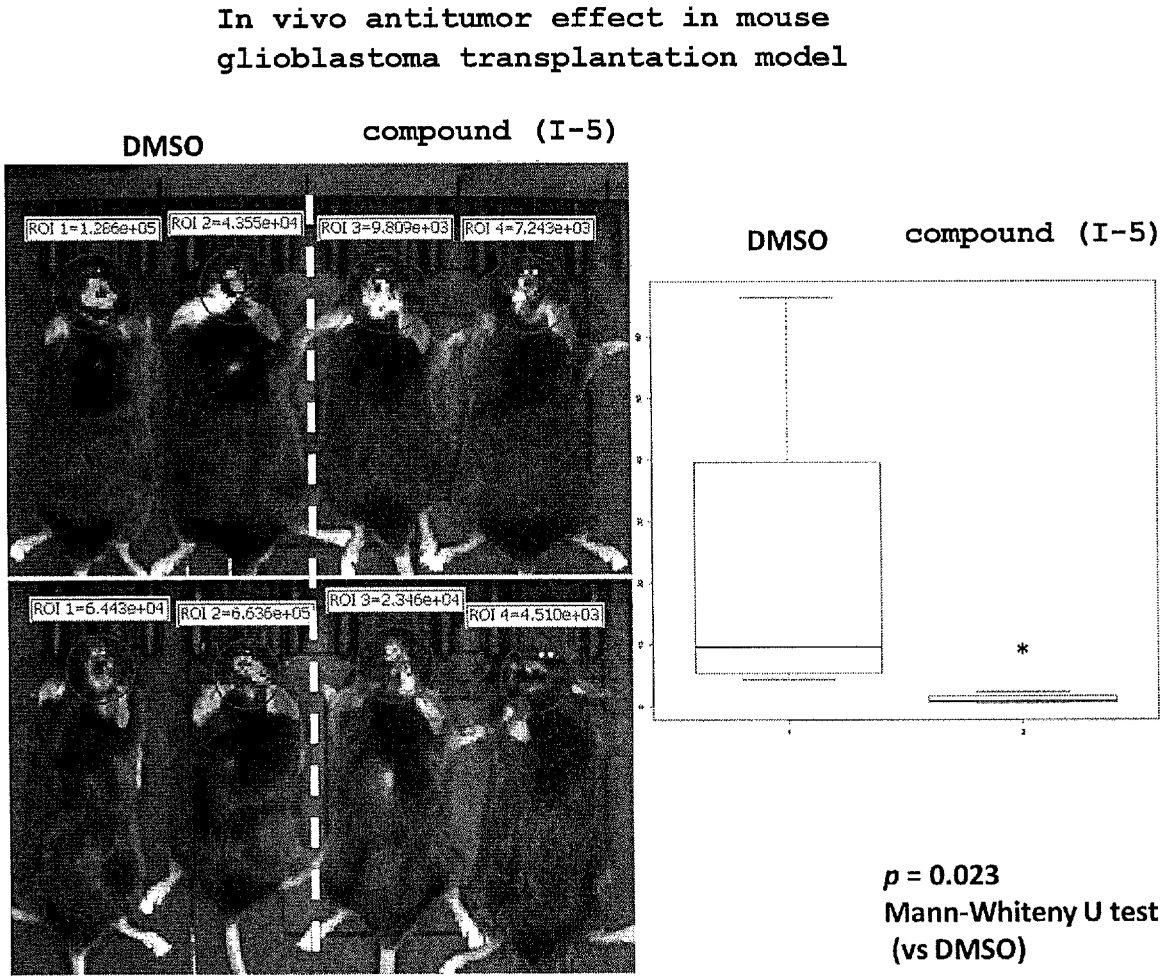

[Fig. 4]
Proliferation suppressive action on human colon cancer SW48 cells
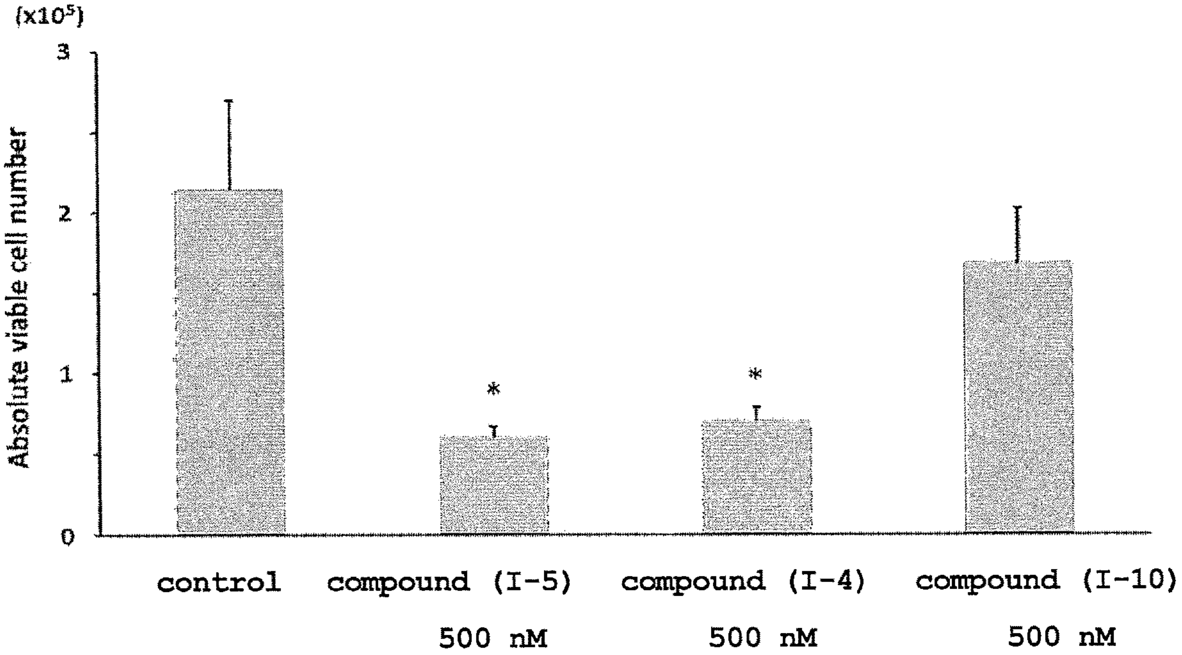
*, $p<0.05$, Student's T-test, (vs control)

[Fig. 5]
Increasing effect on AMP/ATP ratio in human colon cancer SW48 cells
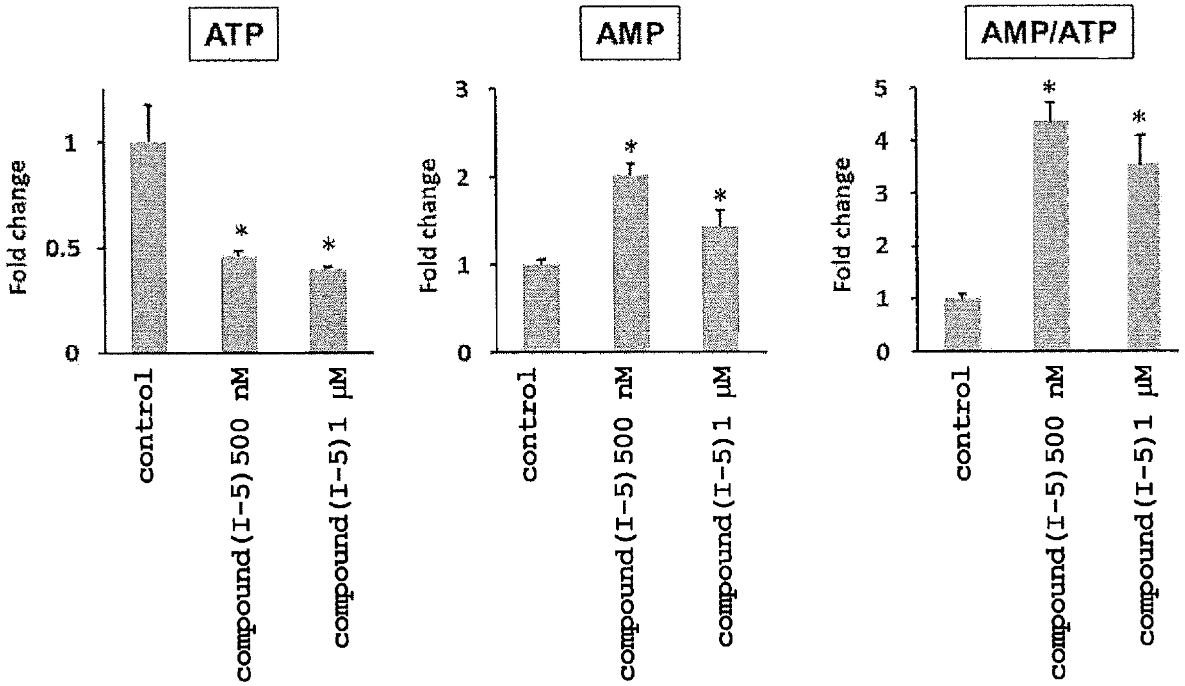
*, $p$<0.05, Student's T-test, (vs control)

[Fig. 6]
Activation of AMPK in human colon cancer SW48 cells
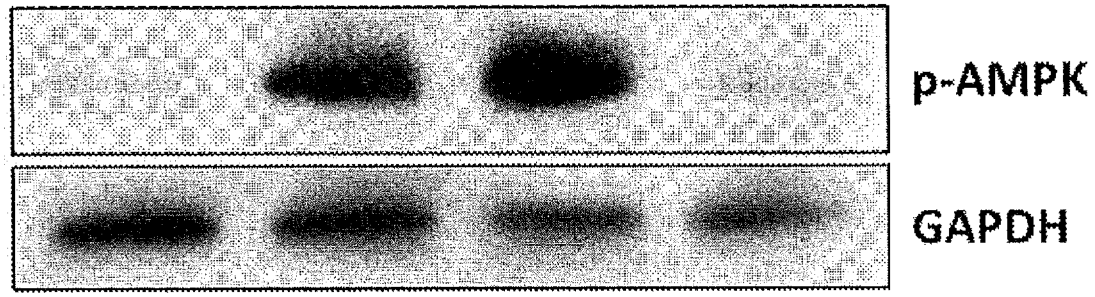

[Fig. 7]
(A)
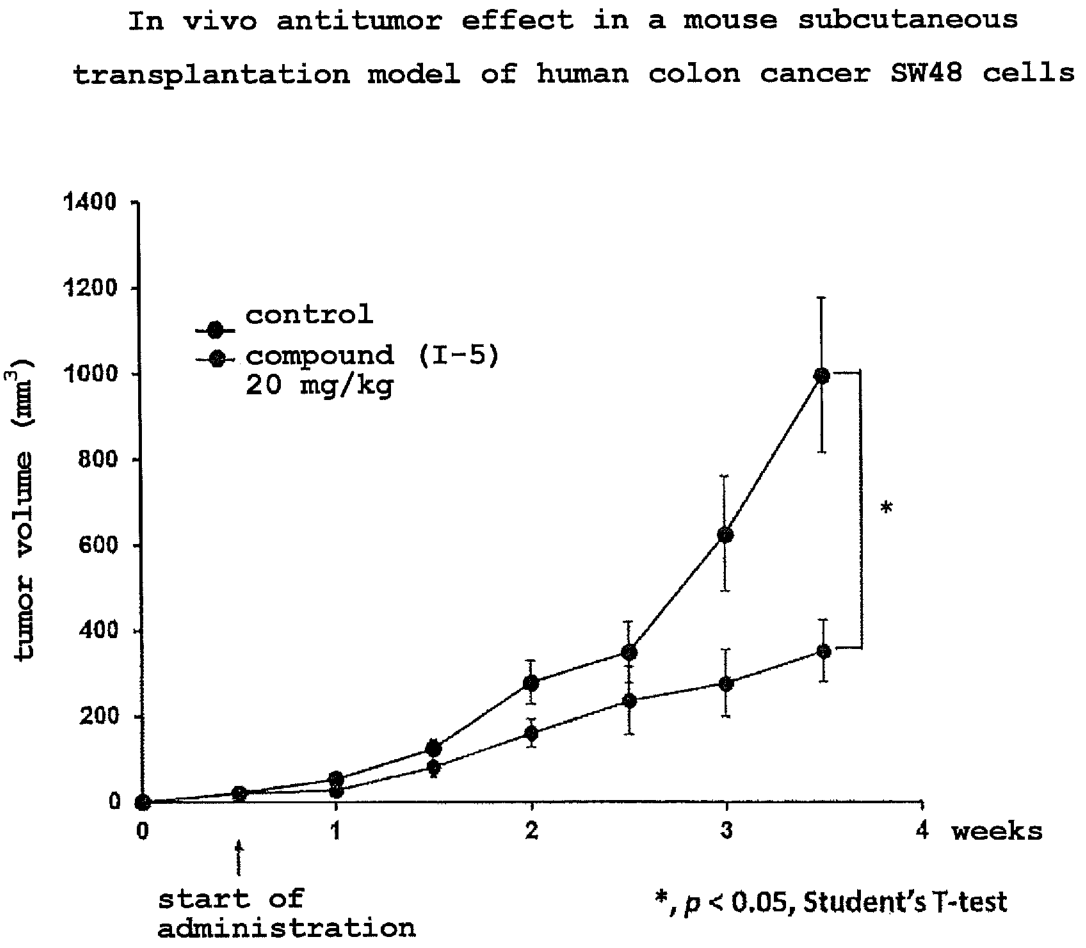

[Fig. 7]
(B)
In vivo antitumor effect in a mouse subcutaneous transplantation model of human colon cancer SW48 cells (tumor weight at 3.5 weeks)
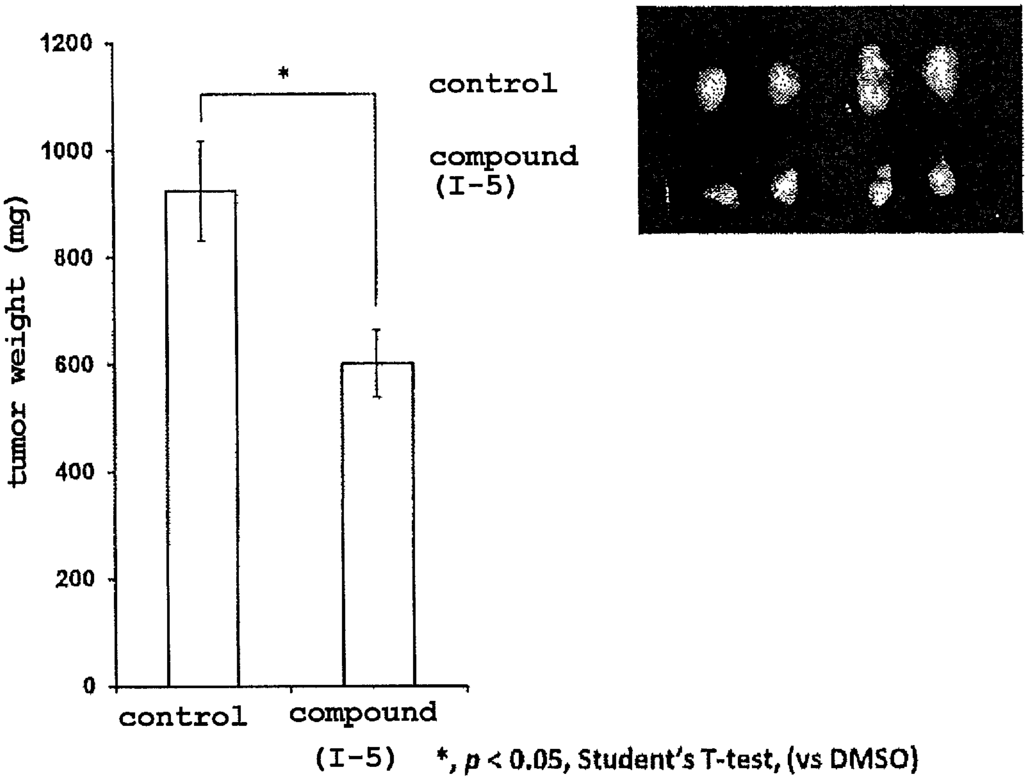

[Fig. 7]
(C)
Changes in body weight due to consecutive daily intraperitoneal administration of compound (I-5), 20 mg/kg, for 3.5 weeks
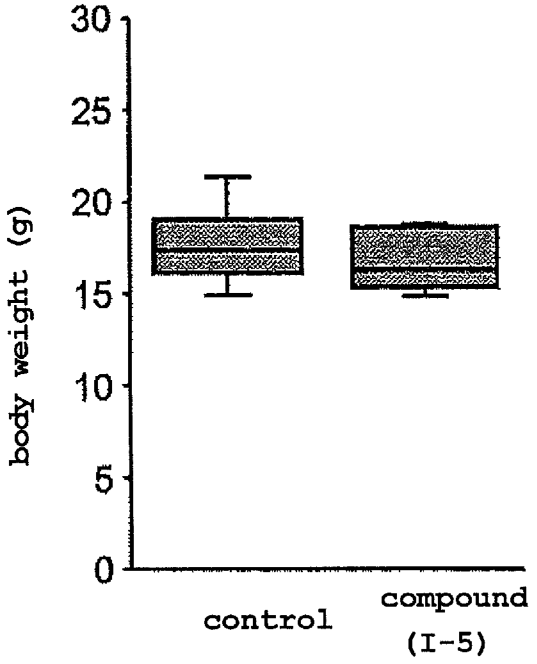

[Fig. 8]
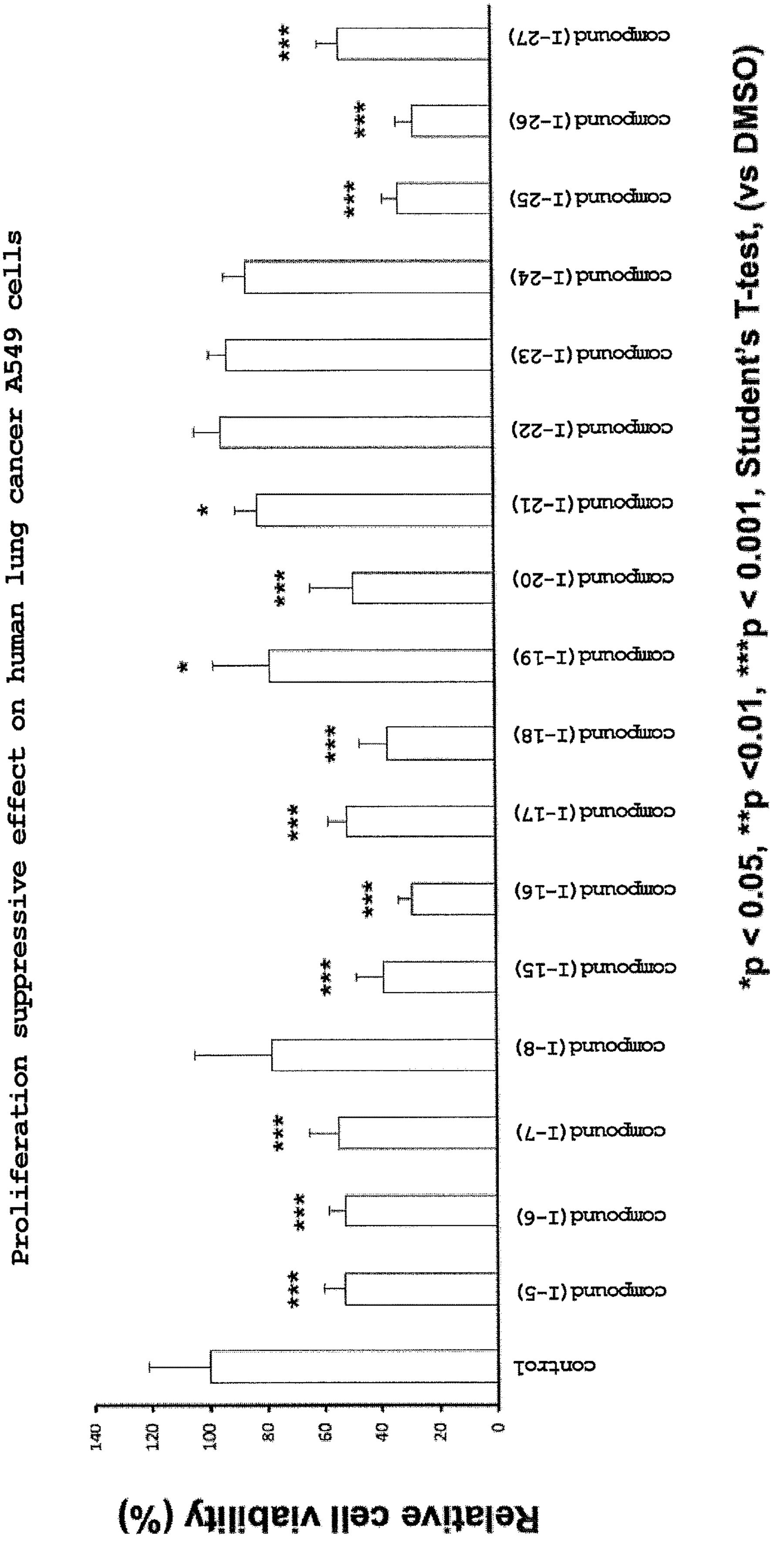

[Fig. 9]
Phosphorylated AMPK increasing action on human lung cancer A549 cells
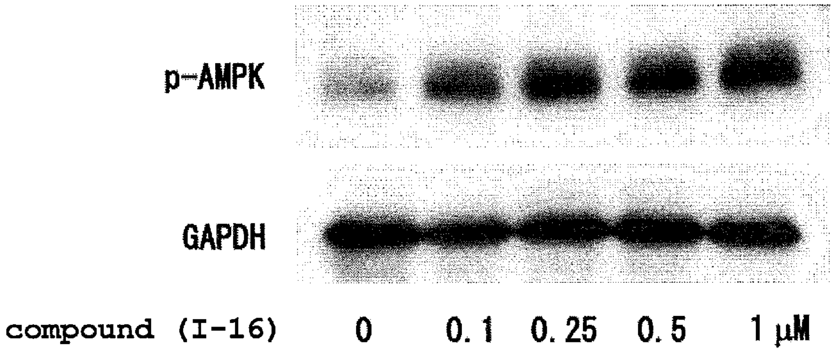

AMP-ACTIVATED PROTEIN KINASE ACTIVATOR

CROSS REFERENCE TO RELATED APPLICATIONS

This application is a U.S. national stage of International Patent Application No. PCT/JP2022/023390, filed Jun. 3, 2022, which claims the benefit of Japanese Patent Application No. 2021-094481, filed Jun. 4, 2021, the entire contents of each of which are fully incorporated herein by reference.

TECHNICAL FIELD

The present invention relates to a novel polyether compound having an AMP-activated protein kinase activating action and useful for the prophylaxis and/or treatment of diseases caused by a decrease in AMP-activated protein kinase activity.

The present invention also relates to a pharmaceutical composition containing the aforementioned novel polyether compound.

BACKGROUND ART

In recent years, hyperglycemia and hyperinsulinemia have been clarified to increase the risk of development, proliferation, and recurrence of cancer cells. One of the causes thereof is insulin resistance. As a factor that improves insulin resistance, AMP-activated protein kinase (AMPK) has been attracting attention recently (NPL 1).

AMPK is a type of serine threonine kinase (serine threonine phosphorylase) present in eukaryotic cells of from humans to yeasts, plays an important role as a sensor for intracellular energy, and is a protein kinase activated with AMP (adenosine Monophosphate: adenosine-1-phosphate) produced using adenosine triphosphate as energy. That is, AMPK is activated in response to an increase in AMP under conditions where ATP delivery is depleted in cells in low glucose, hypoxia, ischemia, heat shock, and the like.

When AMPK is activated, the synthesis of sugars, fats, and proteins is suppressed, and the degradation (catabolism) of sugars, fats, and proteins is enhanced to produce ATP. As a result, the same effect as exercise can be obtained, which is known to be effective in the treatment of obesity and diabetes (NPL 2).

Furthermore, it has been reported in recent years that metabolic syndrome, in which the activity of AMPK decreases, is a risk factor for cancer, that the activity of AMPK is suppressed even in cancer cells, and further that activation of AMPK makes it possible to suppress the proliferation of cancer cells. Thus, AMPK is considered to be promising as a target for the prophylaxis and/or treatment of cancer (NPL 3).

Metformin, cordicepin, resveratrol, oleanolic acid, cryptotansinone, verberine, and the like have been so far reported as activators of AMPK (NPL 4).

Under such circumstances, there is a demand for the development of a novel AMPK activator as an effective prophylactic and/or therapeutic agent for cancer as well as obesity and type 2 diabetes.

CITATION LIST

Non Patent Literature

[NPL 1]
J. Clin. Invest., 2013, July; 123(7):2764-72.
[NPL 2]
Diabetes Metab. J., 2013, February; 37(1):1-21.
[NPL 3]
J. Physiol., 2006, Jul. 1; 574(Pt 1):63-71.
[NPL 4]
Exp. Mol. Med., 2016, Apr. 1; 48(4): e224.

SUMMARY OF INVENTION

Technical Problem

An object of the present invention is to develop a novel AMPK activator that exhibits an excellent AMPK activating action, that can be easily synthesized, and that is stable and easy to handle. Another object of the present invention is to provide a prophylactic and/or therapeutic agent for cancer, containing the AMPK activator as an active ingredient.

Solution to Problem

The present inventors have conducted intensive studies in an attempt to solve the above-mentioned problems and found that a compound represented by the formula (I):

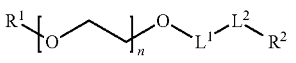

(I)

wherein $R^1$ is a hydrogen atom or an optionally substituted $C_{1-20}$ alkyl group;

$R^2$ is an optionally substituted 5- or 6-membered monocyclic aromatic heterocyclic group;

$L^1$ is a $C_{1-20}$ alkylene group optionally substituted by a hydroxy group;

$L^2$ is a divalent group represented by the formula:

$*N(R^3)C(=O)**$ or the formula:

$*N(R^3)S(O)_2**$ wherein $R^3$ is a hydrogen atom or a $C_{1-6}$ alkyl group; * represents a bonding position to $L^1$; and ** represents a bonding position to $R^2$; and n is an integer of 1 to 10

(hereinafter sometimes to be abbreviated as "compound (I)") or a pharmaceutically acceptable salt thereof shows a superior AMP-activated protein kinase activating action, which resulted in the completion of the present invention.

That is, the present invention provides the following.

[1] An AMP-activated protein kinase activator comprising a compound represented by the formula (I):

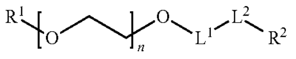

(I)

wherein $R^1$ is a hydrogen atom or an optionally substituted $C_{1-20}$ alkyl group;

$R^2$ is an optionally substituted 5- or 6-membered monocyclic aromatic heterocyclic group;

$L^1$ is a $C_{1-20}$ alkylene group optionally substituted by a hydroxy group;

$L^2$ is a divalent group represented by the formula:

$*N(R^3)C(=O)**$ or the formula:

$*N(R^3)S(O)_2**$ wherein $R^3$ is a hydrogen atom or a $C_{1-6}$ alkyl group; * represents a bonding position to $L^1$; and ** represents a bonding position to $R^2$; and n is an integer of 1 to 10, or a pharmaceutically acceptable salt thereof as an active ingredient.

[2] The AMP-activated protein kinase activator of the above-mentioned [1], wherein $R^1$ is a hydrogen atom, or a $C_{1-10}$ alkyl group optionally substituted by a hydroxy group or a $C_{2-6}$ alkynyl group, $R^2$ is an optionally substituted 5-membered monocyclic aromatic heterocyclic group, $L^1$ is a $C_{1-20}$ alkylene group optionally substituted by a hydroxy group, $L^2$ is a divalent group represented by the formula:

$*NHC(=O)**$ or the formula:

$*NHS(O)_2**$ (wherein * and ** are as defined above); and n is an integer of 1 to 8.

[3] The AMP-activated protein kinase activator of the above-mentioned [1] or [2], wherein $R^2$ is a 5-membered monocyclic aromatic heterocyclic group optionally substituted by a substituent selected from the group consisting of a halogen atom, an optionally substituted $C_{1-6}$ alkyl group, an optionally substituted $C_{6-10}$ aryl group, a cyano group, a nitro group, a carboxy group, a $C_{1-6}$ alkoxy-carbonyl group, and an acyl group.

[4] The AMP-activated protein kinase activator of the above-mentioned [3], wherein the 5-membered monocyclic aromatic heterocyclic group is a thienyl group or a pyrazolyl group.

[5] The AMP-activated protein kinase activator of the above-mentioned [1], wherein $R^1$ is a hydrogen atom, or a $C_{1-10}$ alkyl group optionally substituted by a hydroxy group or a $C_{2-6}$ alkynyl group, $R^2$ is a thienyl group or a pyrazolyl group, each of which is optionally substituted by a substituent selected from the group consisting of a halogen atom, an optionally substituted $C_{1-6}$ alkyl group, an optionally substituted $C_{6-10}$ aryl group, a cyano group, a nitro group, a carboxy group, a $C_{1-6}$ alkoxy-carbonyl group, and an acyl group, $L^1$ is a $C_{1-20}$ alkylene group optionally substituted by a hydroxy group, $L^2$ is a divalent group represented by the formula:

$*NHC(=O)**$ or the formula:

$*NHS(O)_2**$ (wherein * and ** are as defined above), and n is an integer of 1 to 8.

[6] The AMP-activated protein kinase activator of the above-mentioned [5], wherein $R^1$ is a $C_{8-10}$ alkyl group optionally substituted by a hydroxy group or an ethynyl group, $R^2$ is a 2-thienyl group, a 3-thienyl group, or a 5-pyrazolyl group, each of which is optionally substituted by a substituent selected from the group consisting of a halogen atom, a $C_{1-6}$ alkyl group, a cyano group, a nitro group, a carboxy group, and a $C_{1-6}$ alkoxy-carbonyl group, $L^1$ is a $C_{6-12}$ alkylene group, and n is an integer of 1 to 6.

[7] A medicament for the prophylaxis or treatment of a disease caused by decreased activity of AMP-activated protein kinase, comprising the AMP-activated protein kinase activator of any of the above-mentioned [1] to [6] as an active ingredient.

[8] The medicament of the above-mentioned [7], wherein the disease caused by decreased activity of AMP-activated protein kinase is diabetes, obesity, or cancer.

[9] The medicament of the above-mentioned [8], wherein the disease caused by decreased activity of AMP-activated protein kinase is cancer.

[10] The medicament of the above-mentioned [9], which is used in combination with other medicament.

[11] The medicament of the above-mentioned [10], wherein said other medicament is an anticancer agent.

[12] The medicament of the above-mentioned [11], wherein the anticancer agent is at least one kind of medicament selected from the group consisting of a chemotherapeutic agent, an immunotherapeutic agent, and a hormone therapeutic agent.

[13] The medicament of any of the above-mentioned [10] to [12], wherein the medicament of any of the above-mentioned [7] to [9] and said other medicament are administered separately.

[14] The medicament of any of the above-mentioned [10] to [12], wherein the medicament of any of the above-mentioned [7] to [9] and said other medicament are administered simultaneously or sequentially.

[15] A compound represented by the formula (I):

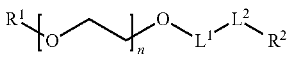

(I)

wherein $R^1$ is a hydrogen atom, or a $C_{1-10}$ alkyl group optionally substituted by a hydroxy group or a $C_{2-6}$ alkynyl group;

$R^2$ is a thienyl group or a pyrazolyl group, each of which is optionally substituted by a substituent selected from the group consisting of a halogen atom, an optionally substituted $C_{1-6}$ alkyl group, an optionally substituted $C_{6-11}$ aryl group, a cyano group, a nitro group, a carboxy group, a $C_{1-6}$ alkoxy-carbonyl group, and an acyl group, $L^1$ is a $C_{1-20}$ alkylene group optionally substituted by a hydroxy group, $L^2$ is a divalent group represented by the formula:

$*NHC(=O)**$ or the formula:

$*NHS(O)_2**$ wherein * represents a bonding position to $L^1$; and ** represents a bonding position to $R^2$; and n is an integer of 1 to 8, or a salt thereof.

[16] The compound of the above-mentioned [15], wherein $R^1$ is a $C_{8-10}$ alkyl group optionally substituted by a hydroxy group or an ethynyl group, $R^2$ is a 2-thienyl group, a 3-thienyl group, or a 5-pyrazolyl group, each of which is optionally substituted by a substituent selected from the group consisting of a halogen atom, a $C_{1-6}$ alkyl group, a cyano group, a nitro group, a carboxy group, and a $C_{1-6}$ alkoxy-carbonyl group, $L^1$ is a $C_{6-12}$ alkylene group, and n is an integer of 1 to 6, or a salt thereof.

[17] A method for the prophylaxis and/or treatment of cancer, comprising administering a prophylactically and/or therapeutically effective amount of the compound of the above-mentioned [15] or [16] or a salt thereof to a subject.

[18] The compound of the above-mentioned [15] or [16] or a salt thereof for use in the prophylaxis and/or treatment of cancer.

[19] A pharmaceutical composition comprising the compound of the above-mentioned [15] or [16] or a salt thereof for use in the prophylaxis and/or treatment of cancer.

[20] Use of the compound of the above-mentioned [15] or [16] or a salt thereof for the production of a medicament for use in the prophylaxis and/or treatment of cancer.

Advantageous Effects of Invention

The compound (I) or a pharmaceutically acceptable salt thereof of the present invention (these are sometimes collectively referred to as "the compound of the present invention" in the present specification) shows a superior AMP-activated protein kinase activating action. Hence, the medicaments (pharmaceutical compositions) containing the compound of the present invention are useful for the prophylaxis and/or treatment of the diseases caused by decreased activity of AMP-activated protein kinase (e.g., diabetes, obesity, cancer, etc.). Particularly, they can be superior agents for the prophylaxis and/or treatment of solid tumors such as glioblastoma, gastric cancer, colon cancer, lung cancer, breast cancer, germ cell cancer, liver cancer, skin cancer, bladder cancer, prostate cancer, uterine cancer, cervical cancer, ovarian cancer and the like. In addition, the compound of the present invention, has advantages in that it is easy to synthesize, stable, and easy to handle.

BRIEF DESCRIPTION OF DRAWINGS

FIG. 1 shows the proliferation suppressive action of the compound of the present invention on murine glioblastoma stem cells.

FIG. 2 shows a synergistic effect on human glioblastoma cell proliferation suppressive action when temozolomide and the compound of the present invention (compound (I-5)) are used in combination.

FIG. 3 shows the in vivo antitumor effect of the compound of the present invention (compound (I-5)) in a mouse glioblastoma transplant model.

FIG. 4 shows a proliferation suppressive action of the compounds of the present invention (compound (I-4), compound (I-5), compound (I-10)) on human colon cancer SW48 cells.

FIG. 5 shows an increasing action of the compound of the present invention (compound (I-5)) on the AMP/ATP ratio of human colon cancer SW48 cells.

FIG. 6 shows a phosphorylated AMPK increasing action of the compounds of the present invention (compound (I-4), compound (I-5), compound (I-10)) on human colon cancer SW48 cells.

FIG. 7(A) shows changes in tumor volume over time in a mouse subcutaneous transplantation model of human colon cancer SW48 cells containing the compound of the present invention (compound (I-5)), (B) shows the tumor mass in a mouse subcutaneous transplantation model of human colon cancer SW48 cells 3.5 weeks after administration of the compound of the present invention (compound (I-5)), and (C) shows changes in body weight due to consecutive daily intraperitoneal administration of the compound of the present invention (compound (I-5)) for 3.5 weeks.

FIG. 8 shows the proliferation suppressive effect of the compound of the present invention on human lung cancer A549 cells.

FIG. 9 shows the phosphorylated AMPK increasing action of the compound of the present invention (compound (I-16)) on human lung cancer A549 cells.

DESCRIPTION OF EMBODIMENTS

The definitions of terms and symbols used in the present specification are explained in the following.

In the present specification, the "halogen atom" means fluorine atom, chlorine atom, bromine atom, or iodine atom.

In the present specification, the "alkyl (group)" means a linear or branched chain monovalent group having one or more carbon atoms, which is obtained by removing one hydrogen atom from any carbon atom of alkane. When the carbon number range is not particularly limited, it means a $C_{1-20}$ alkyl group.

In the present specification, the "$C_{1-20}$ alkyl (group)" means an alkyl group having 1 to 20 carbon atoms. For example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, eicosyl, and the like can be mentioned.

In the present specification, the "$C_{1-10}$ alkyl (group)" means an alkyl group having 1 to 10 carbon atoms. For example, methyl, ethyl, propyl, isopropyl, butyl, isobutyl, sec-butyl, tert-butyl, pentyl, isopentyl, neopentyl, sec-pentyl (pentan-2-yl), 3-pentyl (pentan-3-yl), tert-pentyl (1,1-dimethylpropyl), hexyl, isohexyl, 1,1-dimethylbutyl, 2,2-dimethylbutyl, 3,3-dimethylbutyl, 2-ethylbutyl, heptyl, octyl, nonyl, decyl, and the like can be mentioned.

In the present specification, the "$C_{1-6}$ alkyl (group)" means an alkyl group having 1 to 6 carbon atoms. For example, methyl, ethyl, propyl, isopropyl, butyl, isobutyl, sec-butyl, tert-butyl, pentyl, isopentyl, neopentyl, sec-pentyl (pentan-2-yl), 3-pentyl (pentan-3-yl), tert-pentyl (1,1-dimethylpropyl), hexyl, isohexyl, 1,1-dimethylbutyl, 2,2-dimethylbutyl, 3,3-dimethylbutyl, 2-ethylbutyl, and the like can be mentioned.

In the present specification, the "$C_{1-4}$ alkyl (group)" means an alkyl group having 1 to 4 carbon atoms. For example, methyl, ethyl, propyl, isopropyl, butyl, isobutyl, sec-butyl, tert-butyl, and the like can be mentioned.

In the present specification, the "alkylene (group)" means a divalent group obtained by removing one hydrogen atom from the aforementioned alkyl group. When the carbon number range is not particularly limited, it means a $C_{1-20}$ alkylene group.

In the present specification, the "$C_{1-20}$ alkylene (group)" means a linear or branched chain alkylene group having 1 to 20 carbon atoms. For example, $—CH_2—$, $—(CH_2)_2—$, $—(CH_2)_3—$, $—(CH_2)_4—$, $(CH_2)_5—$, $—(CH_2)_6—$, $—(CH_2)_7—$, $—(CH_2)_8—$, $—(CH_2)_9—$, $—(CH_2)_{10}—$, $—(CH_2)_{11}—$, $—(CH_2)_{12}—$, $—(CH_2)_{13}—$, $—(CH_2)_{14}—$, $—(CH_2)_{15}—$, $—(CH_2)_{16}—$, $—(CH_2)_{17}—$, $—(CH_2)_{18}—$, $—(CH_2)_{19}—$, $—(CH_2)_{20}—$, $—CH(CH_3)—$, $—C(CH_3)_2$, $—CH(C_2H_5)—$, $—CH(C_3H_7)—$, $—CH(CH(CH_3)_2)—$, $—(CH(CH_3))_2—$, $—CH_2—CH(CH_3)—$, $—CH(CH_3)—CH_2—$, $—CH_2—CH_2—C(CH_3)_2—$, $—C(CH_3)_2—CH_2—CH_2—$, $—CH_2—CH_2—CH_2—C(CH_3)_2—$, $—C(CH_3)_2—CH_2—CH_2—CH_2—$, and the like can be mentioned.

In the present specification, the "alkynyl (group)" means a group obtained by removing one hydrogen atom from any carbon atom of a linear or branched chain alkyne having two or more carbon atoms. When the carbon number range is not particularly limited, it means a $C_{2-20}$ alkynyl group, and a $C_{2-6}$ alkynyl group is preferred.

In the present specification, examples of the "$C_{2-6}$ alkynyl (group)" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

In the present specification, the "cycloalkyl (group)" means a cyclic alkyl group. When the carbon number range is not particularly limited, it is preferably a $C_{3-8}$ cycloalkyl group.

In the present specification, the "$C_{3-8}$ cycloalkyl (group)" means a cyclic alkyl group having 3 to 8 carbon atoms. For example, cyclopropyl, cyclobutyl, cyclopentyl, cyclohexyl, cycloheptyl, cyclooctyl, and the like can be mentioned. Among these, a $C_{3-6}$ cycloalkyl group is preferred.

In the present specification, the "alkoxy (group)" means a group in which a linear or branched chain alkyl group is bonded to an oxygen atom. The carbon number range is not particularly limited, and it is preferably a $C_{1-10}$ alkoxy group, more preferably a $C_{1-6}$ alkoxy group.

In the present specification, the "$C_{1-6}$ alkoxy (group)" means an alkoxy group having 1 to 6 carbon atoms. For example, methoxy, ethoxy, propoxy, isopropoxy, butoxy, isobutoxy, sec-butoxy, tert-butoxy, pentyloxy, isopentyloxy, neopentyloxy, hexyloxy, and the like can be mentioned. Among these, a $C_{1-4}$ alkoxy group is preferred.

In the present specification, the "alkoxy-carbonyl (group)" means a group in which the aforementioned alkoxy group is bonded to a carbonyl group. The carbon number range is not particularly limited, and it is preferably a $C_{1-10}$ alkoxy-carbonyl group, more preferably a $C_{1-6}$ alkoxy-carbonyl group.

In the present specification, the "aryl (group)" means an aromatic monocyclic or polycyclic (fused) hydrocarbon group. Specifically, for example, a $C_{6-14}$ aryl group such as phenyl, 1-naphthyl, 2-naphthyl, biphenylyl, 2-anthryl, fluorenyl, or the like can be mentioned. Among these, a $C_{6-10}$ aryl group is preferred.

In the present specification, examples of the "$C_{6-10}$ aryl (group)" include phenyl, 1-naphthyl, and 2-naphthyl. Among these, phenyl is preferred.

In the present specification, the "$C_{7-18}$ aralkyl (group)" means a group in which the aforementioned $C_{6-14}$ aryl group is bonded to the aforementioned $C_{1-4}$ alkyl group. Specifically, for example, benzyl, phenethyl, naphthylmethyl, biphenylylmethyl, and the like can be mentioned. Among these, a $C_{7-14}$ aralkyl group ($C_{6-10}$ aryl-$C_{1-4}$ alkyl group) is preferred, and a benzyl group is particularly preferred.

In the present specification, the "$C_{7-18}$ aralkyloxy (group)" means a group in which the aforementioned $C_{7-18}$ aralkyl group is bonded to an oxygen atom. Specifically, for example, benzyloxy, phenethyloxy, naphthylmethyloxy, biphenylylmethyloxy, and the like can be mentioned. Among these, a benzyloxy group is particularly preferred.

In the present specification, the "acyl (group)" means alkanoyl or aroyl, and the carbon number range is not particularly limited. It is preferably a $C_{1-7}$ alkanoyl group or a $C_{7-11}$ aroyl.

In the present specification, the "$C_{1-7}$ alkanoyl (group)" means a linear or branched chain formyl or alkylcarbonyl having 1 to 7 carbon atoms (that is, $C_{1-6}$ alkyl-carbonyl). For example, formyl, acetyl, propionyl, butyryl, isobutyryl, pentanoyl, hexanoyl, heptanoyl, and the like can be mentioned.

In the present specification, the "$C_{7-11}$ aroyl (group)" means arylcarbonyl having 7 to 11 carbon atoms (that is, $C_{6-10}$ aryl-carbonyl), and benzoyl and the like can be mentioned.

In the present specification, the "acyloxy (group)" means a group in which the aforementioned alkanoyl group or aroyl group is bonded to an oxygen atom, and the carbon number range is not particularly limited. It is preferably a $C_{1-7}$ alkanoyloxy group or a $C_{7-11}$ aroyloxy group.

In the present specification, examples of the "$C_{1-7}$ alkanoyloxy (group)" include formyloxy, acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy (pivaloyloxy), pentylcarbonyloxy, isopentylcarbonyloxy, neopentylcarbonyloxy, hexylcarbonyloxy, and the like. It is preferably acetoxy or pivaloyloxy.

In the present specification, examples of the "$C_{7-11}$ aroyloxy (group)" include benzoyloxy, 1-naphthoyloxy, 2-naphthoyloxy, and the like.

In the present specification, the "$C_{1-6}$ alkylsulfonyl (group)" means a group in which the aforementioned "$C_{1-6}$ alkyl" group is bonded to a sulfonyl group, that is, a linear or branched chain alkylsulfonyl group having 1 to 6 carbon atoms. Examples of the "$C_{1-6}$ alkylsulfonyl (group)" include methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, 1-ethylpropylsulfonyl, hexylsulfonyl, and the like.

In the present specification, the "alkylsulfonyloxy (group)" means a group in which the aforementioned "alkylsulfonyl group" is bonded to an oxygen atom, and the carbon number range is not particularly limited. It is preferably a $C_{1-6}$ alkylsulfonyloxy group.

In the present specification, the "$C_{1-6}$ alkylsulfonyloxy (group)" means a group in which a $C_{1-6}$ alkylsulfonyl group is bonded to an oxygen atom. For example, methylsulfonyloxy, ethylsulfonyloxy, propylsulfonyloxy, isopropylsulfonyloxy, butylsulfonyloxy, and the like can be mentioned.

In the present specification, the "arylsulfonyl (group)" means a group in which the aforementioned "aryl group" is bonded to a sulfonyl group, and the carbon number range is not particularly limited. It is preferably a $C_{6-10}$ arylsulfonyl group.

In the present specification, the "$C_{6-10}$ arylsulfonyl (group)" means a group in which a "$C_{6-10}$ aryl group" is bonded to a sulfonyl group. For example, phenylsulfonyl, 1-naphthylsulfonyl, 2-naphthylsulfonyl, and the like can be mentioned.

In the present specification, the "arylsulfonyloxy (group)" means a group in which an arylsulfonyl group is bonded to an oxygen atom, and the carbon number range is not particularly limited. It is preferably a $C_{6-10}$ arylsulfonyloxy group.

In the present specification, the "$C_{6-10}$ arylsulfonyloxy (group)" means a group in which a $C_{6-10}$ arylsulfonyl group is bonded to an oxygen atom. For example, phenylsulfonyloxy, 1-naphthylsulfonyloxy, 2-naphthylsulfonyloxy, and the like can be mentioned.

In the present specification, the "substituted amino group" means a group in which at least one of the two hydrogen atoms of the amino group is substituted with a group other than a hydrogen atom, and when both of the two hydrogen atoms are substituted with substituents, the substituents may be the same or different from each other.

In the present specification, the "tri-substituted silyl (group)" means a silyl group substituted by the same or different three substituents (e.g., $C_{1-6}$ alkyl group, $C_{6-10}$ aryl group, etc.). The group is preferably a trialkylsilyl group such as a trimethylsilyl group, a triethylsilyl group, a triisopropylsilyl group, a tert-butyldimethylsilyl group, or the like (preferably, tri-$C_{1-6}$ alkylsilyl group, more preferably, tri-$C_{1-4}$ alkylsilyl group), a tert-butyldiphenylsilyl group, a triphenyl silyl group, or the like.

In the present specification, the "tri-substituted silyloxy (group)" means a group in which a tri-substituted silyl group is bonded to an oxygen atom. The group is preferably a trialkylsilyloxy group such as a trimethylsilyloxy group, a triethylsilyloxy group, a triisopropylsilyloxy group, a tert-butyldimethylsilyloxy group, or the like (preferably, tri-$C_{1-6}$ alkylsilyloxy group, more preferably, tri-$C_{1-4}$ alkylsilyloxy group), tert-butyldiphenylsilyloxy group, triphenylsilyloxy group, or the like is preferred.

In the present specification, as the substituent constituting the "substituted amino group", for example, the amino-protecting groups described in Protective Groups in Organic Synthesis, John Wiley and Sons (the 3rd edition, 1999) and the like can be used. Examples thereof include protecting groups such as $C_{1-6}$ alkyl group, $C_{1-6}$ alkylsulfonyl, $C_{7-22}$ aralkyl group, $C_{6-10}$ aryl group, $C_{1-7}$ alkanoyl group, $C_{7-11}$ aroyl group, $C_{7-14}$ aralkyl-carbonyl group, $C_{1-6}$ alkoxy-carbonyl group, $C_{7-14}$ aralkyloxy-carbonyl group, $C_{6-10}$ arylsulfonyl, tri-$C_{1-6}$ alkylsilyl group (e.g., tri-$C_{1-6}$ alkylsilyl group (e.g., trimethylsilyl, tert-butyl(dimethyl)silyl), and the like. The above-mentioned protecting group is optionally further substituted by a halogen atom, a $C_{1-6}$ alkyl group, a $C_{1-6}$ alkoxy group, or a nitro group. Specific examples of the amino-protecting group include methyl (monomethyl or dimethyl), benzyl, trityl, acetyl, trifluoroacetyl, pivaloyl, tert-butoxycarbonyl, benzyloxycarbonyl, trifluoromethanesulfonyl, p-toluenesulfonyl, and the like.

In the present specification, as the "5- or 6-membered monocyclic aromatic heterocyclic group", a 5- or 6-membered monocyclic aromatic heterocyclic group containing, as a ring-constituting atom other than carbon atom, 1 to 4 hetero atoms selected from an oxygen atom, a sulfur atom, and a nitrogen atom can be mentioned.

Preferred examples of the 5- or 6-membered monocyclic aromatic heterocyclic group include furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, triazinyl, and the like. Among these, thienyl or pyrazolyl is preferred.

"Optionally substituted" means unsubstituted or having 1 to 5 (preferably 1 to 3) substituents at substitutable positions, and each substituent may be the same or different.

Examples of the substituent of the "optionally substituted" include (1) a halogen atom, (2) a hydroxy group, (3) a cyano group, (4) a nitro group, (5) an azido group, (6) a substituted amino group, (7) a $C_{1-6}$ alkyl group, (8) a $C_{1-6}$ alkoxy group, (9) a $C_{3-8}$ cycloalkyl group, (10) a $C_{2-6}$ alkynyl group, (11) a $C_{6-10}$ aryl group, (12) a $C_{7-18}$ aralkyl group, (13) a $C_{7-18}$ aralkyloxy group, (14) an acyl group (e.g., $C_{1-7}$ alkanoyl group, $C_{7-11}$ aroyl group), (15) a $C_{1-7}$ alkanoyloxy group, (16) a $C_{7-11}$ aroyloxy group, (17) a $C_{1-6}$ alkoxy-carbonyl group, (18) a carbamoyl group optionally mono- or di-substituted by a $C_{1-6}$ alkyl group, (19) a $C_{1-6}$ alkylsulfonyloxy group, (20) a $C_{6-10}$ arylsulfonyloxy group, (21) a tri-substituted silyl group, (22) a tri-substituted silyloxy group, (23) a carboxy group, and the like. Among these, a halogen atom, $C_{1-6}$ alkyl, $C_{1-6}$ alkoxy, acetyl, formyl, carbamoyl, azido, trimethylsilyl, triethylsilyl, triisopropylsilyl, tert-butyldimethylsilyl, tert-butyldimethylsilyloxy, phenyl, cyclopropyl, cyclohexyl, dimethylamino, acetylamino, tert-butoxycarbonylamino, benzyloxycarbonylamino, methoxycarbonyl, carboxy, and the like are preferred.

The substituents of "optionally substituted alkyl" or "optionally substituted alkylene" include substituents obtained by removing "(7) a $C_{1-6}$ alkyl group" and "(12) a $C_{7-18}$ aralkyl group" from the above-mentioned substituent list.

The above-mentioned substituents are each optionally further substituted by one or more of a halogen atom, a hydroxy group, a $C_{1-6}$ alkyl group, a $C_{1-6}$ alkoxy group, a cyano group, a nitro group, a phenyl group, a carboxy group, and the like.

In the present specification, the "pharmaceutically acceptable salt thereof" means a salt that can be used as a medicament. When compound (I) of the present invention has an acidic group or a basic group, it means a salt obtained by converting the compound to a basic salt or an acidic salt by reacting with a base or an acid.

Examples of the pharmaceutically acceptable "basic salt" of compound (I) of the present invention include alkali metal salts such as sodium salt, potassium salt, lithium salt, and the like; alkaline earth metal salts such as magnesium salt, calcium salt, and the like; organic base salts such as N-methylmorpholine salt, triethylamine salt, tributylamine salt, diisopropylethylamine salt, dicyclohexylamine salt, N-methylpiperidine salt, pyridine salt, 4-pyrrolidinopyridine salt, picoline salt, and the like; amino acid salts such as glycinate, lysinate, argininate, ornithinate, glutamate, aspartate, and the like, and the like, and alkali metal salts are preferred.

Examples of the pharmaceutically acceptable "acidic salt" of compound (I) of the present invention include hydrohalides such as hydrofluoride, hydrochloride, hydrobromide, hydroiodide, and the like, inorganic acid salts such as nitrate, perchlorate, sulfate, phosphate, and the like; lower alkanesulfonates such as methanesulfonate, trifluoromethanesulfonate, ethanesulfonate, and the like; arylsulfonates such as benzenesulfonate, p-toluenesulfonate, and the like; organic acid salts such as acetate, malate, fumarate, succinate, citrate, ascorbate, tartrate, oxalate, maleate, and the like; amino acid salts such as glycinate, lysinate, argininate, ornithinate, glutamate, aspartate, and the like. Hydrohalides (particularly, hydrochloride) are preferred.

In the present specification, the "salt thereof" means salts in general, including the aforementioned "pharmaceutically acceptable salt thereof".

In the present specification, the "prophylaxis" includes preventing the onset of a disease, delaying the onset of a disease, and preventing the development of pathology. The "prophylactically effective amount" refers to a dose of an active ingredient sufficient to achieve the prophylactic purposes.

In the present specification, the "treatment" includes curing the disease, improving the pathology of the disease (e.g., one or more symptoms), and suppressing the progression of (the severity of) the disease. The "therapeutically effective amount" refers to a dose of an active ingredient sufficient to achieve a therapeutic purposes. Therefore, the "improvement" is a concept included in the "treatment".

In the present specification, the "subject" means a subject to whom a medicament (pharmaceutical composition) containing an effective amount of an active ingredient necessary for preventing and/or treating (or improving) a disease or the pathology of a disease is administered. The "subject" includes a human or a non-human animal (particularly a mammal (e.g., mouse, rat, guinea pig, hamster, rabbit, cat, dog, cow, sheep, monkey, etc.)).

In the present specification, the "AMP-activated protein kinase activator" is a medicament that activates (or induces) AMP-activated protein kinase, and means a medicament that exhibits AMP-activated protein kinase agonist activity. The AMP-activated protein kinase activating action (AMP-activated protein kinase agonist activity) can be measured by methods described in literatures (e.g., J. Cell Sci., 2004, Nov. 1; 117(Pt 23):5479-87) and the method described in the below-mentioned Experimental Examples.

Compound (I) of the Present Invention

Each group in compound (I) of the present invention is explained below.

$R^1$ is a hydrogen atom or an optionally substituted $C_{1-20}$ alkyl group.

$R^1$ is preferably a hydrogen atom, or a $C_{1-10}$ alkyl group optionally substituted by a hydroxy group or a $C_{2-6}$ alkynyl group, more preferably, a hydrogen atom, or a $C_{1-10}$ alkyl group optionally substituted by a hydroxy group or a $C_{2-6}$ alkynyl group, further preferably a $C_{8-10}$ alkyl group optionally substituted by a hydroxy group or an ethynyl group.

$R^2$ is an optionally substituted 5- or 6-membered monocyclic aromatic heterocyclic group.

$R^2$ is preferably an optionally substituted 5-membered monocyclic aromatic heterocyclic group, more preferably a 5-membered monocyclic aromatic heterocyclic group optionally substituted by a substituent selected from the group consisting of a halogen atom, an optionally substituted $C_{1-6}$ alkyl group, an optionally substituted $C_{6-10}$ aryl group, a cyano group, a nitro group, a carboxy group, a $C_{1-6}$ alkoxy-carbonyl group, and an acyl group, further preferably a thienyl group or a pyrazolyl group each optionally substituted by a substituent selected from the group consisting of a halogen atom, an optionally substituted $C_{1-6}$ alkyl group, an optionally substituted $C_{6-10}$ aryl group, a cyano group, a nitro group, a carboxy group, a $C_{1-6}$ alkoxy-carbonyl group, and an acyl group, particularly preferably 2-thienyl group, 3-thienyl group or a 5-pyrazolyl group each optionally substituted by a substituent selected from the group consisting of a halogen atom, a $C_{1-6}$ alkyl group, a cyano group, a nitro group, a carboxy group, and a $C_{1-6}$ alkoxy-carbonyl group.

$L^1$ is a $C_{1-20}$ alkylene group optionally substituted by a hydroxy group.

$L^1$ is preferably a $C_{1-20}$ alkylene group optionally substituted by a hydroxy group, more preferably a $C_{6-12}$ alkylene group.

$L^2$ is a divalent group represented by the formula:

$*N(R^3)C(=O)**$ or the formula:

$N(R^3)S(O)_2**$ wherein $R^3$ is a hydrogen atom or a $C_{1-6}$ alkyl group; * represents a bonding position to $L^1$; and ** represents a bonding position to $R^2$.

$L^2$ is preferably a divalent group represented by the formula:

$*NHC(=O)**$ or the formula:

$*NHS(O)_2**$ wherein * and ** are as defined above, more preferably, a divalent group represented by the formula:

$*NHC(=O)**$ wherein * and ** are as defined above.

n is an integer of 1 to 10.

n is preferably an integer of 1 to 8, more preferably an integer of 1 to 6, particularly preferably an integer of 3 to 5.

As compound (I), the following compounds are preferred.

[Compound (IA)]

Compound (I) wherein $R^1$ is a hydrogen atom, or a $C_{1-10}$ alkyl group optionally substituted by a hydroxy group or a $C_{2-6}$ alkynyl group;

$R^2$ is an optionally substituted 5-membered monocyclic aromatic heterocyclic group;

$L^1$ is a $C_{1-20}$ alkylene group optionally substituted by a hydroxy group;

$L^2$ is a divalent group represented by the formula:

$*NHC(=O)**$ or the formula:

$*NHS(O)_2**$ wherein * is a bonding position to $L^1$; and ** is a bonding position to $R^2$; and n is an integer of 1 to 8, or a pharmaceutically acceptable salt thereof.

[Compound (IB)]

Compound (I) wherein $R^1$ is a hydrogen atom, or a $C_{1-10}$ alkyl group optionally substituted by a hydroxy group or a $C_{2-6}$ alkynyl group;

$R^2$ is a 5-membered monocyclic aromatic heterocyclic group optionally substituted by a substituent selected from the group consisting of a halogen atom, an optionally substituted $C_{1-6}$ alkyl group, an optionally substituted $C_{6-10}$ aryl group, a cyano group, a nitro group, a carboxy group, a $C_{1-6}$ alkoxy-carbonyl group, and an acyl group;

$L^1$ is a $C_{1-20}$ alkylene group optionally substituted by a hydroxy group;

$L^2$ is a divalent group represented by the formula:

*NHC(=O)**

or the formula:

$*NHS(O)_2**$ wherein * is a bonding position to $L^1$; and ** is a bonding position to $R^2$; and n is an integer of 1 to 8, or a pharmaceutically acceptable salt thereof.

[Compound (IC)]

Compound (I) wherein $R^1$ is a hydrogen atom, or a $C_{1-10}$ alkyl group optionally substituted by a hydroxy group or a $C_{2-6}$ alkynyl group;

$R^2$ is a thienyl group or a pyrazolyl group each optionally substituted by a substituent selected from the group consisting of a halogen atom, an optionally substituted $C_{1-6}$ alkyl group, an optionally substituted $C_{6-10}$ aryl group, a cyano group, a nitro group, a carboxy group, a $C_{1-6}$ alkoxy-carbonyl group, and an acyl group;

$L^1$ is a $C_{1-20}$ alkylene group optionally substituted by a hydroxy group;

$L^2$ is a divalent group represented by the formula:

*NHC(=O)**

or the formula:

$*NHS(O)_2**$ wherein * is a bonding position to $L^1$; and ** is a bonding position to $R^2$; and n is an integer of 1 to 8, or a pharmaceutically acceptable salt thereof.

[Compound (ID)]

Compound (I) wherein $R^1$ is a $C_{8-10}$ alkyl group optionally substituted by a hydroxy group or an ethynyl group;

$R^2$ is a 2-thienyl group, a 3-thienyl group, or a 5-pyrazolyl group each optionally substituted by a substituent selected from the group consisting of a halogen atom, a $C_{1-6}$ alkyl group, a cyano group, a nitro group, a carboxy group, and a $C_{1-6}$ alkoxy-carbonyl group;

$L^1$ is a $C_{6-12}$ alkylene group;

$L^2$ is a divalent group represented by the formula:

*NHC(=O)**

or the formula:

$*NHS(O)_2**$ wherein * is a bonding position to $L^1$, and ** is a bonding position to $R^2$; and n is an integer of 1 to 6, or a pharmaceutically acceptable salt thereof.

[Compound (IE)]

Compound (I) wherein $R^1$ is a $C_{8-10}$ alkyl group optionally substituted by a hydroxy group or an ethynyl group;

$R^2$ is a 2-thienyl group, a 3-thienyl group, or a 5-pyrazolyl group each optionally substituted by a substituent selected from the group consisting of a halogen atom, a $C_{1-6}$ alkyl group, a cyano group, a nitro group, a carboxy group, and a $C_6$ alkoxy-carbonyl group;

$L^1$ is a $C_{6-12}$ alkylene group;

$L^2$ is a divalent group represented by the formula:

*NHC(=O)**

or the formula:

$*NHS(O)_2**$ wherein * is a bonding position to $L^1$, and ** is a bonding position to $R^2$; and n is an integer of 3 to 5, or a pharmaceutically acceptable salt thereof.

Preferred specific examples of compound (I) include the compounds of Examples 1 to 27 described in the following Example (compound (I-1) to compound (I-27)). Among those, compound (I-2), compound (I-4), compound (I-5), compound (I-6), compound (I-7), compound (I-15), compound (I-16), compound (I-17), compound (I-18), compound (I-20), compound (I-25), compound (I-26), and compound (I-27), and pharmaceutically acceptable salts thereof are particularly preferred.

Production Method of Compound (I) of the Present Invention

The production methods of compound (I) of the present invention are described in the following.

As examples of the method for producing compound (I), representative production methods are described below, but the production methods are not limited thereto.

Compound (I) can be produced by the methods shown in the synthesis schemes below, the Reference Examples and Examples described later, or a method analogous thereto.

Each raw material compound may form a salt as long as it does not inhibit the reaction, and such salt includes those similar to the pharmaceutically acceptable salts of compound (I).

Unless a specific production method is stated, a commercially available raw material compound can be obtained and used easily, or it can be produced according to a method known per se or a method analogous thereto. Furthermore, the intermediate produced in the following production method may be isolated and purified by methods such as column chromatography, recrystallization, and distillation, or may be used in the next step without isolation.

A schematic diagram of the reaction formula of each step in the production of compound (I) is shown below, and each symbol in the compound in the diagram means the same as above.

In the present specification, the contents of all patent literatures, non patent literatures, or references expressly recited herein may now be cited as part of the present specification.

Compound (I) of the present invention can be produced according to Production Methods 1 to 6 below, but are not limited thereto.

Production Method 1

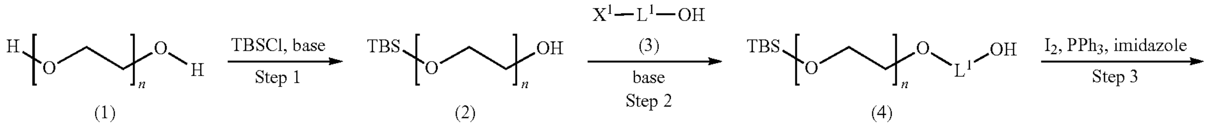

(1) (2) (4)

-continued

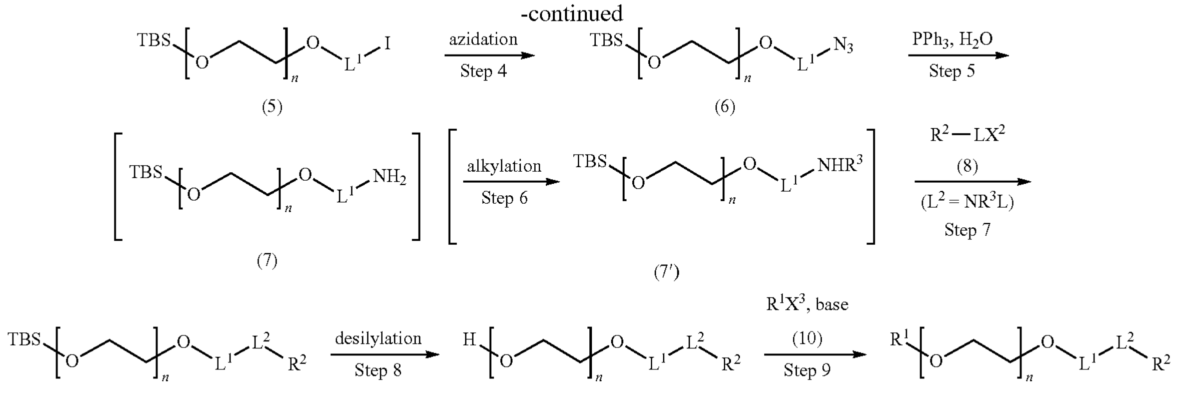

(5) (6) (7) (7') (9) (9') (I)

wherein $X^1$ represents a leaving group, $X^2$ represents a hydroxy group or a leaving group, $X^3$ represents a leaving group, and -L- represents a divalent group represented by the formula:

—C(═O)— or the formula:

$—S(O)_2—$ and other symbols are each as defined above.

(Step 1)

In this step, compound (1) is reacted with a silylating agent in the presence of a base to obtain compound (2).

Compound (1) is not particularly limited, and a commercially available product, or compound (1) synthesized by a method known per se can be preferably used.

The silylating agent is not particularly limited and a commercially available product can be preferably used. It is preferably tert-butyldimethylsilyl chloride (TBSCl).

The amount of the silylating agent (TBSCl) to be used is generally 1 to 1.5 mol, preferably 1 to 1.2 mol, per 1 mol of compound (1).

The base to be used is not particularly limited and, for example, organic bases such as triethylamine, N,N-diisopropylethylamine (DIPEA), and the like; inorganic bases such as sodium hydride and the like, and the like can be mentioned. Among these, sodium hydride is preferred.

The amount of the base to be used is generally 1 to 1.5 mol, preferably 1 to 1.2 mol, per 1 mol of compound (1).

This reaction can be carried out in a solvent that does not affect the reaction. The reaction solvent is not particularly limited and, for example, ethers such as tetrahydrofuran and the like; amides such as N,N-dimethylformamide, N,N-dimethylacetamide, and the like; halogenated hydrocarbons such as dichloromethane, chloroform, and the like, and the like can be mentioned. Among these, tetrahydrofuran is preferred.

The reaction temperature is generally −10° C. to 60° C., preferably 0° C. to 40° C., more preferably 0° C. to room temperature, and the reaction time is generally about 30 min to 6 hr.

(Step 2)

In this step, compound (2) and compound (3) are reacted as in the presence of a base to obtain compound (4).

Compound (3) is not particularly limited, and a commercially available product, or compound (3) synthesized by a method known per se (e.g., Luu, B. et al., Bioorganic & Medicinal Chemistry Letters, 2006, 16(10), 2637-2640) can be preferably used.

The amount of compound (3) to be used is generally 1 to 1.5 mol, preferably 1 to 1.2 mol, per 1 mol of compound (2).

The base to be used is not particularly limited, and examples thereof include organic bases such as triethylamine, N,N-diisopropylethylamine (DIPEA), and the like; inorganic bases, such as sodium hydride and the like, and the like. Among these, sodium hydride is preferred.

The amount of the base to be used is generally 1 to 1.5 mol, preferably 1 to 1.2 mol, per 1 mol of compound (2).

This reaction can be carried out in a solvent that does not affect the reaction. The reaction solvent is not particularly limited, and examples thereof include ethers such as tetrahydrofuran and the like; amides such as N,N-dimethylformamide, N,N-dimethylacetamide, and the like; halogenated hydrocarbons such as dichloromethane, chloroform, and the like, and the like. Among these, N,N-dimethylformamide is preferred.

The reaction temperature is generally −10° C. to 60° C., preferably 0° C. to 40° C., more preferably 0° C. to room temperature, and the reaction time is generally about 0.5 to 6 hr.

(Step 3)

In this step, compound (4) is reacted with iodine in the presence of triphenylphosphine and imidazole to obtain compound (5).

The amount of iodine to be used is generally 1 to 3 mol, preferably 1 to 2 mol, more preferably 1.5 mol, per 1 mol of compound (4).

The amount of triphenylphosphine to be used is generally 1 to 2 mol, preferably 1 to 1.2 mol, more preferably 1 mol, per 1 mol of compound (4).

The amount of imidazole to be used is generally 1 to 5 mol, preferably 1.5 to 3 mol, more preferably 2 to 3 mol, per 1 mol of compound (4).

This reaction can be carried out in a solvent that does not affect the reaction. The reaction solvent is not particularly limited, and examples thereof include ethers such as tetrahydrofuran and the like; amides such as N,N-dimethylformamide, N,N-dimethylacetamide, and the like; halogenated hydrocarbons such as dichloromethane, chloroform, and the like, and the like. Among these, dichloromethane is preferred.

The reaction temperature is generally −10° C. to 60° C., preferably 0° C. to 40° C., more preferably 0° C. to room temperature, and the reaction time is generally about 1 to 24 hr.

(Step 4)

In this step, compound (5) is azidated to obtain compound (6).

The azidating agent to be used is not particularly limited. A commercially available product such as sodium azide, azidotrimethylsilane, or the like can be preferably used and, among these, sodium azide is preferred.

The amount of the azidating agent to be used is generally 1 to 5 mol, preferably 1.5 to 3 mol, more preferably 2 mol, per 1 mol of compound (5).

This reaction can be carried out in a solvent that does not affect the reaction. The reaction solvent is not particularly limited, and examples thereof include ethers such as tetrahydrofuran and the like; amides such as N,N-dimethylformamide, N,N-dimethylacetamide, and the like; halogenated hydrocarbons such as dichloromethane, chloroform, and the like; dimethyl sulfoxide, and the like. Among these, dimethyl sulfoxide is preferred.

The reaction temperature is generally 0° C. to 60° C., preferably room temperature, and the reaction time is generally about 1 to 12 hr.

(Step 5)

In this step, compound (6) is reduced to obtain compound (7).

The reducing agent to be used is not particularly limited, and examples thereof include heterogeneous catalysts for catalytic hydrogen reduction (e.g., palladium carbon etc.), hydride reducing agents (e.g., lithium aluminum hydride, sodium borohydride-nickel (II) chloride, etc.), triphenylphosphine, and the like. Among these, Staudinger reaction in which triphenylphosphine is used in the presence of water is preferred.

The amount of triphenylphosphine to be used is generally 1 to 5 mol, preferably 1 to 2 mol, per 1 mol of compound (6).

This reaction can be carried out in a solvent that does not affect the reaction. The reaction solvent is not particularly limited, and examples thereof include mixed solvent of water and ether such as diethyl ether, tetrahydrofuran, and the like. Among these, diethyl ether-water is preferred.

The reaction temperature is generally −10° C. to 60° C., preferably 0° C. to room temperature, and the reaction time is generally about 5 min to 72 hr.

(Step 6)

In this step, compound (7) is alkylated by reacting with a hydride reducing agent in the presence of aldehyde to obtain compound (7'). This step can be omitted when producing compound (I) of the formula (I) wherein $R^3$ is a hydrogen atom.

As the aldehyde to be used, formaldehyde, acetaldehyde, and the like can be mentioned.

The amount of the aldehyde to be used is generally 1 to 1.5 mol, preferably 1 to 1.2 mol, more preferably 1 mol, per 1 mol of compound (7).

Examples of the hydride reducing agent to be used include sodium borohydride, sodium cyanoborohydride, sodium triacetoxyborohydride, and the like.

This reaction can be carried out in a solvent that does not affect the reaction. The reaction solvent is not particularly limited, and examples thereof include methanol, acetonitrile, 1,2-dichloroethane, and dichloromethane. Among these, methanol and 1,2-dichloroethane are preferred.

The reaction temperature is generally −10° C. to 60° C., preferably 0° C. to room temperature, and the reaction time is generally about 1 hr to 24 hr.

(Step 7)

In this step, compound (7) (or compound (7')) and compound (8) are reacted to obtain compound (9).

Compound (8) is not particularly limited, and a commercially available product or compound (8) synthesized by a method known per se (e.g., WO 2004/043366) can be preferably used.

The amount of compound (8) to be used is generally 1 to 5 mol, preferably 1.5 to 3 mol, per 1 mol of compound (7) (or compound (7')).

When a compound (8) wherein -L- is —C(O)— and $X^2$ is a hydroxy group is used as compound (8), compound (7) (or compound (7')) and compound (8) are reacted in a solvent that does not affect the reaction in the presence of a condensing agent to obtain compound (9).

Examples of the condensing agent include condensing agents such as carbodiimide compounds such as N,N'-dicyclohexylcarbodiimide, 1-(3-dimethylaminopropyl)-3-ethylcarbodiimide hydrochloride, N-cyclohexyl-N'-morpholinoethylcarbodiimide, N-cyclohexyl-N'-(4-diethylaminocyclohexyl)carbodiimide, and the like; azolide compounds such as N,N'-carbonyldiimidazole, N,N'-thionyldiimidazole, and the like; phosphorus compounds such as diethyl cyanophosphate and diphenyl phosphoryl azide. Among these, 1-(3-dimethylaminopropyl)-3-ethylcarbodiimide hydrochloride is preferred.

When the above-mentioned carbodiimide compound is used as a condensing agent, the reaction yield can be improved as necessary by using an additive. Examples of the additive include 1-hydroxy-7-azabenzotriazole, 1-hydroxybenzotriazole, N-hydroxysuccinimide, N-hydroxyphthalimide, and the like. Among these, 1-hydroxybenzotriazole is preferred. When the above-mentioned phosphorus compound is used as a condensing agent, the reaction yield can be improved as necessary by adding an organic base such as triethylamine, N,N-diisopropylethylamine, or the like. Furthermore, when the above-mentioned azolide compound is used as a condensing agent, the reaction is preferably carried out in the presence of a base such as an organic base such as triethylamine, N,N-diisopropylethylamine, N-methylmorpholine, 4-dimethylaminopyridine, 1,8-diazabicyclo[5,4,0]undec-7-ene, or the like; an alkali metal carbonate such as sodium carbonate, sodium hydrogen carbonate, potassium carbonate, potassium hydrogen carbonate, cesium carbonate, or the like.

The amount of the condensing agent to be used is generally 1 to 5 mol, preferably 1 to 3 mol, per 1 mol of compound (7) (or compound (7')).

The amounts of the additive, the organic base, and the alkali metal carbonate to be used are generally 1 to 5 mol, preferably 1 to 3 mol, per 1 mol of compound (7) (or compound (7')).

This reaction can be carried out in a solvent that does not affect the reaction. The reaction solvent is not particularly limited, and examples thereof include alcohols such as methanol, ethanol, propanol, 2-propanol, butanol, and the like; aromatic hydrocarbons such as benzene, toluene, xylene, and the like; ethers such as diethyl ether, diisopropyl ether, tetrahydrofuran, dioxane, 1,2-dimethoxyethane, and the like; amides such as N,N-dimethylformamide, N,N-dimethylacetamide, N-methyl-2-pyrrolidone, N-methylpyrrolidinone, hexamethylphosphoric triamide, and the like; halogenated hydrocarbons such as dichloromethane, chloroform, carbon tetrachloride, dichloroethane, chlorobenzene, o-dichlorobenzene, m-dichlorobenzene, fluorobenzene, trichloromethylbenzene, trifluoromethylbenzene, and the like, and mixtures of these. Among these, tetrahydrofuran is preferred.

The reaction conditions such as reaction temperature, reaction time, and the like vary depending on the reaction reagent, reaction solvent, and the like to be used. The reaction temperature is generally −30° C. to 150° C., preferably 0° C. to room temperature, and the reaction time is 30 min to 20 hr.

When a compound (8) wherein $X^2$ is a leaving group is used as compound (8), this reaction is generally carried out in the presence of a base in a solvent that does not affect the reaction.

The base to be used in this reaction is not particularly limited, and examples thereof include organic bases such as triethylamine, N,N-diisopropylethylamine, N-methylmorpholine, 4-dimethylaminopyridine, and the like; inorganic bases such as sodium carbonate, sodium hydrogen carbonate, potassium carbonate, potassium hydrogen carbonate, cesium carbonate, and the like, and the like.

This reaction can be carried out in a solvent that does not affect the reaction. The reaction solvent is not particularly limited, and examples thereof include alcohols such as methanol, ethanol, propanol, 2-propanol, butanol, and the like; aromatic hydrocarbons such as benzene, toluene, xylene, and the like; ethers such as diethyl ether, diisopropyl ether, tetrahydrofuran, dioxane, 1,2-dimethoxyethane, and the like; amides such as N,N-dimethylformamide, N,N-dimethylacetamide, N-methyl-2-pyrrolidone, N-methylpyrrolidinone, hexamethylphosphoric triamide, and the like; halogenated hydrocarbons such as dichloromethane, chloroform, carbon tetrachloride, dichloroethane, chlorobenzene, o-dichlorobenzene, m-dichlorobenzene, fluorobenzene, trichloromethylbenzene, trifluoromethylbenzene, and the like, and mixtures of these.

The amount of the base to be used is generally 1 to 5 mol, preferably 1 to 3 mol, per 1 mol of compound (7) (or compound (7')).

The reaction conditions such as reaction temperature, reaction time, and the like vary depending on the reaction reagent, reaction solvent, and the like to be used. The reaction temperature is generally −30° C. to 150° C., preferably 0° C. to room temperature, and the reaction time is 30 min to 20 hr.

(Step 8)

In this step, compound (9) is desilylated to obtain compound (9'). Compound (9') is encompassed in compound (I) (corresponding to compound wherein $R^1$ in the formula (I) is a hydrogen atom).

As the desilylating agent to be used, tetrabutylammonium fluoride (TBAF) is preferred.

The amount of the desilylating agent to be used is generally 1 to 30 mol, preferably 5 to 20 mol, more preferably mol, per 1 mol of compound (9).

This reaction can be carried out in a solvent that does not affect the reaction. The reaction solvent is not particularly limited, and examples thereof include ethers such as tetrahydrofuran and the like; amides such as N,N-dimethylformamide, N,N-dimethylacetamide, and the like; halogenated hydrocarbons such as dichloromethane, chloroform, and the like, and the like. Among these, tetrahydrofuran is preferred.

The reaction temperature is generally −10° C. to 60° C., preferably 0° C. to 40° C., more preferably 0° C. to room temperature, and the reaction time is generally about 30 min to 24 hr.

(Step 9)

In this step, compound (9') is reacted with compound (10) in the presence of a base to obtain compound (I).

Compound (10) is not particularly limited, and a commercially available product or compound (10) synthesized by a method known per se (e.g., Baird, M. S. et al., Tetrahedron, 2005, 61(50), 11939-11951, etc.) can be preferably used.

The amount of compound (10) to be used is generally 1 to 3 mol, preferably 2 mol, per 1 mol of compound (9').

The base to be used is not particularly limited, and examples thereof include organic bases such as triethylamine, N,N-diisopropylethylamine (DIPEA), and the like; inorganic bases such as sodium hydride and the like, and the like. Among these, sodium hydride is preferred.

The amount of the base to be used is generally 1 to 3 mol, preferably 2 mol, per 1 mol of compound (9).

This reaction can be carried out in a solvent that does not affect the reaction. The reaction solvent is not particularly limited, and examples thereof include ethers such as tetrahydrofuran and the like; amides such as N,N-dimethylformamide, N,N-dimethylacetamide, and the like; halogenated hydrocarbons such as dichloromethane, chloroform, and the like; dimethyl sulfoxide, and the like. Among these, dimethyl sulfoxide is preferred.

The reaction temperature is generally −10° C. to 60° C., preferably 0° C. to 40° C., more preferably 0° C. to room temperature, and the reaction time is generally about 1 hr to 24 hr.

Production Method 2

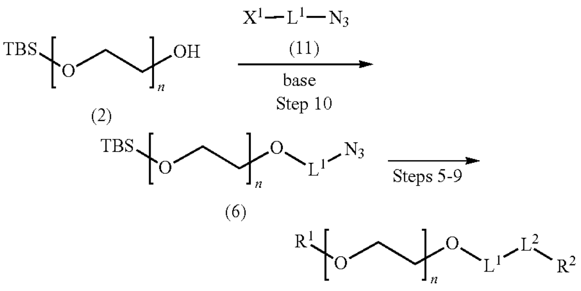

(2)

(6)

(I)

wherein each symbol is as defined above.

(Step 10)

In this step, compound (2) is reacted with compound (11) in the presence of a base to obtain compound (6).

Compound (11) is not particularly limited, and compound (11) synthesized by a method known per se (e.g., Romuald, C. et al., Organic Letters, 2013, 15(1), 184-187) can be preferably used.

The amount of compound (11) to be used is generally 1 to mol, preferably 2 to 3 mol, per 1 mol of compound (2).

The base to be used is not particularly limited, and examples thereof include organic bases such as triethylamine, N,N-diisopropylethylamine (DIPEA), and the like; inorganic bases such as sodium hydride and the like, and the like. Among these, sodium hydride is preferred.

The amount of the base to be used is generally 1 to 3 mol, preferably 2 mol, per 1 mol of compound (2). The reaction yield can be improved by adding crown ether (e.g., 15-crown-5-ether) as necessary.

This reaction can be carried out in a solvent that does not affect the reaction. The reaction solvent is not particularly limited, and examples thereof include ethers such as tetrahydrofuran and the like; amides such as N,N-dimethylformamide, N,N-dimethylacetamide, and the like; halogenated hydrocarbons such as dichloromethane, chloroform, and the like; dimethyl sulfoxide, and the like. Among these, N,N-dimethylformamide is preferred.

The reaction temperature is generally −10° C. to 60° C., preferably 0° C. to 40° C., more preferably 0° C. to room temperature, and the reaction time is generally about 1 hr to 24 hr.

Compound (I) can be produced by subjecting compound (6) obtained in step 10 to the aforementioned steps 5 to 9.

Production Method 3

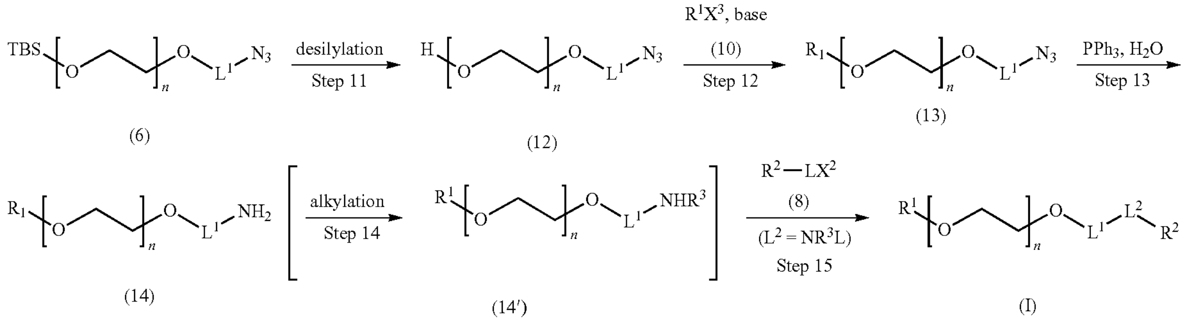

wherein each symbol is as defined above.

(Step 11)

In this step, compound (6) is desilylated to obtain compound (12). This step can be performed under the same conditions as in the reaction of Production method 1, step 8.

(Step 12)

In this step, compound (12) is reacted with compound (10) in the presence of a base to obtain compound (13). This step can be performed under the same conditions as in the reaction of Production method 1, step 9.

(Step 13)

In this step, compound (13) is reduced to obtain compound (14). This step can be performed under the same conditions as in the reaction of Production method 1, step 5.

(Step 14)

In this step, compound (14) is alkylated by reacting with a hydride reducing agent in the presence of aldehyde to obtain compound (14'). This step can be omitted when producing compound (I) of the formula (I) wherein $R^3$ is a hydrogen atom. This step can be performed under the same conditions as in the reaction of Production method 1, step 6.

(Step 15)

In this step, compound (14) (or compound (14')) is reacted with compound (8) to obtain compound (I). This step can be performed under the same conditions as in the reaction of Production method 1, step 7.

Production Method 4

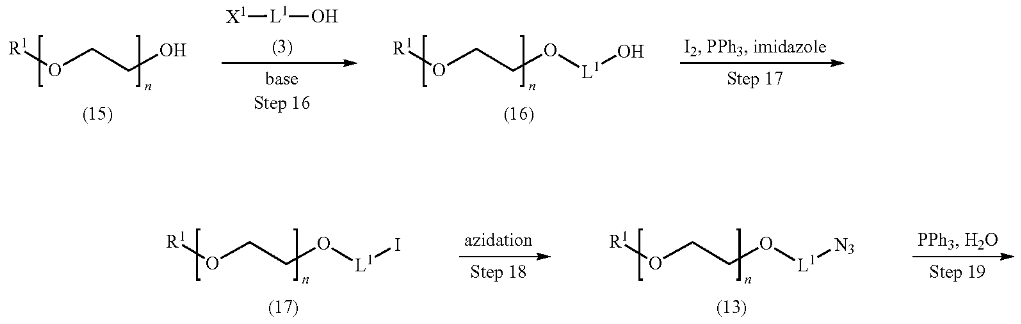

-continued

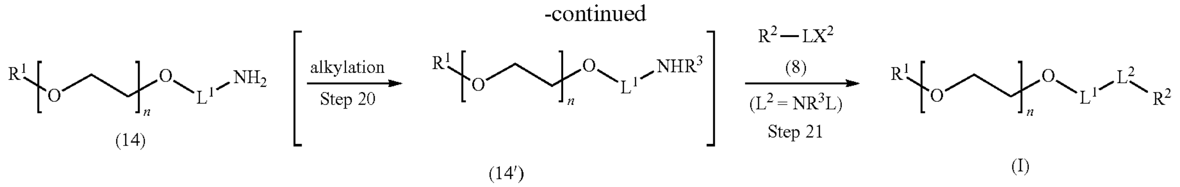

(14) (14') (I)

wherein each symbol is as defined above.

(Step 16)

In this step, compound (15) and compound (3) are reacted in the presence of a base to obtain compound (16). This step can be performed under the same conditions as in the reaction of Production method 1, step 2.

(Step 17)

In this step, compound (16) is reacted with iodine in the presence of triphenylphosphine and imidazole to obtain compound (17). This step can be performed under the same conditions as in the reaction of Production method 1, step 3.

(Step 18)

In this step, compound (17) is azidated to obtain compound (13). This step can be performed under the same conditions as in the reaction of Production method 1, step 4.

(Step 19)

In this step, compound (13) is reduced to obtain compound (14). This step can be performed under the same conditions as in the reaction of Production method 1, step 5.

(Step 20)

In this step, compound (14) is alkylated by reacting with a hydride reducing agent in the presence of aldehyde to obtain compound (14'). This step can be omitted when producing compound (I) of the formula (I) wherein $R^3$ is a hydrogen atom. This step can be performed under the same conditions as in the reaction of Production method 1, step 6.

(Step 21)

In this step, compound (14) (or compound (14')) is reacted with compound (8) to obtain compound (I). This step can be performed under the same conditions as in the reaction of Production method 1, step 7.

Production Method 5

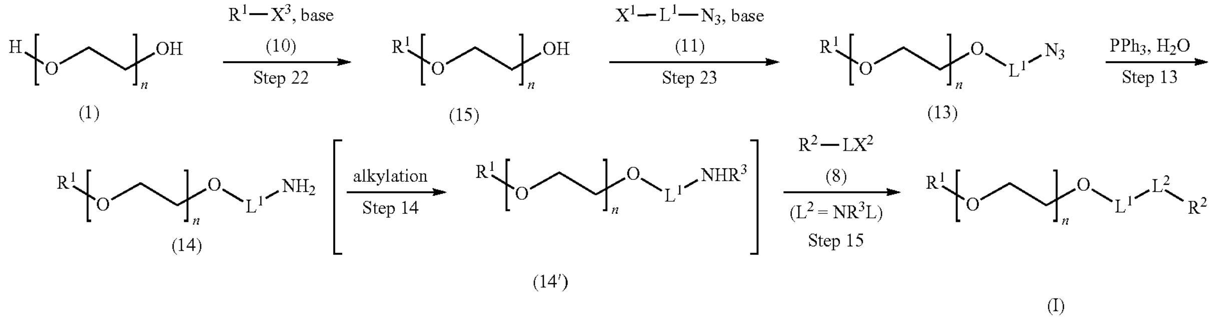

(1) (15) (13) (14) (14') (I)

wherein each symbol is as defined above.

(Step 22)

In this step, compound (1) is reacted with compound (10) in the presence of a base to obtain compound (15). This step can be performed under the same conditions as in the reaction of Production method 1, step 9. The reaction yield can be improved by adding crown ether (e.g., 15-crown-5-ether) as necessary.

(Step 23)

In this step, compound (15) is reacted with compound (11) in the presence of a base to obtain compound (13). This step can be performed under the same conditions as in the reaction of Production method 2, step 10.

(Steps 13-15)

These steps can be performed under the same conditions as in the reaction of Production method 3, steps 13-15.

Production Method 6

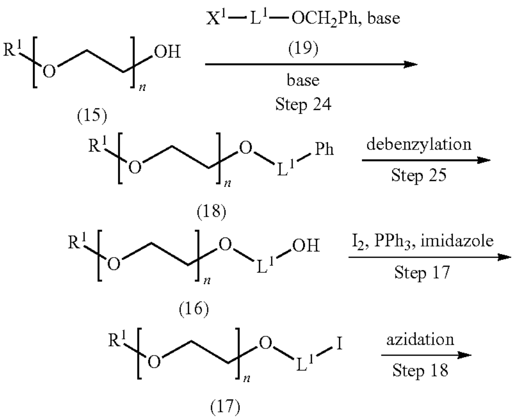

(15) (18) (16) (17)

-continued

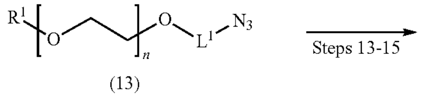

(13)

-continued

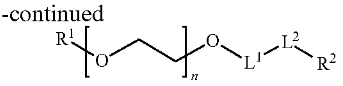

(I)

wherein $X^4$ is a leaving group and other symbols are each as defined above.

(Step 24)

In this step, compound (15) is reacted with compound (19) in the presence of a base to obtain compound (18).

Compound (19) is not particularly limited, and compound (19) synthesized by a method known per se (e.g., Lambert, T. H., et al., Org. Lett., 2013, 15(1), 38-41) can be preferably used.

The amount of compound (19) to be used is generally 1 to mol, preferably 2 to 3 mol, per 1 mol of compound (15).

The base to be used is not particularly limited, and examples thereof include organic bases such as triethylamine, N,N-diisopropylethylamine (DIPEA), and the like; inorganic bases such as sodium hydride and the like, and the like. Among them, sodium hydride is preferred.

The amount of the base to be used is generally 1 to 3 mol, preferably 2 mol, per 1 mol of compound (15). The reaction yield can be improved by adding crown ether (e.g., 15-crown-5-ether) as necessary.

This reaction can be carried out in a solvent that does not affect the reaction. The reaction solvent is not particularly limited, and examples thereof include ethers such as tetrahydrofuran and the like; amides such as N,N-dimethylformamide, N,N-dimethylacetamide, and the like; halogenated hydrocarbons such as dichloromethane, chloroform, and the like; dimethyl sulfoxide, and the like. Among them, N,N-dimethylformamide is preferred.

The reaction temperature is generally −10° C. to 60° C., preferably 0° C. to 40° C., more preferably 0° C. to room temperature, and the reaction time is generally about 1 hr to 24 hr.

(Step 25)

In this step, the benzyl group of compound (18) is removed using hydrogen in a solvent in the presence of an appropriate metal catalyst to obtain compound (16).

The metal catalyst to be used is not particularly limited, and examples thereof include heterogeneous catalysts for catalytic hydrogen reduction (e.g., 10% palladium-carbon, 10% palladium hydroxide-carbon, etc.), and the like.

This reaction can be carried out in a solvent that does not affect the reaction. The reaction solvent is not particularly limited, and examples thereof include esters such as ethyl acetate, propyl acetate, and the like; ethers such as diethyl ether, tetrahydrofuran, 1,4-dioxane, 1,2-dimethoxyethane, and the like; alcohols such as methanol, ethanol, tert-butanol, and the like; nitriles such as acetonitrile and the like; amides such as formamide, N,N-dimethylformamide, and the like; sulfoxides such as dimethyl sulfoxide and the like, and the like. Among them, ethyl acetate is preferred.

The reaction temperature is generally −10° C. to 60° C., preferably 0° C. to room temperature, and the reaction time is generally about 10 min to 48 hr.

(Steps 17-18)

These steps can be performed under the same conditions as in the reaction of Production method 4, steps 17-18.

(Steps 13-15)

These steps can be performed under the same conditions as in the reaction of Production method 3, steps 13-15.

The raw material compounds in each of the above-mentioned methods can be produced by known methods and/or in the same manner as the methods described in Examples below.

The introduction of a protecting group into a functional group and the removal of a functional group-protecting group can be carried out with reference to known methods (PROTECTIVE GROUPS in ORGANIC SYNTHESIS (written by Theodora W. Greene, Peter G. M. Wuts) etc.).

Compound (I) of the present invention produced as described above is isolated and purified in its free form or as a salt thereof. Salts can be produced by subjecting the compound to a salt-forming treatment used generally. Isolation and purification can be performed by applying general chemical operations such as extraction, concentration, crystallization, filtration, recrystallization, various chromatographies, and the like.

When compound (I) or a pharmaceutically acceptable salt thereof of the present invention exists as an optical isomer based on an asymmetric carbon, compound (I) or a pharmaceutically acceptable salt thereof of the present invention can be separated into an individual optical isomer by conventional optical resolution means (for example, fractional crystallization methods, resolution methods using chiral columns). An optically pure starting material can also be used to synthesize an optical isomer. Furthermore, an optical isomer can also be synthesized by performing each reaction stereoselectively using an asymmetric auxiliary group or an asymmetric catalyst.

When compound (I) or a pharmaceutically acceptable salt thereof of the present invention contains an optical isomer, a stereoisomer, a regioisomer, a rotamer, or a tautomer, all these isomers and mixtures of these isomers in any ratio are included as compound (I). Furthermore, each of these isomers can be obtained as a single product by a publicly known synthetic technique and separation technique (concentration, solvent extraction, column chromatography, recrystallization, and the like). When an optical isomer exists in compound (I), the optical isomer resolved from the compound is also included in compound (I). Compound (I) of the present invention also includes a labeled substance, that is, a compound in which one or two or more atoms constituting compound (I) of the present invention are labeled with an isotope (e.g., $^{2}H$, $^{3}H$, $^{11}C$, $^{13}C$, $^{14}C$, $^{15}N$, $^{18}O$, $^{18}F$, $^{35}S$, etc.).

Compound (I) or a pharmaceutically acceptable salt thereof of the present invention may be a crystal, and is encompassed in compound (I) whether it is a single crystalline form or a mixture of crystalline forms. Crystals can be produced by crystallization using crystallization methods known per se.

Compound (I) or a pharmaceutically acceptable salt thereof of the present invention may also include a solvate thereof. The solvate thereof is formed by coordinating a molecule of a solvent to compound (I) or a salt thereof, and includes hydrates. Examples thereof include hydrate, ethanolate, dimethylsulfoxide solvate, and the like.

Compound (I) of the present invention may be a prodrug.

The prodrug of compound (I) of the present invention refers to a compound that is converted to compound (I) by a reaction using an enzyme, gastric acid, or the like in the body. Prodrugs of compound (I) are considered monoesters or diesters of phosphate groups, wherein the ester functional group is preferably readily hydrolyzed or metabolized after administration to a patient. Specific examples of ester functional groups of such prodrugs include, for example, $C_{1-6}$ alkyl esters optionally substituted by acyloxy groups, phenyl esters, benzyl esters, and the like (see Bioorganic Chemistry, 1984; 12: p. 118 see-129). Furthermore, prodrugs other than the monoester or diester of a phosphate group include, for example, compounds having phosphate-derived groups, and the like described in Current opinion in investigational drugs, 2006; 7: p. 109-117, J. Med. Chem. 1994; 37: p. 1857-1864, and J. Med. Chem. 2000; 43: p. 4570-4574. Another aspect of the prodrug of compound (I) includes, for example, when compound (I) has an amino group, a compound wherein the amino group of compound (I) is acylated, alkylated, or phosphorylated (e.g., compounds wherein the amino group of compound (I) is eicosanoylated, alanylated, pentylaminoylated, (5-methyl-2-oxo-1,3-dioxollen-4-yl) methoxycarbonylated, tetrahydrofuranylated, pyrrolidylmethylated, pivaloyloxymethylated, acetoxymethylated, or tert-butylated, and the like); when compound (I) has a hydroxy group, a compound wherein the hydroxy group of compound (I) is acylated, alkylated, phosphorylated, or borylated (e.g., compounds wherein the hydroxy group of compound (I) is acetylated, palmitoylated, propanoylated, pivaloylated, succinylated, fumarylated, alanylated, or dimethylaminomethylcarbonylated, and the like); and when compound (I) has a carboxy group, a compound wherein the carboxy group of compound (I) is esterified or amidated (e.g., compounds wherein the carboxy group of compound (I) is ethyl-esterified, phenyl-esterified, carboxymethyl-esterified, dimethylaminomethyl-esterified, pivaloyloxymethyl-esterified, 1-{(ethoxycarbonyl)oxy}ethyl-esterified, phthalidyl-esterified, (5-methyl-2-oxo-1,3-dioxollen-4-yl) methyl-esterified, 1-{[(cyclohexyloxy)carbonyl]oxy}ethyl-esterified, or methylamidated, and the like). These compounds can be produced by methods known per se. Furthermore, the prodrug of compound (I) may be either a hydrate or a non-hydrate. The prodrug of compound (I) may also be one that transforms into the compound represented by compound (I) under physiological conditions as described in "Development of Pharmaceuticals" Vol. 7, "Molecular Design", page 163-198, published by Hirokawa, 1990.

Medicament of the Present Invention

The medicament of the present invention is a medicament for the prophylaxis and/or treatment of diseases caused by decreased activity of AMP-activated protein kinase, and containing, as an active ingredient, compound (I) or a pharmaceutically acceptable salt thereof, or an AMP-activated protein kinase activator composed of compound (I) or a pharmaceutically acceptable salt thereof.

The medicament of the present invention may be either a medicament composed only of compound (I) or a pharmaceutically acceptable salt thereof (or an AMP-activated protein kinase activator consisting of compound (I) or a pharmaceutically acceptable salt thereof), or a pharmaceutical composition containing compound (I) or a pharmaceutically acceptable salt thereof and a pharmaceutically acceptable carrier and the like. A prophylactically effective amount or a therapeutically effective amount of the medicament of the present invention can be administered to a subject (e.g., mouse, rat, hamster, rabbit, cat, dog, cow, sheep, monkey, human, etc.).

Examples of the pharmaceutically acceptable carrier include excipient (e.g., starch, lactose, sugar, calcium carbonate, calcium phosphate, etc.), binder (e.g., starch, gum arabic, carboxymethylcellulose, hydroxypropylcellulose, crystalline cellulose, etc.), lubricant (e.g., magnesium stearate, talc, etc.), disintegrant (e.g., carboxymethylcellulose, talc, etc.), solvent (e.g., water for injection, physiological saline, Ringer's solution, alcohol, propylene glycol, polyethylene glycol, sesame oil, corn oil, olive oil, cottonseed oil, etc.), solubilizing agent (e.g., polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate, etc.), suspending agent (e.g., surfactants such as stearyltriethanolamine, sodium lauryl sulfate, lauryl aminopropionic acid, lecithin, benzalkonium chloride, benzethonium chloride, glycerin monostearate, and the like; hydrophilic polymers such as poly(vinyl alcohol), polyvinylpyrrolidone, sodium carboxymethylcellulose, methylcellulose, hydroxymethylcellulose, hydroxyethylcellulose, hydroxypropylcellulose, and the like; polysorbates, polyoxyethylene hydrogenated castor oil, etc.), isotonic agent (e.g., sodium chloride, glycerol, D-mannitol, D-sorbitol, glucose, etc.), buffering agent (e.g., buffers of phosphate, acetate, carbonate, citrate, or the like, etc.), soothing agent (e.g., benzyl alcohol, etc.), antiseptic (e.g., p-hydroxybenzoic acid esters, chlorobutanol, benzyl alcohol, phenethyl alcohol, dehydroacetic acid, sorbic acid, etc.), antioxidant (e.g., sulfite, ascorbate, etc.), colorant (e.g., water-soluble edible tar dye (e.g., edible dyes such as Food Color Red Nos. 2 and 3, Food Color yellow Nos. 4 and 5, Food Color Blue Nos. 1 and 2, and the like), water insoluble lake dyes (e.g., aluminum salt of the aforementioned water-soluble edible tar dye), natural dye (e.g., β-carotene, chlorophyll, red iron oxide), etc.), sweetening agent (e.g., sodium saccharin, dipotassium glycyrrhizinate, aspartame, stevia, etc.), and the like.

The medicament (pharmaceutical composition) of the present invention can be prepared by mixing the above-mentioned components and then converting the mixture into preparations for oral administration such as tablets, fine granules, granules, capsules, dry syrup, and the like, or for parenteral administration such as injection (e.g., subcutaneous injection, intravenous injection, intramuscular injection, intraperitoneal injection, drip transfusion, etc.), external preparation (e.g., transdermal absorption type preparation, ointment, lotion, adhesive preparation), suppository (e.g., rectal suppository, vaginal suppository), pellet, nasal preparations, pulmonary preparation (inhalant), eye drop, implant, microcapsule, liposomal preparation, and the like.

As the medicament of the present invention, preparations for oral administration such as tablets are preferred.

The content of compound (I) or a pharmaceutically acceptable salt thereof of the present invention in the medicament (pharmaceutical composition) of the present invention varies depending on the form of the preparation. It is generally within the range of about 0.01 to 100 wt %, preferably about 0.1 to 50 wt %, further preferably about 0.5 to 20 wt %, with respect to the entire preparation.

The dose of compound (I) or a pharmaceutically acceptable salt thereof of the present invention can be appropriately selected according to the subject to be administered (the age, body weight, general health status, gender, severity of medical condition, and the like of the subject), administration route, type of disease, and the like. The daily dose of compound (I) or a pharmaceutically acceptable salt thereof is, for example, in the case of human and orally administered to an adult patient (body weight about 60 kg), usually in terms of compound (I) which is the active ingredient 0.001 mg to 500 mg, preferably 0.01 mg to 100 mg, can be administered in portions from one to several times daily, and the administration period is not particularly limited whether before meal, after meal, or between meal.

The above-mentioned "diseases caused by decreased activity of AMP-activated protein kinase" means a disease that is developed or exacerbated due to a decrease in the activity of AMP-activated protein kinase, and specific examples thereof include diabetes, obesity, cancer, and the like. Among these, it is particularly effective for the prophylaxis or treatment of cancer (e.g., solid tumor such as glioblastoma, gastric cancer, colon cancer, lung cancer, breast cancer, germ cell cancer, liver cancer, skin cancer, bladder cancer, prostate cancer, uterine cancer, cervical cancer, ovarian cancer, and the like).

Compound (I) or a pharmaceutically acceptable salt thereof of the present invention can be used in combination with other drugs (concomitant drugs), such as existing anticancer agents and the like, as long as the drug efficacy thereof is not impaired. In this case, the timing of administration is not limited, and these drugs may be simultaneously administered to the subject, or may be administered at different times. Furthermore, compound (I) of the present invention and a concomitant drug can also be administered as a single preparation containing them in combination.

The dose of the concomitant drug can be appropriately selected based on the dose used clinically. In addition, the compounding ratio of compound (I) or a pharmaceutically acceptable salt thereof of the present invention and a concomitant drug can be appropriately selected depending on the subject of administration, administration route, the type of disease, symptoms, the kind of concomitant drug, and the like.

When compound (I) or a pharmaceutically acceptable salt thereof of the present invention is used for the treatment and/or prophylaxis of cancer, concomitant drugs include, for example, chemotherapeutic agent, hormone therapeutic agent, molecular targeting agent (epidermal growth factor receptor (EGFR) tyrosine kinase inhibitor), antibody-drug conjugate (ADC) targeting cancer cells, and oncolytic virus preparation.

As the "chemotherapeutic agent", for example, alkylating agent, antimetabolite, antitumor antibiotic, plant-derived antitumor drug, or the like is used.

As the "alkylating agent", for example, nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, or the like is used.

As the "antimetabolite", for example, mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofour, gallocitabine, emitefur, capecitabine), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, or the like is used.

As the "antitumor antibiotics", for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparation thereof, or the like is used.

As the "plant-derived antitumor drug", for example, camptothecin, irinotecan, etoposide, etoposide phosphate, vinblastine sulfate, vincristine sulfate, vindesine sulfate, teniposide, paclitaxel, docetaxel, vinorelbine, DDS preparation thereof, or the like is used.

As the "hormone therapeutic agent", for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testrolactone, aminoglutethimide, LH-RH agonist (e.g., goserelin acetate, buserelin, leuprorelin), droloxifene, epitiostanol, ethinylestradiol sulfonate, aromatase inhibitor (e.g., fadrozole hydrochloride, anastrozole, letrozole, exemestane, vorozole, formestane), anti-androgen (e.g., flutamide, bicartamide, nilutamide), 5α-reductase inhibitor (e.g., finasteride, epristeride), adrenocortical hormone drug (e.g., dexamethasone, predonisolone, betamethasone, triamcinolone), androgen synthesis inhibitor (e.g., abiraterone), retinoid and a drug that retards retinoid metabolism (e.g., liarozole), DDS preparation thereof, or the like is used.

As the "molecular targeting agent", for example, tositumomab, ibritumomab, alemtuzumab, axitinib, bevacizumab, afacinib, bortezomib, bosutinib, carfilzomib, cetuximab, dasatinib, denosumab, edrecolomab, erlotinib, everolimus, vismodegib, gefitinib, gemtuzumab ozogamicin, imatinib, ipirimumab, lapatinib, lenalidomide, nilotinib, nimotuzumab, olaparib, panitumumab, pazopanib, pertuzumab, rituximab, siltuximab, sorafenib, sunitinib, tamibarotene, temsirolimus, thalidomide, trastuzumab, tretinoin, vandetanib, vorinostat, cabozantinib, trametinib, dabrafenib, alectinib, celitinib, ibrutinib, palbociclib, legolafenib, pilaralisib, DDS preparation thereof, or the like is used.

As the antibody-drug conjugate (ADC) that targets cancer cells, for example, trastuzumab deruxtecan (DS-8201), DDS formulation thereof, and the like are used.

As the oncolytic virus preparation, for example, telomelysin, DDS preparation thereof, and the like are used.

In addition, examples of the concomitant drug when compound (I) or a pharmaceutically acceptable salt thereof of the present invention is used for the treatment and/or prophylaxis of diabetes or obesity include insulin sensitizers, HMG-CoA reductase inhibitors, angiotensin II receptor antagonists, therapeutic drugs for non-statin hypercholesterolemia, antioxidants, and the like.

As the "insulin sensitizer", for example, thiazolidine derivatives (e.g., pioglitazone hydrochloride, troglitazone, rosiglitazone or maleate thereof, GI-262570, JTT-501, MCC-555, YM-440, KRP-297, CS-011, FK-614, NN-622, AZ-242, BMS-298585, ONO-5816, LM-4156, BM-13-1258, MBX-102, GW-1536, etc.), biguanides (e.g., phenformin, metformin, buformin, etc.), and the like are used.

As the "HMG-CoA reductase inhibitor", for example, pravastatin, simvastatin, lovastatin, atorvastatin, fluvastatin, lipantil, cerivastatin, itavastatin, rosuvastatin, a salt thereof (e.g., sodium salt, etc.), and the like are used.

As the "angiotensin II receptor antagonist", for example, candesartan cilexetil, losartan, eprosartan, valsartan, telmisartan, irbesartan, tasosartan, and the like are used.

As the "therapeutic drug for non-statin hypercholesterolemia", for example, ezetimibe and the like are used.

As the "antioxidant", for example, vitamin E, betaine, pentoxifylline, N-acetyl-L-cysteine, and the like are used.

When a concomitant drug is used, the administration time is not limited, and these drugs may be administered to the subject to be administered simultaneously or at intervals of time. Administration by time differences may be performed by administering the medicament of the present invention first and administering the concomitant drug later, or by administering the concomitant drug first and administering the medicament of the present invention later. Each mode of administration may be the same or different. It is also possible to administer a single preparation containing compound (I) or a pharmaceutically acceptable salt thereof of the present invention in combination with a concomitant drug.

The dose of the concomitant drug can be appropriately selected based on clinically used doses. In addition, the compounding ratio of the compound or a pharmaceutically acceptable salt thereof of the present invention and the concomitant drug can be appropriately selected according to the subject to be administered (the age, body weight, general health, gender, severity of medical condition, and the like of the subject), route of administration, type of disease, kind of concomitant drug, and the like.

The mass ratio of compound (I) or a pharmaceutically acceptable salt thereof to the concomitant drug is not particularly limited.

Furthermore, concomitant drugs that complement and/or enhance the therapeutic effect of compound (I) or a pharmaceutically acceptable salt thereof also include those that have not been found to date but will be found in the future, based on the mechanisms described above.

The medicament or pharmaceutical composition of the present invention may be provided in the form of a kit together with instructions for the mode of administration. The medicament contained in the kit is supplied by a container made of a material that effectively maintains the activity of the components of the medicament or pharmaceutical composition for a long period of time, does not adsorb to the inside of the container, and does not alter the components. For example, a sealed glass ampoule may include a buffer or the like encapsulated in the presence of a neutral and inert gas such as nitrogen gas. Instructions for use may also be attached to the kit. Instructions for use in the present kit may be printed on paper or the like, or may be stored on an electromagnetically readable medium such as CD-ROM, DVD-ROM, or the like and supplied to the user.

EXAMPLE

The present invention is described in detail below based on Reference Examples, Examples, Experimental Examples, and Formulation Examples. However, the present invention is not limited by the Examples and Experimental Examples, and may be modified without departing from the scope of the present invention. Furthermore, the reagents, devices, and materials used in the present invention are commercially available unless otherwise specified.

% indicates mol/mol % for yield, and indicates weight % for others unless otherwise specified. In addition, room temperature refers to a temperature of 15° C. to 30° C. unless otherwise specified. Other abbreviations used in the text have the following meanings.

s: singlet
d: doublet
t: triplet
q: quartet
qn: quintet
m: multiplet
br: broad
dd: double doublet
td: triple doublet
dt: double triplet
tt: triple triplet
J: coupling constant
$CDCl_3$: deuterochloroform
HRMS: high resolution mass spectrometry
FAB: fast atomic bombardment method
EI: electron impact ionization method
ESI: electrospray ionization method
CI: chemical ionization method
IR (ATR): infrared spectroscopy (total reflection measurement method)
TBS: tert-butyldimethylsilyl
DMF: N,N-dimethylformamide
EDC: 1-ethyl-3-(3-dimethylaminopropyl)carbodiimide hydrochloride
DMAP: N, N-dimethyl-4-aminopyridine
THF: tetrahydrofuran
DIAD: diisopropyl azodicarboxylate
DPPA: diphenylphosphoryl azide
DIPEA: N,N-diisopropylethylamine
$PPh_3$: triphenylphosphine $^1H$ NMR and $^{13}C$ NMR spectra were measured in $CDCl_3$, with a total δ value of ppm.

The raw material compounds used in the following Examples are known compounds, and either commercially available products were used as they were, or those synthesized and identified according to methods known per se were used.

Reference Example 1

Synthesis of 12-iodo-1-dodecyne (compound (10a))

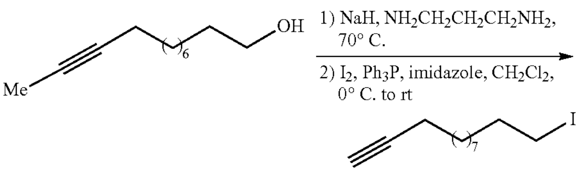

10a

Under a nitrogen atmosphere, to a solution of 10-dodecyne-1-ol (manufactured by Sigma-Aldrich Co. LLC) (1.00 g, 5.49 mmol) in 1,3-propanediamine (43 mL) was added, under ice-cooling, sodium hydride (60% in oil, 1.76 g, 43.9 mmol), and the mixture was stirred at 70° C. for 5 hr. Water was added, under ice-cooling, and the mixture was extracted with diethyl ether. The organic layer was washed with saturated brine, and dried over anhydrous magnesium sulfate. The solvent was evaporated under reduced pressure, and the residue was purified by silica gel column chromatography (n-hexane:ethyl acetate=5:1) to give 11-dodecyn-1-ol (615 mg, 62%). To a solution of triphenylphosphine (1.18 g, 4.55 mmol) in dehydrated dichloromethane (10 mL) were added, under ice-cooling, imidazole (306 mg, 4.55 mmol) and iodine (1.16 g, 4.55 mmol), and the mixture was stirred at the same temperature for 10 min. Under ice-cooling, a solution of 11-dodecyn-1-ol (615 mg, 3.37 mmol)

in dehydrated dichloromethane (7 mL) was added, and the mixture was stirred at room temperature for 20 min. Saturated aqueous sodium thiosulfate solution was added at room temperature, and the mixture was extracted with n-hexane. The organic layer was washed with saturated brine, and dried over anhydrous magnesium sulfate. The solvent was evaporated under reduced pressure, and the residue was purified by silica gel column chromatography (n-hexane:ethyl acetate=100:1) to give 12-iodo-1-dodecyne (compound (10a)) (918 mg, 93%).

$^{1}H$ NMR (400 MHz, $CDCl_3$) δ: 1.23-1.47 (m, 12H), 1.47-1.61 (m, 2H), 1.82 (qn, 2H, J=7.1 Hz), 1.95 (t, 1H, J=2.5 Hz), 2.18 (td, 2H, J=7.1, 2.6 Hz), 3.19 (t, 2H, J=7.1 Hz).

Reference Example 2

Synthesis of 11-iodo-1-undecyne (compound (10b))

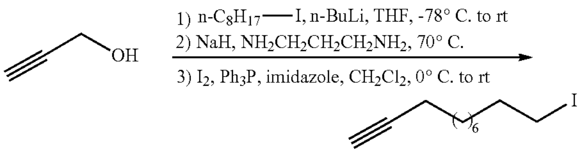

10b

Under a nitrogen atmosphere, to a solution of propargyl alcohol (manufactured by Tokyo Chemical Industry Co., Ltd.) (1.00 g, 17.8 mmol) in dehydrated tetrahydrofuran (59.5 mL) was added, at −78° C., n-butyllithium (2.6 M n-hexane solution, 13.7 mL, 35.7 mmol), and the mixture was stirred at the same temperature for 1 hr. 1-Iodooctane (6.44 mL, 35.7 mmol) was added at −78° C., and the mixture was stirred at room temperature for 18 hr. Saturated aqueous ammonium chloride solution was added at room temperature, and the mixture was extracted with ethyl acetate. The organic layer was washed with saturated brine, and dried over anhydrous magnesium sulfate. The solvent was evaporated under reduced pressure, and the residue was purified by silica gel column chromatography (n-hexane:ethyl acetate=30:1→1:1) to give 2-undecyn-1-ol (235 mg, 8%). Under a nitrogen atmosphere, to a solution of 2-undecyn-1-ol (235 mg, 1.40 mmol) in 1,3-propanediamine (4.7 mL) was added, under ice-cooling, sodium hydride (60% in oil, 446 mg, 11.2 mmol), and the mixture was stirred at 70° C. for 8 hr. After cooling to room temperature, water was added at the same temperature, and the mixture was extracted with diethyl ether. The organic layer was washed with saturated brine, and dried over anhydrous magnesium sulfate. The solvent was evaporated under reduced pressure, and the residue was purified by silica gel column chromatography (n-hexane:ethyl acetate=3:1) to give 10-undecyn-1-ol (98.0 mg, 42%). To a solution of triphenylphosphine (199 mg, 0.757 mmol) in dehydrated dichloromethane (3.82 mL) were added, under ice-cooling, imidazole (51.5 mg, 0.757 mmol) and iodine (192 mg, 0.757 mmol), and the mixture was stirred at the same temperature for 10 min. Under ice-cooling, a solution of 10-undecyn-1-ol (98.0 mg, 0.582 mmol) in dehydrated dichloromethane (2.00 mL) was added, and the mixture was stirred at room temperature for 20 min. A saturated aqueous sodium thiosulfate solution was added at room temperature, and the mixture was extracted with ethyl acetate. The organic layer was washed with saturated brine, and dried over anhydrous magnesium sulfate. The solvent was evaporated under reduced pressure, and the residue was purified by silica gel column chromatography (n-hexane) to give 11-iodo-1-undecyne (compound (10b)) (71.8 mg, 44%).

$^{1}H$ NMR (400 MHz, $CDCl_3$) δ: 1.16-1.46 (m, 10H), 1.46-1.62 (m, 4H), 1.82 (qn, 2H, J=7.1 Hz), 1.95 (t, 1H, J=2.6 Hz), 2.19 (td, 2H, J=7.0, 2.6 Hz), 3.19 (t, 2H, J=7.0 Hz).

Reference Example 3

Synthesis of 4-pentyn-1-yl p-toluenesulfonate (compound (10c))

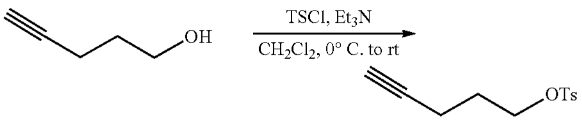

10c

Under an argon atmosphere, to a solution of 4-pentyn-1-ol (manufactured by Tokyo Chemical Industry Co., Ltd.) (2.00 g, 24.0 mmol) in dehydrated dichloromethane (47.5 mL) were added, under ice-cooling, triethylamine (3.98 mL, 28.5 mmol) and p-toluenesulfonyl chloride (5.00 g, 26.2 mmol), and the mixture was stirred at room temperature for 21 hr. To the reaction mixture was added water at room temperature, and the mixture was extracted with ethyl acetate. The organic layer was washed with saturated brine and dried over anhydrous sodium sulfate, and the solvent was evaporated under reduced pressure. The residue was purified by silica gel column chromatography (n-hexane:ethyl acetate=20:1→10:1) to give 4-pentyn-1-yl p-toluenesulfonate (compound (10c)) (5.18 g, 92%) as a colorless oil.

$^{1}H$ NMR (400 MHz, $CDCl_3$) δ: 1.77-2.00 (m, 3H), 2.26 (td, 2H, J=6.9, 2.5 Hz), 2.45 (s, 3H), 4.15 (t, 2H, J=6.1 Hz), 7.35 (d, 2H, J=8.1 Hz), 7.80 (d, 2H, J=8.1 Hz).

$^{1}H$ NMR of the synthesized compound (10c) was consistent with the data of the same compound described in non patent literature (Cheuug, F. K. et al., Org. Biomol. Chem., 2007, 5(7), 1093-1103).

Reference Example 4

Synthesis of 1-azido-12-bromododecane (compound (11a))

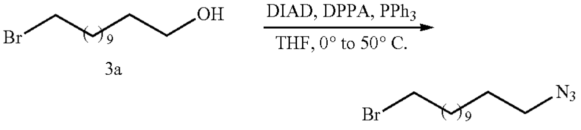

3a

11a

Under a nitrogen atmosphere, to a solution of 12-bromo-1-dodecanol (compound (3a)) (manufactured by Tokyo Chemical Industry Co., Ltd.) (2.00 g, 7.54 mmol) in dehydrated tetrahydrofuran (75.4 mL) was added, under ice-cooling, triphenylphosphine (3.96 g, 15.1 mmol), and the mixture was stirred at the same temperature for 15 min.

Under ice-cooling, diisopropyl azodicarboxylate (4.87 mL, 22.6 mmol) and diphenylphosphoryl azide (3.25 mL, 15.1 mmol) were added and the mixture was stirred at 50° C. for 15 hr. The solvent was evaporated under reduced pressure, silica gel and chloroform were added thereto, and the solvent was evaporated again under reduced pressure. The residue was purified by silica gel column chromatography (n-hexane:ethyl acetate=20:1) to give 1-azido-12-bromododecane (compound (11a)) (1.74 g, 80%) as a clear colorless oil.

$^1H$ NMR (400 MHz, $CDCl_3$) δ: 1.19-1.46 (m, 16H), 1.57-1.63 (m, 2H), 1.85 (qn, 2H, J=7.1 Hz), 3.26 (t, 2H, J=7.0 Hz), 3.41 (t, 2H, J=6.9 Hz).

$^1H$ NMR of the synthesized compound (11a) was consistent with the data of the same compound described in non patent literature (Romuald, C. et al., Organic Letters, 2013, 15(1), 184-187).

Reference Example 5

Synthesis of 1-azido-9-bromononane (compound (11b))

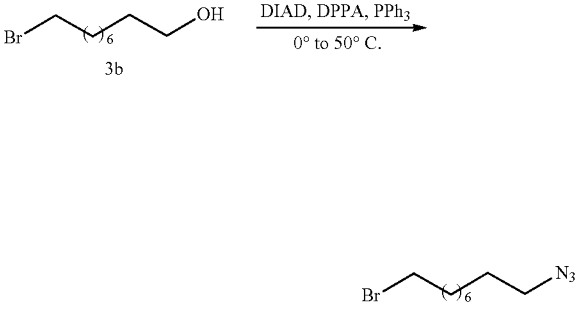

3b

11b

Under a nitrogen atmosphere, to a solution of 9-bromo-1-nonanol (compound (3b)) (manufactured by Tokyo Chemical Industry Co., Ltd.) (2.00 g, 8.96 mmol) in dehydrated tetrahydrofuran (89.6 mL) was added, under ice-cooling, triphenylphosphine (4.69 g, 17.9 mmol), and the mixture was stirred at the same temperature for 10 min. Under ice-cooling, diisopropyl azodicarboxylate (5.79 mL, 4.40 mmol) and diphenylphosphoryl azide (3.86 mL, 17.9 mmol) were added thereto, and the mixture was stirred at 50° C. for 19 hr. After evaporation of the solvent under reduced pressure, silica gel and chloroform were added, and the solvent was evaporated again under reduced pressure. The residue was purified by silica gel column chromatography (n-hexane:ethyl acetate=20:1) to give 1-azido-9-bromononane (compound (11b)) (1.71 g, 77%) as a clear colorless oil.

$^1H$ NMR (400 MHz, $CDCl_3$) δ: 1.23-1.56 (m, 10H), 1.39-1.48 (m, 2H), 1.83-1.90 (m, 2H), 3.26 (t, 2H, J=7.0 Hz), 3.41 (t, 2H, J=6.8 Hz).

$^1H$ NMR of the synthesized compound (11b) was consistent with the data of the same compound described in non patent literature (Decroocw, C. et al., Chem. Eur. J., 2011, 17(49), 13825-13831).

Reference Example 6

Synthesis of 1-methyl-1H-pyrazole-5-sulfonyl chloride (compound (8h))

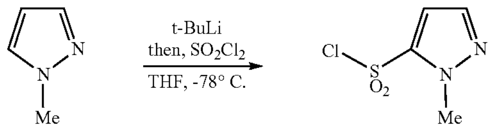

8h

To a solution of 1-methyl-1H-pyrazole (246 mg, 3.00 mmol) in dehydrated tetrahydrofuran (10.0 mL) was added t-BuLi (Kanto Chemical Co., Inc.) (1.6 M in n-pentane, 3.94 mL, 6.31 mmol) over 10 min at −78° C., and the mixture was stirred at the same temperature for 1 hr. To the reaction mixture was added sulfuryl chloride (Nacalai Tesque, Inc.) (0.362 mL, 4.50 mmol) at the same temperature, and the mixture was stirred for 1.5 hr. To the reaction mixture was added water under ice-cooling, and the mixture was extracted with diethyl ether. The organic layer was washed with saturated brine, and dried over anhydrous magnesium sulfate. The solvent was evaporated under reduced pressure. The residue was purified by silica gel column chromatography (n-hexane:ethyl acetate=20:1→10:1) to give 1-methyl-1H-pyrazole-5-sulfonyl chloride (compound (8h)) (127 mg, 24%) as a clear colorless oil.

$^1H$ NMR (500 MHz, $CDCl_3$) δ: 4.23 (s, 3H), 7.02 (d, 1H, J=1.8 Hz), 7.57 (d, 1H, J=1.8 Hz);

$^{13}C$ NMR (125 MHz, $CDCl_3$) δ: 39.0, 112.1, 137.9, 141.1;

IR (NaCl) $cm^{-1}$: 1386, 1200;

MS (EI) m/z: 182 (15.7) $[M+2]^+$, 180 (44.8) $[M]^+$, 145 (100.0);

HRMS (EI) m/z: Calcd for $C_4H_5ClN_2O_2S$: 179.9760; Found: 179.9787 $[M]^+$.

Reference Example 7

Synthesis of 1-benzyloxy-6-bromohexane (compound (19a))

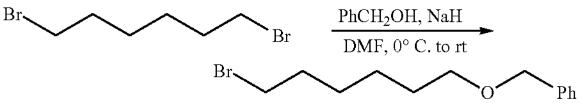

19a

Under a nitrogen atmosphere, to a solution of benzyl alcohol (0.481 mL, 4.62 mmol) in dehydrated dimethylformamide (9.2 mL) was added, under ice-cooling, sodium hydride (manufactured by Tokyo Chemical Industry Co., Ltd.) (60% in oil, 203 mg, 5.08 mmol), and the mixture was stirred at the same temperature for 20 min. 1,6-Dibromohexane (manufactured by Tokyo Chemical Industry Co., Ltd.) (3.53 mL, 23.1 mmol) was added thereto at the same temperature, and the mixture was stirred at room temperature for 21 hr. To the reaction mixture was added water at room temperature, and the mixture was extracted with ethyl acetate. The organic layer was washed with saturated brine, and dried over anhydrous magnesium sulfate, and the solvent was evaporated under reduced pressure. The residue was purified by silica gel column chromatography (n-hexane→n-hexane:ethyl acetate=200:1→50:1→10:1) to give 1-benzyloxy-6-bromohexane (compound (19a)) (734 mg, 59%) as a clear colorless oil.

$^1$H NMR (500 MHz, $CDCl_3$) δ: 1.37-1.48 (m, 4H), 1.63 (qn, 2H, J=6.9 Hz), 1.86 (qn, 2H, J=6.8 Hz), 3.40 (t, 2H, J=6.9 Hz), 3.47 (t, 2H, J=6.8 Hz), 4.50 (s, 2H), 7.26-7.36 (m, 5H).

$^1$H NMR of the synthesized compound (19a) was consistent with the data of the same compound described in non patent literature (Lambert, T. H., et al., Org. Lett., 2013, 15(1), 38-41).

Example 1

Synthesis of N-(21-hydroxy-13,16,19-trioxaheneicosan-1-yl)-thiophene-3-carboxamide (Compound (I-1))

I-1

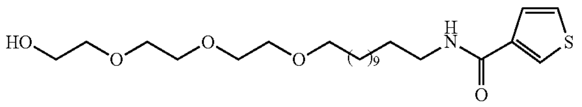

(1-1) Synthesis of 8-(t-butyldimethylsilyloxy)-3,6-dioxa-1-octanol (Compound (2a))

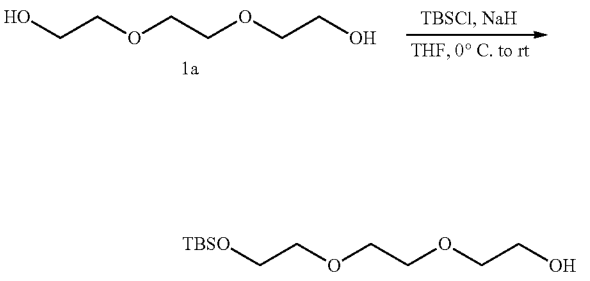

1a

2a

Under a nitrogen atmosphere, to a solution of sodium hydride (60% in oil, 1.06 g, 44.0 mmol) in dehydrated tetrahydrofuran (80.0 mL) was added, under ice-cooling, triethylene glycol (compound (1a)) (manufactured by Tokyo Chemical Industry Co., Ltd.) (5.33 mL, 40.0 mmol), and the mixture was stirred at the same temperature for 10 min. Under ice-cooling, t-butyldimethylsilyl chloride (7.23 g, 48.0 mmol) was added thereto, and the mixture was stirred at room temperature for 3 hr. To the reaction mixture was added water at room temperature, and the mixture was extracted with ethyl acetate. The organic layer was washed with saturated aqueous ammonium chloride solution and saturated brine, and dried over anhydrous magnesium sulfate. The solvent was evaporated under reduced pressure. The residue was purified by silica gel column chromatography (n-hexane:ethyl acetate=2:1→1:1) to give 8-(t-butyldimethylsilyloxy)-3,6-dioxa-1-octanol (compound (2a)) (7.06 g, 67%) as a clear colorless oil.

$^1$H NMR (400 MHz, $CDCl_3$) δ: 0.07 (s, 6H), 0.90 (s, 9H), 3.56-3.68 (m, 4H), 3.72 (s, 4H), 3.53-3.58 (m, 4H), 3.62-3.65 (m, 6H).

$^1$H NMR of the synthesized compound (2a) was consistent with the data of the same compound described in non patent literature (Lee, E. et al., ACS Catalyst, 2014, 4(10), 3590-3592).

(1-2) Synthesis of 1-azido-21-(t-butyldimethylsilyloxy)-13,16,19-trioxaheneicosane (Compound (6a))

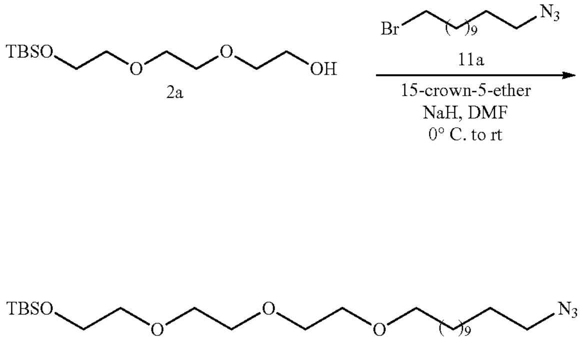

2a

11a

6a

Under a nitrogen atmosphere, to a solution of compound (2a) (500 mg, 2.00 mmol) in dehydrated dimethylformamide (0.500 mL) was added, under ice-cooling, sodium hydride (60% in oil, 95.9 mg, 4.00 mmol), and the mixture was stirred at the same temperature for 10 min. Under ice-cooling, the mixture was stirred with 15-crown-5-ether (0.800 mL, 4.00 mmol) and a solution of 1-azido-12-bromododecane (compound (11a)) (1.16 g, 4.00 mmol) in dehydrated dimethylformamide (1.50 mL) at room temperature for 23 hr. To the reaction mixture was added water under ice-cooling, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane→n-hexane:ethyl acetate=20:1→10:1) to give 1-azido-21-(t-butyldimethylsilyloxy)-13,16,19-trioxaheneicosane (compound (6a)) (586 mg, 62%) as a colorless oil.

$^1$H NMR (400 MHz, $CDCl_3$) δ: 0.05 (s, 6H), 0.88 (s, 9H), 1.25-1.60 (m, 20H), 3.24 (t, 2H, J=7.0 Hz), 3.43 (t, 2H, J=6.9 Hz), 3.53-3.58 (m, 4H), 3.62-3.65 (m, 6H), 3.75 (t, 2H, J=5.5 Hz);

$^{13}$C NMR (125 MHz, $CDCl_3$) δ: −5.24, −5.21, 18.4, 26.0 (3C), 26.2, 26.8, 28.9, 29.2, 29.56, 29.57, 29.60, 29.64, 29.70, 29.73, 51.6, 62.8, 70.2, 70.8 (2C), 70.9, 71.7, 72.8;

IR (NaCl) $cm^{-1}$: 2095;

MS (FAB) m/z: 474 $[M+H]^+$;

HRMS (FAB) m/z: Calcd for $C_{24}H_{52}N_3O_4Si$: 474.3649; Found: 474.3723 $[M+H]^+$.

(1-3) Synthesis of N-{21-(t-butyldimethylsilyloxy)-13,16,19-trioxaheneicosan-1-yl}thiophene-3-carboxamide (Compound (9a))

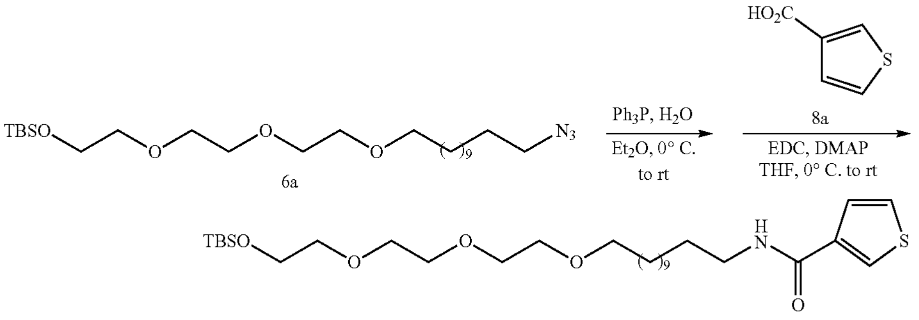

6a

9a

To a solution of compound (6a) (1.17 g, 2.47 mmol) in diethyl ether (12.4 mL) was added, under ice-cooling, triphenylphosphine (0.972 g, 3.71 mmol) and the mixture was stirred at the same temperature for 5 min. Under ice-cooling, water (12.4 mL) was added thereto, and the mixture was warmed to room temperature and stirred for 69 hr. To the reaction mixture was added, at room temperature, 6M aqueous sodium hydroxide solution to adjust the solution to pH=11, and the solution was extracted with diethyl ether and dried over anhydrous sodium sulfate. The solvent was evaporated under reduced pressure. Under an argon atmosphere, to a solution of the residue in dehydrated tetrahydrofuran (24.8 mL) were added, under ice-cooling, 3-thiophenecarboxylic acid (compound (8a)) (0.633 g, 4.94 mmol), 1-ethyl-3-(3-dimethylaminopropyl)carbodiimide hydrochloride (1.14 g, 5.93 mmol), and N,N-dimethyl-4-aminopyridine (0.664 g, 5.43 mmol), and the mixture was warmed to room temperature and stirred for 28 hr. Water was added thereto at room temperature, and the mixture was extracted with ethyl acetate. The organic layer was washed with saturated brine and dried over anhydrous sodium sulfate. The solvent was evaporated under reduced pressure. The residue was purified by silica gel column chromatography (n-hexane:ethyl acetate=5:1→3:1) to give N-{21-(t-butyldimethylsilyloxy)-13,16,19-trioxaheneicosan-1-yl}thiophene-3-carboxamide (compound (9a)) (1.22 g, 86%) as a pale-yellow solid.

M.p. 37.6° C.-39.2° C.;

$^{1}$H NMR (400 MHz, $CDCl_3$) δ: 0.06 (s, 6H), 0.89 (s, 9H), 1.26-1.40 (m, 16H), 1.54-1.63 (m, 4H), 3.41 (td, 2H, J=7.2, 6.1 Hz), 3.45 (t, 2H, J=6.9 Hz), 3.54-3.60 (m, 5H), 3.62-3.68 (m, 5H), 3.77 (t, 2H, J=5.5 Hz), 6.00 (br, 1H), 7.33 (dd, 1H, J=5.1, 3.0 Hz), 7.37 (dd, 1H, J=5.1, 1.4 Hz), 7.84 (dd, 1H, J=3.0, 1.4 Hz);

$^{13}$C NMR (100 MHz, $CDCl_3$) δ: −5.4 (2C), 18.2, 25.8 (3C), 26.0, 26.9, 29.2, 29.35, 29.43 (4C), 29.5, 29.6, 39.7, 62.6, 70.0, 70.5 (2C), 70.6, 71.4, 72.5, 126.1 (2C), 127.8, 137.7, 163.0;

IR (NaCl) $cm^{-1}$: 3326, 1625;

MS (EI) m/z (%): 557 (5.9) $[M]^+$, 294 (49.9), 111 (90.0);

HRMS (EI) m/z: Calcd for $C_{29}H_{55}NO_5SSi$: 557.3570; Found: 557.3584 $[M]^+$.

(1-4) Synthesis of Compound (I-1))

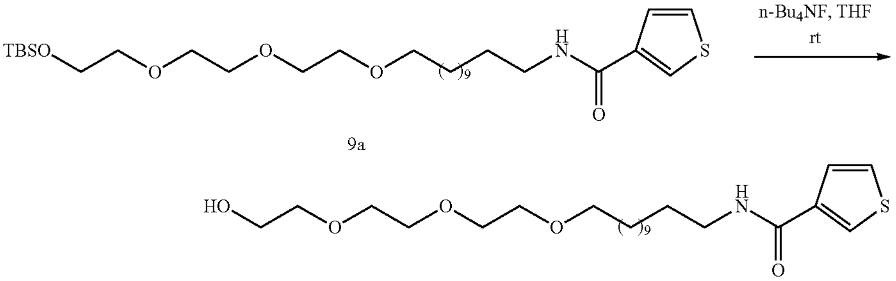

9a

I-1

Under a nitrogen atmosphere, to a solution of compound (9a) (0.253 g, 0.442 mmol) in dehydrated tetrahydrofuran (4.40 mL) was added, at room temperature, n-tetrabutylammonium fluoride (4.38 mL, 4.38 mmol, about 1.00M tetrahydrofuran solution) and the mixture was stirred at the same temperature for 1 hr. To the reaction mixture was added, at room temperature, saturated aqueous ammonium chloride solution (4.40 mL), and the mixture was extracted with ethyl acetate and dried over anhydrous sodium sulfate. The solvent was evaporated under reduced pressure. The residue was purified by silica gel column chromatography (n-hexane:ethyl acetate=1:3→ethyl acetate) to give the title compound (compound (I-1)) (0.193 g, 98%) as a white solid.

M.p. 58.4° C.-60.4° C.;

$^1H$ NMR (400 MHz, $CDCl_3$) δ: 1.21-1.42 (m, 16H), 1.53-1.67 (m, 4H), 2.61 (t, 1H, J=6.2 Hz), 3.42 (q, 2H, J=6.7 Hz), 3.45 (t, 2H, J=6.8 Hz), 3.57-3.75 (m, 12H), 5.96 (br, 1H), 7.34 (dd, 1H, J=5.0, 2.9 Hz), 7.36 (dd, 1H, J=5.0, 1.1 Hz), 7.84 (dd, 1H, J=2.9, 1.1 Hz);

$^{13}C$ NMR (100 MHz, $CDCl_3$) δ: 25.9 (2C), 26.9 (2C), 29.2, 29.3, 29.4 (3C), 29.6, 39.6, 61.6, 69.9, 70.2, 70.5, 71.5, 72.4 (2C), 126.0, 126.2, 127.8, 137.7, 163.1;

IR (ATR) $cm^{-1}$: 3326, 1623;

MS (EI) m/z (%): 443 (17.6) $[M]^+$, 310 (65.2), 294 (47.7), 111 (100.0);

HRMS (EI) m/z: Calcd for $C_{23}H_{41}NO_5S$: 443.2705; Found: 443.2703 $[M]^+$.

Example 2

Synthesis of N-(13,16,19,22-tetraoxapentacosan-1-yl)thiophene-3-carboxamide (Compound (I-2))

I-2

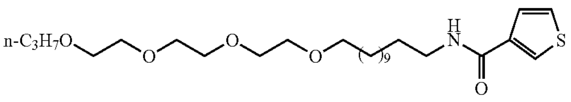

Under a nitrogen atmosphere, to a solution of compound (I-1) (50.0 mg, 0.113 mmol) in dehydrated dimethylformamide (3.00 mL) was added, under ice-cooling, sodium hydride (60% in oil, 22.6 mg, 0.939 mmol) and the mixture was warmed to room temperature and stirred for 10 min. 1-Iodopropane (compound (10d)) (manufactured by Tokyo Chemical Industry Co., Ltd.) (32.8 μL, 0.338 mmol) was added thereto at room temperature, and the mixture was stirred at the same temperature for 19 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=5:1→ethyl acetate) to give the title compound (compound (I-2)) (42.0 mg, 77%) as a pale-yellow solid.

M.p. 40.7° C.-42.5° C.;

$^1H$ NMR (400 MHz, $CDCl_3$) δ: 0.91 (t, J=7.5 Hz, 3H), 1.26-1.33 (m, 16H), 1.52-1.65 (m, 6H), 3.39-3.46 (m, 2H), 3.42 (t, 4H, J=6.9 Hz), 3.56-3.61 (m, 4H), 3.63-3.67 (m, 8H), 5.93 (br, 1H), 7.34 (dd, 1H, J=5.0, 2.8 Hz), 7.37 (dd, 1H, J=5.0, 1.5 Hz), 7.84 (dd, 1H, J=2.8, 1.5 Hz);

$^{13}C$ NMR (100 MHz, $CDCl_3$) δ: 10.4, 25.9 (2C), 26.9, 29.2, 29.3 (2C), 29.4 (2C), 29.5 (2C), 29.6, 39.7, 69.88, 69.89 (2C), 70.46, 70.47, 71.4, 72.9 (2C), 126.1 (20), 127.8, 137.7, 163.0;

IR (ATR) $cm^{-1}$: 3326, 1624;

MS (EI) m/z (%): 485 (16.6) $[M]^+$, 310 (61.4), 294 (50.6), 111 (100.0);

HRMS (EI) m/z: Calcd for $C_{26}H_{47}NO_5S$: 485.3175; Found: 485.3171 $[M]^+$.

Example 3

Synthesis of N-(13,16,19,22-tetraoxaoctacosan-1-yl)thiophene-3-carboxamide (Compound (I-3))

I-3

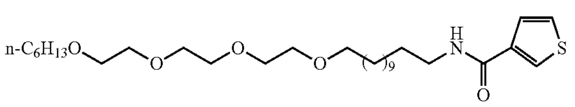

Under a nitrogen atmosphere, to a solution of compound (I-1) (200 mg, 0.451 mmol) in dehydrated dimethylformamide (12.0 mL) was added, under ice-cooling, sodium hydride (60% in oil, 90.2 mg, 3.76 mmol) and the mixture was warmed to room temperature and stirred for 10 min. 1-Iodohexane (compound (10e)) (manufactured by Tokyo Chemical Industry Co., Ltd.) (0.200 mL, 1.35 mmol) was added thereto at room temperature, and the mixture was stirred at the same temperature for 19 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=5:1→ethyl acetate) to give the title compound (compound (I-3)) (0.200 g, 84%) as a pale-yellow solid.

M.p. 47.4° C.-48.3° C.;

$^1H$ NMR (300 MHz, $CDCl_3$) δ: 0.87 (t, 3H, J=6.9 Hz), 1.18-1.41 (m, 22H), 1.53-1.62 (m, 6H), 3.38-3.45 (m, 2H), 3.45 (t, 4H, J=6.8 Hz), 3.56-3.66 (m, 12H), 5.93 (br, 1H), 7.33 (dd, 1H, J=5.1, 2.9 Hz), 7.37 (dd, 1H, J=5.1, 1.4 Hz), 7.84 (dd, 1H, J=2.9, 1.4 Hz);

$^{13}C$ NMR (100 MHz, $CDCl_3$) δ: 13.9, 22.5 (2C), 25.6, 25.9, 26.9, 29.2 (2C), 29.3 (2C), 29.4 (2C), 29.5, 29.6, 31.5, 39.7, 69.9 (2C), 70.4 (2C), 70.5 (2C), 71.4 (2C), 126.0, 126.1, 127.8, 137.7, 163.0;

IR (ATR) $cm^{-1}$: 3333, 1623;

MS (EI) m/z (%): 527 (18.4) $[M]^+$, 310 (66.6), 294 (51.2), 111 (100.0);

HRMS (EI) m/z: Calcd for $C_{29}H_{53}NO_5S$: 527.3644; Found: 527.3642 $[M]^+$.

Example 4

Synthesis of N-(13,16,19,22-tetraoxahentriacontan-1-yl)thiophene-3-carboxamide (Compound (I-4))

I-4

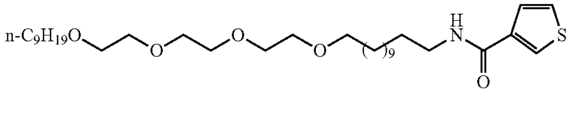

Under a nitrogen atmosphere, to a solution of compound (I-1) (50.0 mg, 0.113 mmol) in dehydrated dimethylformamide (12.0 mL) was added, under ice-cooling, sodium hydride (60% in oil, 22.6 mg, 0.939 mmol) and the mixture was warmed to room temperature and stirred for 10 min. 1-Iodononane (compound (10f)) (manufactured by Tokyo Chemical Industry Co., Ltd.) (66.6 μL, 0.338 mmol) was added thereto at room temperature, and the mixture was stirred at the same temperature for 19 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=5: 1→ethyl acetate) to give the title compound (compound (I-4)) (44.4 mg, 69%) as a pale-yellow solid.

M.p. 55.8° C.-56.9° C.;

$^1$H NMR (400 MHz, $CDCl_3$) δ: 0.88 (t, 3H, J=6.8 Hz), 1.26-1.33 (m, 28H), 1.54-1.61 (m, 6H), 3.40 (q, 2H, J=6.9 Hz), 3.44 (t, 4H, J=6.8 Hz), 3.56-3.60 (m, 4H), 3.63-3.66 (m, 8H), 5.93 (br, 1H), 7.34 (dd, 1H, J=5.0, 2.9 Hz), 7.36 (dd, 1H, J=5.0, 1.1 Hz), 7.84 (dd, 1H, J=2.9, 1.1 Hz);

$^{13}$C NMR (100 MHz, $CDCl_3$) δ: 14.0, 22.5, 25.9 (2C), 26.9, 29.1 (2C), 29.2 (2C), 29.3 (2C), 29.4, 29.5 (2C), 29.6 (2C), 31.7 (2C), 39.7, 69.9 (2C), 70.4 (4C), 71.4 (2C), 126.0, 126.1, 127.8, 137.7, 163.0;

IR (ATR) $cm^{-1}$: 3332, 1623;

MS (EI) m/z (%): 569 (28.0) $[M]^+$, 310 (89.0), 294 (74.1), 111 (100.0);

HRMS (EI) m/z: Calcd for $C_{32}H_{59}NO_5S$: 569.4114; Found: 569.4109 $[M]^+$.

Example 5

Synthesis of N-(13,16,19,22-tetraoxadotriacontan-1-yl)thiophene-3-carboxamide (compound (I-5))

I-5

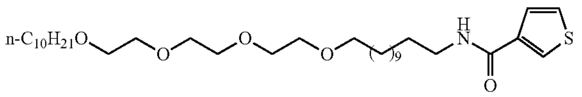

Under a nitrogen atmosphere, to a solution of compound (I-1) (50.0 mg, 0.113 mmol) in dehydrated dimethylformamide (3.00 mL) was added, under ice-cooling, sodium hydride (60% in oil, 22.6 mg, 0.939 mmol) and the mixture was warmed to room temperature and stirred for 10 min. 1-Iododecane (compound (10 g)) (manufactured by Tokyo Chemical Industry Co., Ltd.) (75.5 μL, 0.338 mmol) was added thereto at room temperature, and the mixture was stirred at the same temperature for 19 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=5: 1→1:3) to give the title compound (compound (I-5)) (38.9 mg, 59%) as a pale-yellow solid.

M.p. 60.0° C.-62.0° C.;

$^1$H NMR (300 MHz, $CDCl_3$) δ: 0.87 (t, 3H, J=6.8 Hz), 1.26-1.33 (m, 30H), 1.53-1.62 (m, 6H), 3.38-3.44 (m, 2H), 3.44 (t, 4H, J=6.8 Hz), 3.56-3.66 (m, 12H), 5.92 (br, 1H), 7.33 (dd, 1H, J=5.1, 2.9 Hz), 7.36 (dd, 1H, J=5.1, 1.4 Hz), 7.84 (dd, 1H, J=2.9, 1.4 Hz);

$^{13}$C NMR (100 MHz, $CDCl_3$) δ: 14.0, 22.6 (2C), 26.0 (2C), 26.9 (2C), 29.2 (3C), 29.37 (2C), 29.44 (2C), 29.5, 29.6 (2C), 31.8 (2C), 39.7, 69.9 (2C), 70.47 (2C), 70.48 (2C), 71.4 (2C), 126.1 (2C), 127.8, 137.7, 163.0;

IR (ATR) $cm^{-1}$: 3334, 1622;

MS (EI) m/z (%): 583 (24.4) $[M]^+$, 310 (81.9), 294 (66.6), 111 (100.0);

HRMS (EI) m/z: Calcd for $C_{33}H_{61}NO_5S$: 583.4270; Found: 583.4264 $[M]^+$.

Example 6

Synthesis of N-(13,16,19,22-tetraoxa-33-tetratriacontyn-1-yl)thiophene-3-carboxamide (compound (I-6))

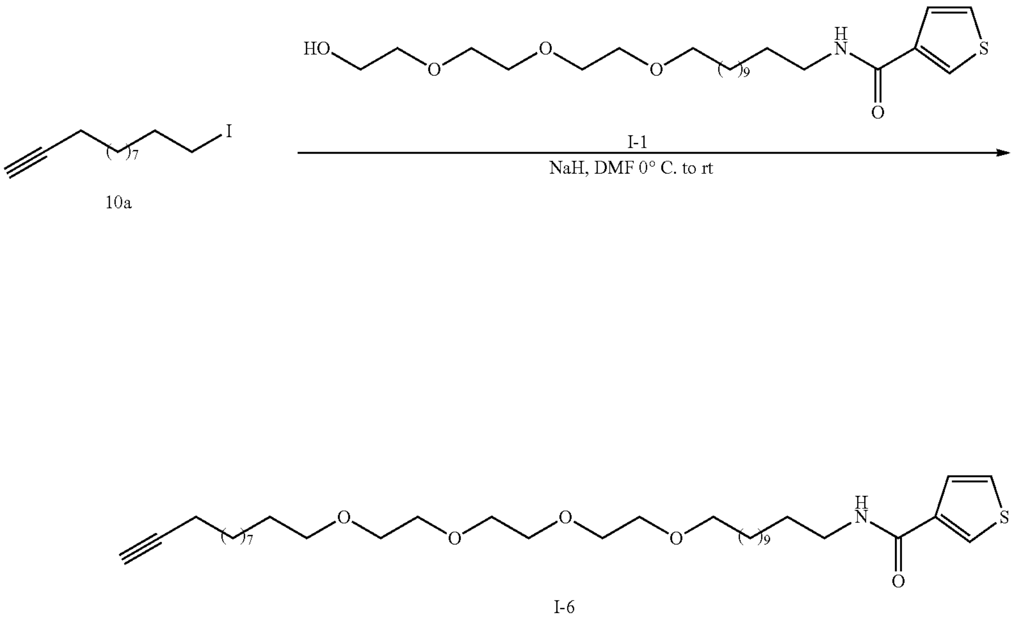

10a

I-6

Under a nitrogen atmosphere, to a solution of compound (I-1) (50.0 mg, 0.113 mmol) in dehydrated N,N-dimethylformamide (1.13 mL) was added, under ice-cooling, sodium hydride (60% in oil, 22.5 mg, 0.564 mmol), and the mixture was stirred under ice-cooling for 10 min. Under ice-cooling, 12-iodo-1-dodecyne (compound (10a)) (98.1 mg, 0.334 mmol) obtained in Reference Example 1 was added thereto, and the mixture was stirred at room temperature for 7 hr. To the reaction mixture was added water at room temperature, and the mixture was extracted with ethyl acetate. The organic layer was washed with saturated brine, and dried over anhydrous magnesium sulfate. The solvent was evaporated under reduced pressure, and the residue was purified by silica gel column chromatography (n-hexane:ethyl acetate=5:1-+2:1) to give the title compound (compound (I-6)) (42.9 mg, 63%) as a white waxy solid.

M.p. 52.3-53.7° C. (dec.);

$^1$H NMR (400 MHz, $CDCl_3$) δ: 1.26-1.41 (m, 30H), 1.48-1.66 (m, 6H), 1.94 (t, 1H, J=2.6 Hz), 2.18 (td, 2H, J=7.1, 2.6 Hz), 3.39-3.46 (m, 6H), 3.57-3.59 (m, 4H), 3.63-3.66 (m, 8H), 5.97 (brs, 1H), 7.34 (dd, 1H, J=5.1, 2.9 Hz), 7.37 (dd, 1H, J=5.1, 1.3 Hz), 7.84 (dd, 1H, J=2.9, 1.3 Hz);

$^{13}$C NMR (100 Hz, $CDCl_3$) δ: 18.4, 26.0 (2C), 27.0, 28.5, 28.7 (2C), 29.1, 29.3, 29.4 (3C), 29.5 (3C), 29.6 (2C), 29.7 (2C), 39.8, 68.0, 70.0 (3C), 70.6 (3C), 71.5 (2C), 84.8, 125.9, 126.4, 127.8, 137.7, 163.0;

IR (ATR) $cm^{-1}$: 3334, 1626;

MS (FAB) m/z: 607 $[M]^+$;

HRMS (FAB) m/z: Calcd for $C_{35}H_{61}NO_5S$: 607.4270; Found: 607.4272 $[M]^+$.

Example 7

Synthesis of N-(13,16,19,22-tetraoxa-32-tritriacontyn-1-yl)thiophene-3-carboxamide (compound (I-7))

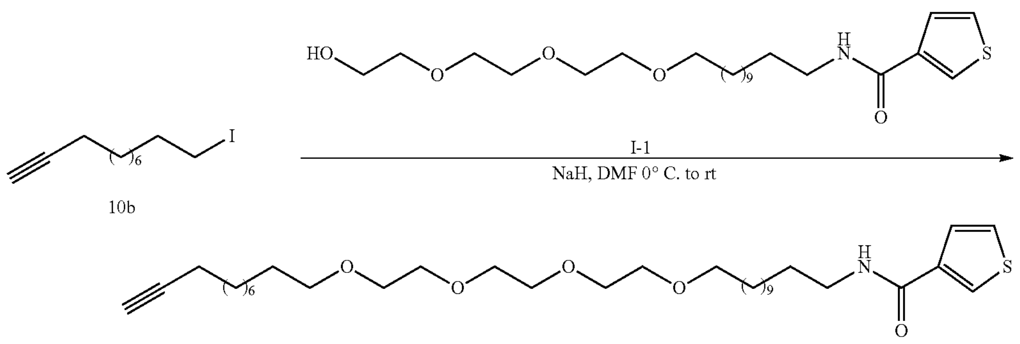

10b
I-6

Under a nitrogen atmosphere, to a solution of compound (I-1) (38.2 mg, 86.0 μmol) in dehydrated N,N-dimethylformamide (0.860 mL) was added, under ice-cooling, sodium hydride (60% in oil, 17.2 mg, 0.430 mmol), and the mixture was stirred under ice-cooling for 10 min. Under ice-cooling, 11-iodo-1-undecyne (compound (10b)) (71.8 mg, 0.258 mmol) obtained in Reference Example 2 was added thereto, and the mixture was stirred at room temperature for 6 hr. To the reaction mixture was added water at room temperature, and the mixture was extracted with ethyl acetate. The organic layer was washed with saturated brine, and dried over anhydrous magnesium sulfate. The solvent was evaporated under reduced pressure, and the residue was purified by silica gel column chromatography (n-hexane:ethyl acetate=5:1) to give the title compound (compound (I-7)) (25.2 mg, 49%) as a white waxy solid.

M.p. 60.6-62.1° C. (dec.);

$^1$H NMR (400 MHz, $CDCl_3$) δ: 1.26-1.84 (m, 34H), 1.94 (t, 1H, J=2.6 Hz), 2.18 (td, 2H, J=7.1, 2.6 Hz), 3.38-3.47 (m, 6H), 3.56-3.66 (m, 12H), 6.05 (brs, 1H), 7.33 (dd, 1H, J=5.1, 2.9 Hz), 7.38 (dd, 1H, J=5.1, 1.4 Hz), 7.85 (dd, 1H, J=2.9, 1.4 Hz);

$^{13}$C NMR (100 Hz, $CDCl_3$) δ: 18.4, 26.03, 26.04, 27.0, 28.4, 28.7, 29.0, 29.28, 29.39 (2C), 29.43, 29.48, 29.51 (3C), 29.58 (2C), 29.7, 39.8, 68.0, 70.0, 70.57 (2C), 70.58 (2C), 71.49 (2C), 71.51, 84.8, 125.9, 126.4, 127.8, 137.8, 163.0;

IR (ATR) $cm^{-1}$: 3339, 1622;

MS (FAB) m/z: 593 $[M]^+$;

HRMS (FAB) m/z: Calcd for $C_{34}H_{59}NO_5S$: 593.4114; Found: 593.4113 $[M]^+$.

Example 8

Synthesis of N-(13,16,19,22-tetraoxa-26-heptacosyn-1-yl)-5-methylthiophene-3-carboxamide (compound (I-8))

I-8

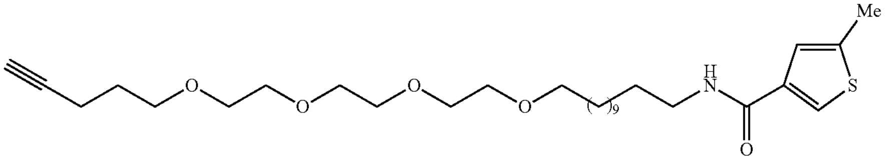

(8-1) Synthesis of 21-azido-3,6,9-trioxa-1-heneicosanol (Compound (12a))

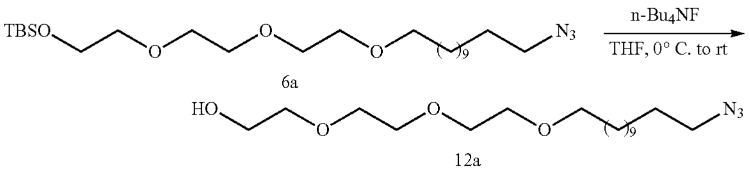

12a

Under a nitrogen atmosphere, to a solution of compound (6a) (243 mg, 0.513 mmol) obtained in Example 1 (1-2) in dehydrated tetrahydrofuran (5.13 mL) was added, under ice-cooling, tetrabutylammonium fluoride (about 1.00M tetrahydrofuran solution, 2.56 mL, 2.56 mmol), and the mixture was stirred at room temperature for 15 min. To the reaction mixture was added, at room temperature, saturated aqueous ammonium chloride solution, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate) to give 21-azido-3,6,9-trioxa-1-heneicosanol (compound (12a)) (181 mg, 98%) as a clear colorless oil.

$^{1}H$ NMR (400 MHz, $CDCl_3$) δ: 1.23-1.40 (m, 16H), 1.55-1.67 (m, 4H), 2.54 (t, 1H, J=6.4 Hz), 3.26 (t, 2H, J=7.1 Hz), 3.45 (t, 2H, J=6.8 Hz), 3.58-3.75 (m, 12H);

$^{13}C$ NMR (100 MHz, $CDCl_3$) δ: 25.9 (2C), 26.5 (2C), 28.7 (2C), 29.0 (2C), 29.3, 29.4, 51.3, 61.5, 69.8, 70.2, 70.4 (2C), 71.4, 72.4;

IR (ATR) $cm^{-1}$: 3445, 2091;

MS (ESI) m/z: 382 $[M+Na]^+$;

HRMS (ESI) m/z: Calcd for $C_{18}H_{37}N_3O_4$: 382.2676; Found: 382.2680 $[M+Na]^+$.

(8-2) Synthesis of 27-azido-6,9,12,15-tetraoxa-1-heptacosyne (Compound (13a))

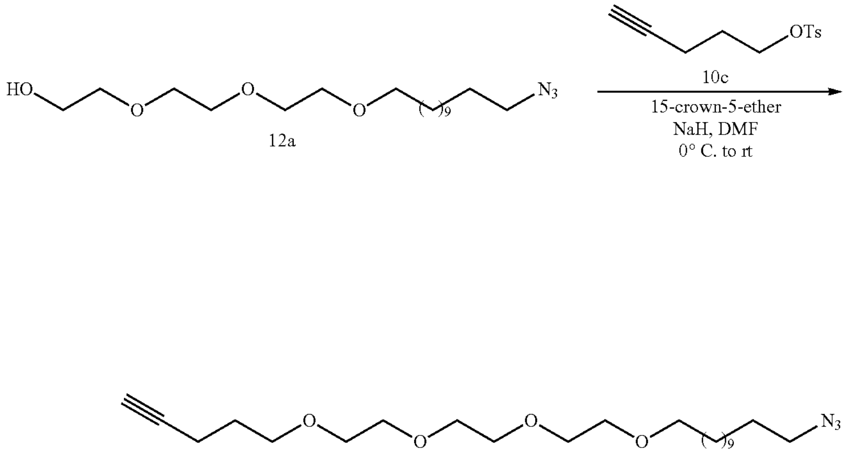

13a

Under a nitrogen atmosphere, to a solution of compound (12a) (388 mg, 1.08 mmol) in dehydrated dimethylformamide (0.270 mL) was added, under ice-cooling, sodium hydride (60% in oil, 86.4 mg, 2.16 mmol), and the mixture was stirred at the same temperature for 10 min. Under ice-cooling, 15-crown-5-ether (0.43 mL, 2.16 mmol) and a solution of compound (10c) (515 mg, 2.16 mmol) obtained in Reference Example 3 in dehydrated dimethylformamide (0.810 mL) were added thereto, and the mixture was stirred at room temperature for 26 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=20:1-+5:1) to give 27-azido-6,9,12,15-tetraoxa-1-heptacosyne (compound (13a)) (406 mg, 88%) as a clear colorless oil.

$^1$H NMR (500 MHz, $CDCl_3$) δ: 1.27-1.37 (m, 16H), 1.55-1.62 (m, 4H), 1.80 (qn, 2H, J=6.7 Hz), 1.94 (t, 1H, J=2.6 Hz), 2.29 (td, 2H, J=7.1, 2.6 Hz), 3.25 (t, 2H, J=7.1 Hz), 3.45 (t, 2H, J=6.8 Hz), 3.55-3.66 (m, 14H);

$^{13}$C NMR (100 MHz, $CDCl_3$) δ: 15.1, 26.0, 26.7, 28.4, 28.8, 29.1, 29.4 (2C), 29.47, 29.50, 29.52, 29.6, 51.4, 68.4, 68.5, 70.0, 70.2, 70.5 (2C), 70.6 (2C), 71.5, 84.0;

IR (ATR) $cm^{-1}$: 2092;

MS (ESI) m/z: 448 $[M+Na]^+$;

HRMS (ESI) m/z: Calcd for $C_{23}H_{43}N_3NaO_4$: 448.3146; Found: 448.3144 $[M+Na]^+$.

(8-3) Synthesis of Compound (I-8)

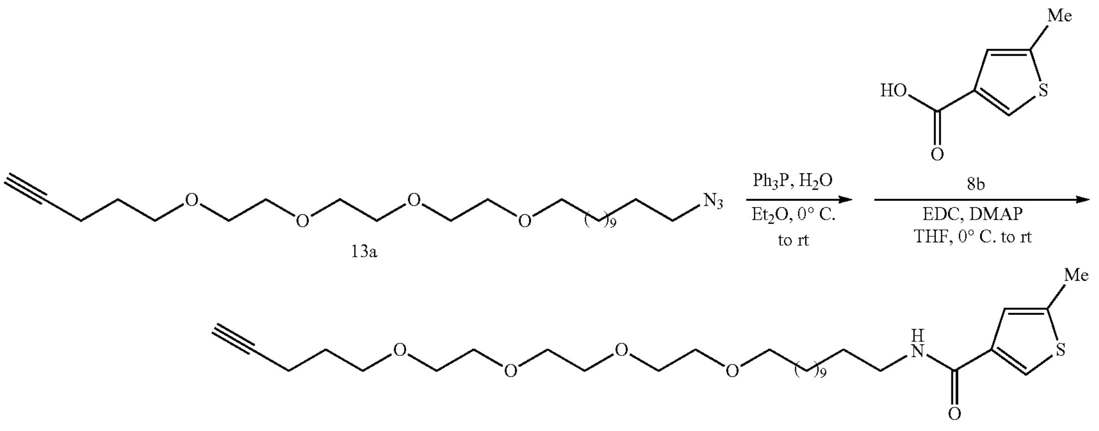

13a

I-8

To a mixed solution of compound (13a) (116 mg, 0.272 mmol) in diethyl ether/water (1:1, 3.50 mL) was added, under ice-cooling, triphenylphosphine (107 mg, 0.408 mmol), and the mixture was stirred at the same temperature for 24 hr. 6N Aqueous sodium hydroxide solution was added thereto at room temperature, and the mixture was extracted with diethyl ether. The organic layer was dried over anhydrous sodium sulfate. The solvent was evaporated under reduced pressure. To a solution of the residue in dehydrated tetrahydrofuran (0.543 mL) was added, under an argon atmosphere and under ice-cooling, 5-methyl-3-thiophenecarboxylic acid (compound (8b)) (manufactured by FUJIFILM Wako Pure Chemical Corporation) (77.2 mg, 4.94 mmol), 1-ethyl-3-(3-dimethylaminopropyl) carbodiimide hydrochloride (104 mg, 0.543 mmol), and N,N-dimethyl-4-aminopyridine (66.3 mg, 0.543 mmol), and the mixture was stirred at room temperature for 2 hr. Water was added thereto at room temperature, and the mixture was extracted with ethyl acetate. The organic layer was washed with water and saturated brine, and dried over anhydrous magnesium sulfate. The solvent was evaporated under reduced pressure. The residue was purified by silica gel column chromatography (n-hexane:ethyl acetate=2:1) to give the title compound (compound (I-8)) (96.5 mg, 62%) as a white waxy solid.

M.p. 33.2-36.0° C.;

$^1$H NMR (400 MHz, $CDCl_3$) δ: 1.23-1.35 (m, 16H), 1.53-1.60 (m, 4H), 1.79 (qn, 2H, J=7.0 Hz), 1.95 (t, 1H, J=2.6 Hz), 2.28 (td, 2H, J=7.1, 2.6 Hz), 2.47 (s, 3H), 3.34-3.46 (m, 4H), 3.54-3.66 (m, 14H), 6.27 (br, 1H), 7.04-7.06 (m, 1H), 7.62 (d, 1H, J=0.9 Hz);

$^{13}$C NMR (100 MHz, $CDCl_3$) δ: 15.1, 15.2, 26.0, 26.1, 26.9, 28.4, 29.2, 29.4, 29.45 (2C), 29.49, 29.6, 29.7, 39.7, 68.4, 69.5, 70.0, 70.1, 70.4, 70.5 (2C), 70.9, 71.4, 83.9, 124.0, 125.7, 137.3, 140.6, 163.1;

IR (ATR) $cm^{-1}$: 3333, 1626;

MS (EI) m/z (%): 523 (7) $[M]^+$, 426 (2), 125 (75), 97 (84);

HRMS (EI) m/z: Calcd for $C_{29}H_{49}NO_5S$: 523.3342; Found: 523.3331 $[M]^+$.

Example 9

Synthesis of N-(13,16,19,22-tetraoxatricosan-1-yl) thiophene-3-carboxamide (Compound (I-9))

I-9

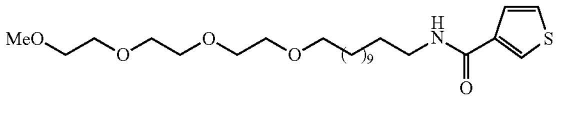

(9-1) Synthesis of 13,16,19,22-tetraoxa-1-tricosanol (Compound (16a))

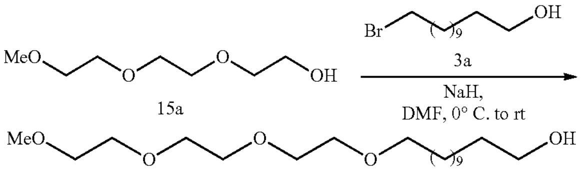

15a

16a

Under a nitrogen atmosphere, to a solution of triethylene glycol monomethylether (compound (15a)) (manufactured by Tokyo Chemical Industry Co., Ltd.) (1.24 g, 7.57 mmol) in dehydrated dimethylformamide (5.00 mL) was added, under ice-cooling, sodium hydride (60% in oil, 0.182 g, 7.57 mmol), and the mixture was warmed to room temperature and stirred for 50 min. A solution of 12-bromo-1-dodecanol (compound (3a)) (manufactured by Tokyo Chemical Industry Co., Ltd.) (0.669 g, 2.52 mmol) in dehydrated dimethylformamide (5.00 mL) was added dropwise thereto at room temperature, and the mixture was stirred at the same temperature for 24 hr. To the reaction mixture was added water, and the mixture was extracted with ethyl acetate. The organic layer was washed three times with saturated brine, and dried over anhydrous sodium sulfate. The solvent was evaporated under reduced pressure. The residue was purified by silica gel column chromatography (n-hexane:ethyl acetate=5:1→1:1) to give 13,16,19,22-tetraoxa-1-tricosanol (compound (16a)) (0.542 g, 62%) as a colorless oil.

$^{1}$H NMR (400 MHz, $CDCl_3$) δ: 1.26-1.31 (s, 17H), 1.55-1.59 (m, 3H), 1.55-1.59 (m, 1H), 3.39 (s, 3H), 3.45 (t, 2H, J=6.8 Hz), 3.54-3.60 (m, 4H), 3.63-3.68 (m, 10H);

$^{13}$C NMR (100 MHz, $CDCl_3$) δ: 25.8, 26.1, 29.5 (2C), 29.6 (3C), 29.7 (2C), 32.8, 59.1, 62.9, 70.1, 70.5, 70.6, 70.6 (2C), 71.6, 72.0;

IR ($CHCl_3$) $cm^{-1}$: 3466;

MS (EI) m/z (%): 348 (0.2) $[M]^+$, 103 (34.6), 85 (62.1), 83 (91.8), 59 (100.0), 58 (59.2), 55 (53.4);

HRMS (EI) m/z: Calcd for $C_{19}H_{40}O_5$: 348.2876; Found: 348.2874 $[M]^+$.

(9-2) Synthesis of 13,16,19,22-tetraoxa-1-iodotricosane (Compound (17a))

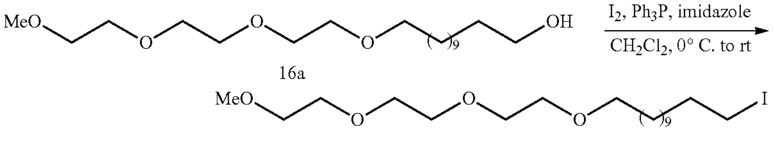

16a

17a

To a solution of triphenylphosphine (579 mg, 2.21 mmol) and imidazole (410 mg, 6.03 mmol) in dehydrated dichloromethane (10.0 mL) was added, under ice-cooling, iodine (561 mg, 3.08 mmol), and the mixture was warmed to room temperature and stirred under shading for 30 min. To the reaction mixture was added a solution of compound (16a) (579 mg, 2.21 mmol) in dehydrated dichloromethane (7.50 mL) at room temperature, and the mixture was stirred under shading at room temperature for 22 hr. Saturated aqueous sodium thiosulfate solution (15 mL) was added thereto, and the mixture was extracted with ethyl acetate. The organic layer was washed twice with saturated brine, and dried over anhydrous sodium sulfate. The solvent was evaporated under reduced pressure. The residue was purified by silica gel chromatography (n-hexane:ethyl acetate=5:1) to give 13,16,19,22-tetraoxa-1-iodotricosane (compound (17a)) (0.787 g, 86%) as a yellow oil.

$^{1}$H NMR (400 MHz, $CDCl_3$) δ: 1.26-1.38 (m, 16H), 1.56-1.59 (m, 2H), 1.78-1.84 (m, 2H), 3.19 (t, 2H, J=7.2 Hz), 3.39 (s, 3H), 3.54-3.60 (m, 5H), 3.63-3.68 (m, 9H);

$^{13}$C NMR (100 MHz, $CDCl_3$) δ: 7.39, 26.1, 28.6, 29.5, 29.5 (2C), 29.6 (2C), 29.7, 30.6, 33.6, 59.1, 70.1, 70.6, 70.6, 70.7, 70.8, 71.6, 71.9;

MS (CI) m/z (%): 459 (49.0) $[M+H]^+$, 323 (64.3), 292 (100.0), 211 (33.3), 165 (50.9), 103 (54.2);

HRMS (CI) m/z: Calcd for $C_{19}H_{40}IO_4$: 459.1972; Found: 459.1966 $[M+H]^+$.

(9-3) Synthesis of 13,16,19,22-tetraoxa-1-azidotricosane (Compound (13a))

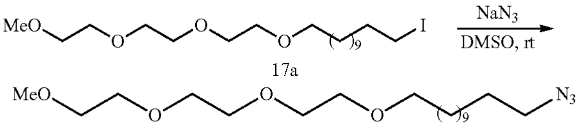

17a

13a

To a solution of compound (17a) (0.228 g, 0.470 mmol) in dehydrated dimethyl sulfoxide (4.70 mL) was added sodium azide (61.2 mg, 0.941 mmol) at room temperature and the mixture was stirred at room temperature for 2 hr. To the reaction mixture was added water, and the mixture was extracted with diethyl ether. The organic layer was washed twice each with water and saturated brine, and dried over anhydrous sodium sulfate. The solvent was evaporated under reduced pressure. The residue was purified by silica gel column chromatography (n-hexane:ethyl acetate=1:2) to give 13,16,19,22-tetraoxa-1-azidotricosane (compound (13a)) (176 mg, quant.) as a colorless oil.

$^{1}$H NMR (400 MHz, $CDCl_3$) δ: 1.26 (s, 16H), 1.58-1.62 (m, 4H), 3.26 (t, 2H, J=6.8 Hz), 3.38 (s, 3H), 3.54-3.60 (m, 5H), 3.63-3.68 (m, 9H);

$^{13}$C NMR (100 MHz, $CDCl_3$) δ: 26.1, 26.8, 28.9, 29.2, 29.5 (2C), 29.6 (3C), 29.7, 33.6, 51.5, 59.1, 70.1, 70.6 (2C), 70.7 (2C), 71.6, 72.0;

IR ($CHCl_3$) $cm^{-1}$: 2098;

MS (CI) m/z (%): 374 (17.3) $[M+H]^+$, 346 (53.8), 270 (27.8), 226 (35.5), 198 (94.5), 182 (100.0), 103 (36.9);

HRMS (CI) m/z: Calcd for $C_{19}H_{40}N_3O_4$: 374.3019; Found: 374.3024 $[M+H]^+$.

(9-4) Synthesis of 13,16,19,22-tetraoxa-1-tricosylamine (Compound (14a))

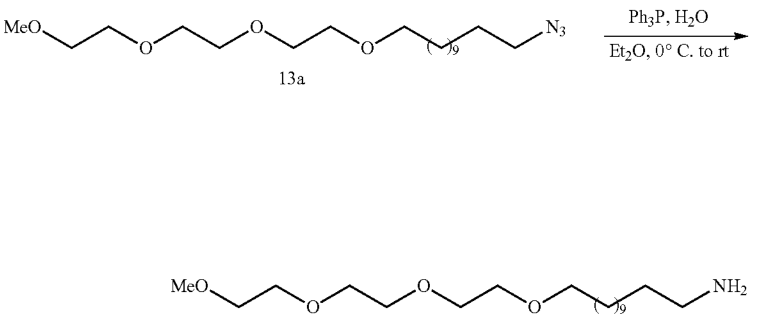

13a

14a

To a solution of compound (13a) (464 mg, 1.24 mmol) in diethyl ether (6.2 mL) was added, under ice-cooling, triphenylphosphine (326 mg, 1.24 mmol), and the mixture was stirred at room temperature for 5 min. Water (6.2 mL) was added thereto, and the mixture was stirred at room temperature for 20 hr. 6N Hydrochloric acid was added to adjust the mixture to pH 1, and the mixture was washed with diethyl ether. The aqueous layer was adjusted to pH 11 by adding 6N aqueous sodium hydroxide solution, and the mixture was extracted with diethyl ether. The solvent was evaporated under reduced pressure to give 13,16,19,22-tetraoxa-1-tricosylamine (compound (14a)) (427 mg, 99%) as a white waxy solid.

$^1$H NMR (400 MHz, $CDCl_3$) δ: 1.26-1.32 (s, 16H), 1.41-1.43 (m, 2H), 1.56-1.59 (m, 2H), 2.68 (t, 2H, J=6.8 Hz), 3.39 (s, 3H), 3.54-3.59 (m, 5H), 3.63-3.67 (m, 9H);

$^{13}$C NMR (100 MHz, $CDCl_3$) δ: 26.1, 26.9, 29.5 (2C), 29.6 (5C), 33.9, 42.3, 59.0, 70.0, 70.5, 70.6 (3C), 71.5, 71.9;

IR ($CHCl_3$) $cm^{-1}$: 3378;

MS (CI) m/z (%): 374 (17.3) $[M+H]^+$, 346 (53.8), 270 (27.8), 226 (35.5), 198 (94.5), 182 (100.0), 103 (36.9);

HRMS (CI) m/z: Calcd for $C_{19}H_{42}NO_4$: 348.3114; Found: 348.3107 $[M+H]^+$.

(9-5) Synthesis of Compound (I-9)

To a solution of compound (14a) (61.5 mg, 0.177 mmol) in dehydrated tetrahydrofuran (0.850 mL) were added, under ice-cooling, 3-thiophenecarboxylic acid (compound (8a)) (45.4 mg, 0.354 mmol), 1-ethyl-3-(3-dimethylaminopropyl) carbodiimide hydrochloride (81.4 mg, 0.425 mmol) and N,N-dimethyl-4-aminopyridine (43.2 mg, 0.354 mmol), and the mixture was stirred at room temperature for 22 hr. To the reaction mixture was added water, and the mixture was extracted with ethyl acetate. The organic layer was washed twice with saturated brine and dried over anhydrous magnesium sulfate. The solvent was evaporated under reduced pressure. The residue was purified by silica gel column chromatography (n-hexane:ethyl acetate=1:2) to give the title compound (compound (I-9)) (65.6 mg, 81%) as a white solid.

M.p. 39.3-42.0° C. (dec.);

$^1$H NMR (400 MHz, $CDCl_3$) δ: 1.26-1.33 (m, 16H), 1.54-1.66 (m, 4H), 3.38 (s, 3H), 3.39-3.46 (m, 2H), 3.54-3.59 (m, 5H), 3.63-3.67 (m, 9H), 5.97 (s, 1H), 7.32-7.34 (m, 1H), 7.36-7.38 (m, 1H), 7.84-7.85 (m, 1H);

$^{13}$C NMR (100 MHz, $CDCl_3$) δ: 26.1, 27.1, 29.4, 29.6 (6C), 29.8, 39.9, 59.1, 70.1, 70.7 (4C), 71.6, 72.0, 126.3 (2C), 128.0, 137.9, 163.2;

IR ($CHCl_3$) $cm^{-1}$: 1651;

MS (EI) m/z (%): 457 (12.6) $[M]^+$, 310 (61.3), 294 (45.8), 111 (100.0), 59 (28.6);

HRMS (EI) m/z: Calcd for $C_{24}H_{43}NO_5S$: 457.2862; Found: 457.2856 $[M]^+$.

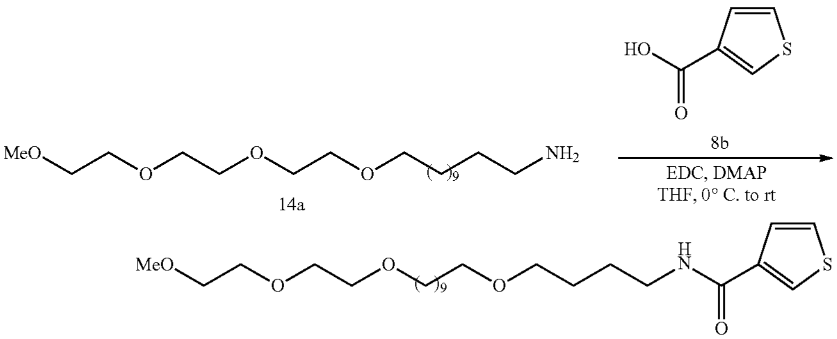

14a

I-9

Example 10

Synthesis of N-(13,16,19,22-tetraoxatricosan-1-yl)-5-methylthiophene-3-carboxamide (Compound (I-10))

I-10

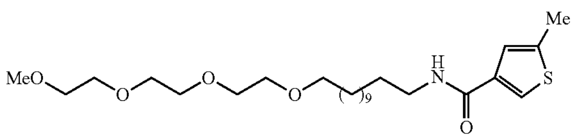

To a solution of compound (14a) (100 mg, 0.288 mmol) obtained in Example 9 (9-4) in dehydrated tetrahydrofuran (1.44 mL) were added, under ice-cooling, 5-methylthiophene-3-carboxylic acid (manufactured by FUJIFILM Wako Pure Chemical Corporation) (compound (8b)) (82.0 mg, 0.576 mmol), 1-ethyl-3-(3-dimethylaminopropyl)carbodiimide hydrochloride (132 mg, 0.691 mmol) and N,N-dimethyl-4-aminopyridine (70.0 mg, 0.576 mmol), and the mixture was stirred at room temperature for 18 hr. To the reaction mixture was added water, and the mixture was extracted with ethyl acetate. The organic layer was washed twice with saturated brine and dried over anhydrous magnesium sulfate. The solvent was evaporated under reduced pressure. The residue was purified by silica gel column chromatography (n-hexane:ethyl acetate=1:2) to give the title compound (compound (I-10)) (126 mg, 75%) as a white solid.

M.p. 43.6-45.0° C. (dec.);

$^{1}$H NMR (400 MHz, $CDCl_3$) δ: 1.26-1.33 (m, 16H), 1.53-1.60 (m, 4H), 2.48 (d, 3H, J=4.4 Hz), 3.38 (s, 3H), 3.40-3.47 (m, 4H), 3.55-3.67 (m, 12H), 5.91 (br, 1H), 7.02 (m, 1H, J=1.6 Hz), 7.58 (d, 1H, J=2.0 Hz);

$^{13}$C NMR (100 MHz, $CDCl_3$) δ: 15.1, 26.0, 26.9, 29.2, 29.4 (5C), 29.5, 29.6, 39.7, 58.9, 69.9, 70.4, 70.5 (3C), 71.4, 71.8, 124.0, 125.7, 137.3, 140.6, 163.1;

IR (neat) $cm^{-1}$: 3330, 1625;

MS (EI) m/z: 471 (29.2) $[M]^+$, 324 (45.3), 308 (29.5), 125 (100);

HRMS (EI) m/z: Calcd for $C_{25}H_{45}NO_5S$: 471.3018; Found: 471.3023 $[M]^+$.

Example 11

Synthesis of N-(13,16,19,22-tetraoxatricosan-1-yl)-2-methylthiophene-3-carboxamide (compound (I-11))

I-11

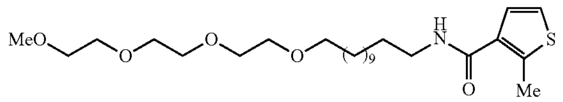

To a solution of compound (14a) (200 mg, 0.576 mmol) obtained in Example 9 (9-4) in dehydrated tetrahydrofuran (2.88 mL) were added, under ice-cooling, 2-methylthiophene-3-carboxylic acid (manufactured by Sigma-Aldrich Co. LLC) i5 (compound (8c)) (164 mg, 1.15 mmol), 1-ethyl-3-(3-dimethylaminopropyl)carbodiimide hydrochloride (265 mg, 1.38 mmol) and N,N-dimethyl-4-aminopyridine (140 mg, 1.15 mmol), and the mixture was stirred at room temperature for 22 hr. To the reaction mixture was added water, and the mixture was extracted with ethyl acetate. The organic layer was washed twice with saturated brine and dried over anhydrous magnesium sulfate. The solvent was evaporated under reduced pressure. The residue was purified by silica gel column chromatography (n-hexane:ethyl acetate=1:2) to give the title compound (compound (I-11)) (262 mg, 78%) as a pale-yellow oil.

$^{1}$H NMR (400 MHz, $CDCl_3$) δ: 1.26-1.33 (m, 16H), 1.58-1.59 (m, 4H), 2.70 (s, 3H), 3.38 (s, 3H), 3.41-3.47 (m, 4H), 3.55-3.67 (m, 12H), 5.76 (br, 1H), 7.03 (d, 1H, J=7.2 Hz), 7.08 (d, 1H, J=7.2 Hz);

$^{13}$C NMR (100 MHz, $CDCl_3$) δ: 14.5, 25.8, 26.8, 29.1, 29.2, 29.3 (5C), 29.4, 39.4, 58.7, 69.7, 70.2 (2C), 70.3 (2C), 71.2, 71.6, 121.3, 126.3, 132.0, 143.7, 164.4;

IR (neat) $cm^{-1}$: 3334, 1632;

MS (EI) m/z (%): 471 (18.3) $[M]^+$, 324 (32.2), 125 (100.0);

HRMS (EI) m/z: Calcd for $C_{25}H_{45}NO_5S$: 471.3018; Found: 471.3021 $[M]^+$.

Example 12

Synthesis of N-(13,16,19,22-tetraoxatricosan-1-yl)-4-methylthiophene-3-carboxamide (compound (I-12))

I-12

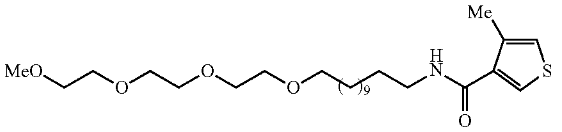

To a solution of compound (14a) (86.5 mg, 0.249 mmol) obtained in Example 9 (9-4) in dehydrated tetrahydrofuran (1.24 mL) were added, under ice-cooling, 4-methylthiophene-3-carboxylic acid (manufactured by Sigma-Aldrich Co. LLC) (compound (8d)) (70.8 mg, 0.498 mmol), 1-ethyl-3-(3-dimethylaminopropyl)carbodiimide hydrochloride (115 mg, 0.597 mmol) and N,N-dimethyl-4-aminopyridine (60.8 mg, 0.498 mmol), and the mixture was stirred at room temperature for 24 hr. To the reaction mixture was added water, and the mixture was extracted with ethyl acetate. The organic layer was washed twice with saturated brine, and dried over anhydrous magnesium sulfate. The solvent was evaporated under reduced pressure. The residue was purified by silica gel column chromatography (n-hexane:ethyl acetate=1:2) to give the title compound (compound (I-12)) (94.3 mg, 79%) as a pale-yellow oil.

$^{1}$H NMR (400 MHz, $CDCl_3$) δ: 1.26-1.33 (m, 16H), 1.58 (m, 4H), 2.42 (s, 3H), 3.38 (s, 3H), 3.41-3.47 (m, 4H), 3.55-3.67 (m, 12H), 5.84 (br, 1H), 6.94 (m, 1H), 7.58 (d, 1H, J=4.4 Hz);

$^{13}$C NMR (100 MHz, $CDCl_3$) δ: 15.4, 25.9, 26.8, 29.2, 29.3, 29.4 (5C), 29., 39.6, 58.8, 69.8, 70.3, 70.4 (3C), 71.3, 71.7, 122.5, 127.0, 137.1, 137.3, 164.8;

IR (neat) $cm^{-1}$: 3335, 1635;

MS (EI) m/z: 471 (22.1) [M], 324 (43.1), 308 (30.2), 125 (100);

HRMS (EI) m/z: Calcd for $C_{25}H_{45}NO_5S$: 471.3018; Found: 471.3014 $[M]^+$.

Example 13

Synthesis of N-(13,16,19,22-tetraoxatricosan-1-yl)-5-bromothiophene-3-carboxamide (compound (I-13))

I-13

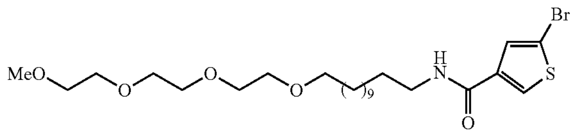

To a solution of compound (14a) (155 mg, 0.446 mmol) obtained in Example 9 (9-4) in dehydrated tetrahydrofuran (2.23 mL) were added, under ice-cooling, 5-bromothiophene-3-carboxylic acid (manufactured by Sigma-Aldrich Co. LLC) (compound (8e)) (185 mg, 0.892 mmol), 1-ethyl-3-(3-dimethylaminopropyl)carbodiimide hydrochloride (205 mg, 1.07 mmol) and N,N-dimethyl-4-aminopyridine (109 mg, 0.892 mmol), and the mixture was stirred at room temperature for 23 hr. To the reaction mixture was added water, and the mixture was extracted with ethyl acetate. The organic layer was washed twice with saturated brine, and dried over anhydrous magnesium sulfate. The solvent was evaporated under reduced pressure. The residue was purified by silica gel column chromatography (n-hexane:ethyl acetate=1:2) to give the title compound (compound (I-13)) (209 mg, 87%) as a white solid.

M.p. 35.6-37.0° C. (dec.);

$^1H$ NMR (400 MHz, $CDCl_3$) δ: 1.26-1.32 (m, 16H), 1.53-1.60 (m, 4H), 3.38 (s, 3H), 3.40-3.47 (m, 4H), 3.54-3.67 (m, 12H), 5.93 (br, 1H), 7.32 (d, 1H, J=2.4 Hz), 7.74 (d, 1H, J=2.4 Hz);

$^{13}C$ NMR (100 MHz, $CDCl_3$) δ: 25.9, 26.9, 29.2, 29.3, 29.4 (6C), 39.8, 58.8, 69.9, 70.3 (2C), 70.4 (2C), 71.3, 71.7, 112.8, 128.8, 129.2, 137.8, 161.8;

IR (neat) $cm^{-1}$: 3301, 1611;

MS (EI) m/z: 537 (13.8) $[M+2]^+$, 535 (12.6) $[M]^+$, 456 (35.6), 388 (64.1), 59 (100);

HRMS (EI) m/z: Calcd for $C_{24}H_{42}BrNO_5S$: 535.1967; Found: 535.1962 $[M]^+$.

Example 14

Synthesis of N-(13,16,19,22-tetraoxatricosan-1-yl)-4-bromothiophene-3-carboxamide (Compound (I-14))

I-14

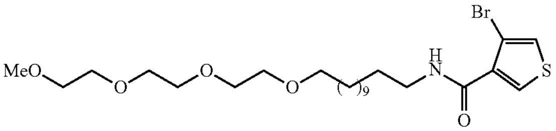

To a solution of compound (14a) (155 mg, 0.446 mmol) obtained in Example 9 (9-4) in dehydrated tetrahydrofuran (2.23 mL) were added, under ice-cooling, 4-bromothiophene-3-carboxylic acid (manufactured by Sigma-Aldrich Co. LLC) (compound (8f)) (185 mg, 0.892 mmol), 1-ethyl-3-(3-dimethylaminopropyl)carbodiimide hydrochloride (205 mg, 1.07 mmol) and N,N-dimethyl-4-aminopyridine (109 mg, 0.892 mmol), and the mixture was stirred at room temperature for 22 hr. To the reaction mixture was added water, and the mixture was extracted with ethyl acetate. The organic layer was washed twice with saturated brine, and dried over anhydrous magnesium sulfate. The solvent was evaporated under reduced pressure. The residue was purified by silica gel column chromatography (n-hexane:ethyl acetate=1:2) to give the title compound (compound (I-14)) (224 mg, 94%) as a colorless oil.

$^1H$ NMR (400 MHz, $CDCl_3$) δ: 1.27-1.39 (m, 16H), 1.53-1.67 (m, 4H), 3.38 (s, 3H), 3.42-3.47 (m, 4H), 3.56-3.66 (m, 12H), 6.67 (br, 1H), 7.33 (d, 1H, J=4.8 Hz), 8.05 (d, 1H, J=4.8 Hz);

$^{13}C$ NMR (100 MHz, $CDCl_3$) δ: 25.8, 26.7, 29.0, 29.1, 29.2 (2C), 29.3 (3C), 29.4, 39.6, 58.7, 69.8, 70.2, 70.3 (3C), 71.2, 71.6, 107.2, 125.0, 131.0, 135.7, 161.6;

IR (neat) $cm^{-1}$: 3307, 1644;

MS (EI) m/z: 537 (4.7) $[M+2]^+$, 535 (5.5) $[M]^+$, 388 (19.2), 83 (100);

HRMS (EI) m/z: Calcd for $C_{24}H_{42}BrNO_5S$: 535.1967; Found: 535.1965 $[M]^+$.

Example 15

Synthesis of N-(13,16,19,22,25-pentaoxadotriacontan-1-yl)thiophene-3-carboxamide (Compound (I-15))

I-15

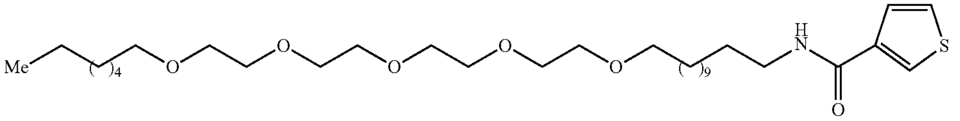

(15-1) Synthesis of 11-(t-butyldimethylsilyloxy)-3,6,9-trioxa-1-undecanol (Compound (2b))

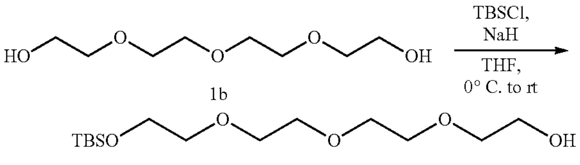

1b

2b

Under a nitrogen atmosphere, to dehydrated tetrahydrofuran (51.4 mL) was added sodium hydride (60% in oil, 1.13 g, 28.3 mmol), and tetraethylene glycol (manufactured by Tokyo Chemical Industry Co., Ltd.) (compound (1b)) (4.44 mL, 25.7 mmol) was added thereto under ice-cooling, and the mixture was stirred at the same temperature for 10 min. t-Butyldimethylsilyl chloride (4.66 g, 30.9 mmol) was added thereto at the same temperature, and the mixture was stirred at room temperature for 3 hr. Water was added thereto at room temperature, and the mixture was extracted with ethyl acetate. The organic layer was washed with saturated brine and dried over anhydrous sodium sulfate. The solvent was evaporated under reduced pressure. The residue was purified by silica gel column chromatography (n-hexane:ethyl acetate=2:1→1:1) to give 11-(t-butyldimethylsilyloxy)-3,6,9-trioxa-1-undecanol (compound (2b)) (3.16 g, 40%) as a pale-yellow oil.

$^1$H NMR (400 MHz, $CDCl_3$) δ: 0.07 (s, 6H), 0.89 (s, 9H), 3.56 (t, 2H, J=5.3 Hz), 3.61-3.63 (m, 2H), 3.67-3.68 (m, 8H), 3.71-3.74 (m, 2H), 3.77 (t, 2H, J=5.4 Hz).

$^1$H NMR of the synthesized compound (2b) was consistent with the data of the same compound described in non patent literature (Bar-Shir, A. et al., J. Org. Chem., 2005, 70(7), 2660-2666).

(15-2) Synthesis of 1-azido-24-(t-butyldimethylsilyloxy)-13, 16,19,22-tetraoxatetracosane (Compound (6b))

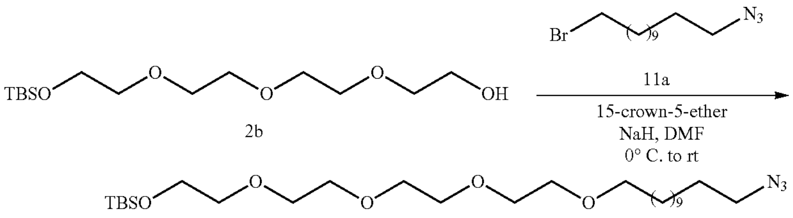

2b

6b

Under a nitrogen atmosphere, to a solution of compound (2b) (200 mg, 0.648 mmol) in dehydrated dimethylformamide (0.648 mL) was added, under ice-cooling, sodium hydride (60% in oil, 51.8 mg, 1.30 mmol), and the mixture was stirred at the same temperature for 10 min. 15-Crown-5-ether (0.256 mL, 1.30 mmol) and 1-azido-12-bromododecane (compound (11a)) (376 mg, 1.30 mmol) obtained in Reference Example 4 were added thereto at the same temperature, and the mixture was stirred at room temperature for 29 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=20:1→5:1) to give 1-azido-24-(t-butyldimethylsilyloxy)-13,16,19,22-tetraoxatetracosane (compound (6b)) (0.255 g, 76%) as a clear colorless oil.

$^1$H NMR (400 MHz, $CDCl_3$) δ: 0.07 (s, 6H), 0.89 (s, 9H), 1.24-1.40 (m, 16H), 1.54-1.66 (m, 4H), 3.26 (t, 2H, J=7.0 Hz), 3.45 (t, 2H, J=6.8 Hz), 3.54-3.59 (m, 4H), 3.63-3.68 (m, 10H), 3.77 (t, 2H, J=5.4 Hz);

$^{13}$C NMR (75 MHz, $CDCl_3$) 75: −5.3 (2C), 18.3, 25.9 (3C), 26.0, 26.7, 28.8, 29.1, 29.42, 29.43, 29.47, 29.51, 29.52, 29.6, 51.4, 62.7, 70.0, 70.55, 70.58, 70.65, 70.66, 71.49, 71.50, 72.6;

IR (ATR) $cm^{-1}$: 2093, 1102;

MS (ESI) m/z: 540 $[M+Na]^+$;

HRMS (ESI) m/z: Calcd for $C_{26}H_{55}N_3NaO_5Si$: 540.3803; Found: 540.3794 $[M+Na]^+$.

(15-3) Synthesis of 24-azido-3,6,9,12-tetraoxa-1-tetracosanol (Compound (12b))

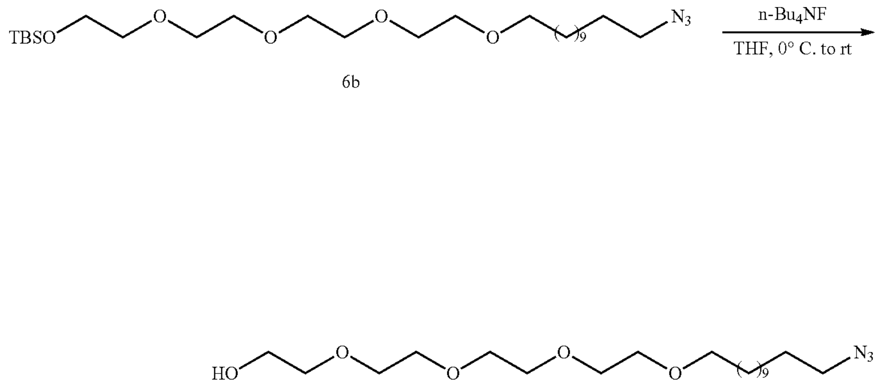

6b

12b

Under an argon atmosphere, to a solution of compound (6b) (326 mg, 0.629 mmol) in dehydrated tetrahydrofuran (6.29 mL) was added dropwise, under ice-cooling, tetra-n-butylammonium fluoride (about 1.00 M tetrahydrofuran solution, 6.29 mL, 6.29 mmol), and the mixture was stirred at room temperature for 1 hr. To the reaction mixture was added saturated aqueous ammonium chloride solution at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=1:1→1:2) to give 24-azido-3,6,9,12-tetraoxa-1-tetracosanol (compound (12b)) (204 mg, 80%) as a pale-yellow oil.

$^1$H NMR (500 MHz, $CDCl_3$) δ: 1.26-1.39 (m, 16H), 1.55-1.74 (m, 4H), 2.69 (br, 1H), 3.26 (t, 2H, J=7.0 Hz), 3.45 (t, 2H, J=6.8 Hz), 3.58-3.74 (m, 16H);

$^{13}$C NMR (75 MHz, $CDCl_3$) δ: 28.7, 29.1 (2C), 29.37 (2C), 29.42, 29.45, 29.47, 26.0, 26.6, 51.4, 61.6, 69.9, 70.2, 70.44, 70.47, 70.50, 70.51, 71.5, 72.5;

IR (ATR) $cm^{-1}$: 3458, 2093, 1105;

MS (ESI) m/z: 426 $[M+Na]^+$;

HRMS (ESI) m/z: Calcd for $C_{20}H_{41}N_3NaO_5$: 426.2938; Found: 426.2939 $[M+Na]^+$.

(15-4) Synthesis of 1-azido-13,16,19,22,25-pentaoxadotriacontane (Compound (13b))

Under a nitrogen atmosphere, to a solution of compound (12b) (117 mg, 0.290 mmol) in dehydrated dimethylformamide (0.970 mL) was added, under ice-cooling, sodium hydride (60% in oil, 23.2 mg, 0.580 mmol), and the mixture was stirred at the same temperature for 10 min. 1-Iodoheptane (manufactured by Tokyo Chemical Industry Co., Ltd.) (compound (10h)) (95.0 μL, 0.580 mmol) was added thereto at room temperature, and the mixture was stirred at room temperature for 15 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=5:1→1:2) to give 1-azido-13,16,19,22,25-pentaoxadotriacontane (compound (13b)) (108 mg, 74%) as a clear colorless oil.

$^1$H NMR (400 MHz, $CDCl_3$) δ: 0.88 (t, 3H, J=6.9 Hz), 1.23-1.40 (m, 24H), 1.54-1.68 (m, 6H), 3.26 (t, 2H, J=7.0 Hz), 3.45 (t, 4H, J=6.8 Hz), 3.57-3.59 (m, 4H), 3.63-3.66 (m, 12H);

$^{13}$C NMR (100 MHz, $CDCl_3$) δ: 14.1, 22.6, 25.98, 26.01 (2C), 26.7, 28.8, 29.1, 29.42, 29.43, 29.47, 29.49, 29.50, 29.52, 29.55, 31.8, 51.4, 70.0, 70.49 (2C), 70.50 (2C), 70.53 (2C), 70.54, 71.5 (2C);

IR (ATR) $cm^{-1}$: 2093, 1107;

MS (ESI) m/z: 524 $[M+Na]^+$;

HRMS (ESI) m/z: Calcd for $C_{27}H_{55}N_3NaO_5$: 524.4034; Found: 524.4039 $[M+Na]^+$.

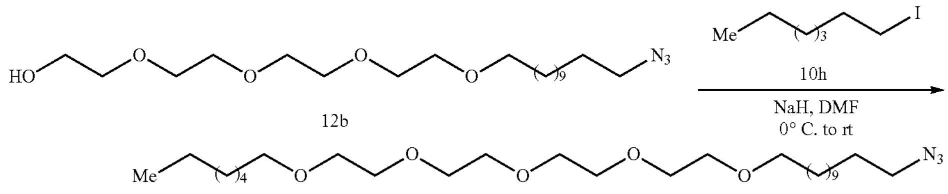

10h

12b

13b (15-5) Synthesis of Compound (I-15)

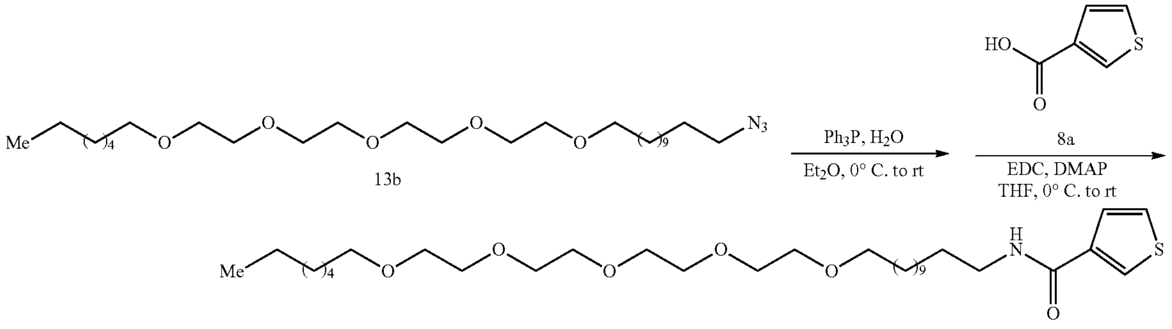

13b

I-15

To a solution of compound (13b) (174 mg, 0.347 mmol) in diethyl ether/water (1:1, 3.47 mL) was added, at room temperature, triphenylphosphine (137 mg, 0.520 mmol), and the mixture was stirred at the same temperature for 18 hr. 3M Aqueous sodium hydroxide solution was added thereto at room temperature, and the mixture was extracted with diethyl ether and dried over anhydrous sodium sulfate. The solvent was evaporated under reduced pressure. Under an argon atmosphere, to a solution of the residue in dehydrated tetrahydrofuran (6.94 mL) were added, under ice-cooling, 3-thiophenecarboxylic acid (compound (8a)) (89.0 mg, 0.694 mmol), 1-ethyl-3-(3-dimethylaminopropyl)carbodiimide hydrochloride (133 mg, 0.694 mmol) and N,N-dimethyl-4-aminopyridine (85.0 mg, 0.694 mmol), and the mixture was stirred at room temperature for 28 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=5:1→1:1) to give the title compound (compound (I-15)) (0.112 g, 55%) as a white waxy solid.

M.p. 51.6-52.4° C.;

$^{1}$H NMR (500 MHz, $CDCl_3$) δ: 0.88 (t, 3H, J=7.0 Hz), 1.22-1.39 (m, 24H), 1.55-1.63 (m, 6H), 3.40-3.46 (m, 6H), 3.57-3.60 (m, 4H), 3.62-3.66 (m, 12H), 5.96 (br, 1H), 7.34 (dd, 1H, J=5.0, 3.0 Hz), 7.37 (dd, 1H, J=5.0, 1.3 Hz), 7.84 (dd, 1H, J=3.0, 1.3 Hz);

$^{13}$C NMR (75 MHz, $CDCl_3$) δ: 14.0, 22.5, 25.95, 25.98, 27.0, 29.0, 29.2, 29.37 (2C), 29.43, 29.45 (2C), 29.52, 29.53, 29.6, 31.7, 39.8, 69.9 (3C), 70.48 (2C), 70.52 (3C), 71.4 (2C), 126.1, 126.2, 127.8, 137.7, 163.0;

IR (ATR) $cm^{-1}$: 3333, 1622;

MS (EI) m/z (%): 585 (11.3) $[M]^+$, 310 (44.3), 294 (42.4), 111 (100.0);

HRMS (EI) m/z: Calcd for $C_{32}H_{59}NO_6S$: 585.4063; Found: 585.4066 $[M]^+$.

Example 16

Synthesis of N-(10,13,16,19,22-pentaoxadotriacontan-1-yl)thiophene-3-carboxamide (Compound (I-16))

I-16

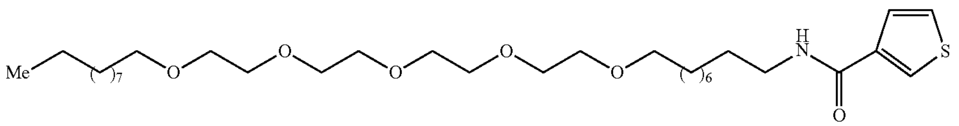

(16-1) Synthesis of 1-azido-21-(t-butyldimethylsilyloxy)-10,13,16,19-tetraoxaheneicosane (compound (6c))

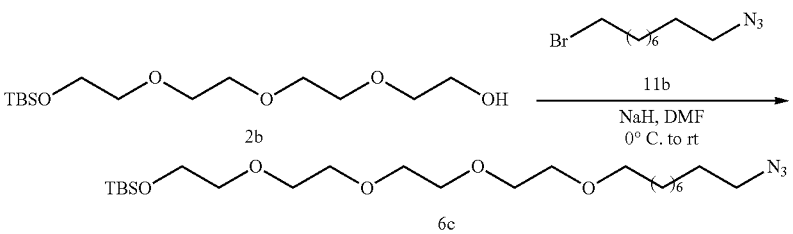

2b

6c

Under a nitrogen atmosphere, to a solution of compound (2b) (200 mg, 0.648 mmol) obtained in Example 15 (15-1) in dehydrated dimethylformamide (0.648 mL) was added, under ice-cooling, sodium hydride (60% in oil, 51.8 mg, 1.30 mmol), and the mixture was stirred at the same temperature for 10 min. 1-Azido-9-bromononane (compound (11b)) (481 mg, 1.94 mmol) obtained in Reference Example 5 was added thereto at the same temperature, and the mixture was stirred at room temperature for 21 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=20:1→5:1) to give 1-azido-21-(t-butyldimethylsilyloxy)-10,13,16,19-tetraoxaheneicosane (compound (6c)) (0.171 g, 56%) as a clear colorless oil.

$^1$H NMR (500 MHz, $CDCl_3$) δ: 0.06 (s, 6H), 0.89 (s, 9H), 1.25-1.37 (m, 10H), 1.55-1.65 (m, 4H), 3.26 (t, 2H, J=7.0 Hz), 3.45 (t, 2H, J=6.8 Hz), 3.55-3.59 (m, 4H), 3.63-3.66 (m, 10H), 3.77 (t, 2H, J=5.5 Hz);

$^{13}$C NMR (75 MHz, $CDCl_3$) δ: −5.3 (2C), 18.3, 25.9 (3C), 26.0, 26.7, 28.8, 29.0, 29.3, 29.4, 29.6, 51.4, 62.7, 70.0, 70.57 (2C), 70.60, 70.7, 71.5 (2C), 72.6;

IR (ATR) $cm^{-1}$: 2093, 1101;

MS (ESI) m/z: 498 $[M+Na]^+$;

HRMS (ESI) m/z: Calcd for $C_{23}H_{49}N_3NaO_5Si$: 498.3334; Found: 498.3339 $[M+Na]^+$.

(16-2) Synthesis of 21-azido-3,6,9,12-tetraoxaheneicosan-1-ol (Compound (12c))

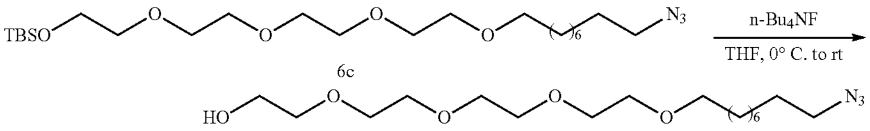

6c

12c

Under an argon atmosphere, to a solution of compound (6c) (398 mg, 0.837 mmol) in dehydrated tetrahydrofuran (8.37 mL) was added dropwise, under ice-cooling, tetra-n-butylammonium fluoride (about 1.00M tetrahydrofuran solution, 8.37 mL, 8.37 mmol), and the mixture was stirred at room temperature for 1 hr. To the reaction mixture was added saturated aqueous ammonium chloride solution at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=1:1→1:2) to give 21-azido-3,6,9,12-tetraoxaheneicosan-1-ol (compound (12c)) (281 mg, 93%) as a pale-yellow oil.

$^1$H NMR (500 MHz, $CDCl_3$) δ: 1.25-1.39 (m, 10H), 1.55-1.62 (m, 4H), 2.84 (br, 1H), 3.26 (t, 2H, J=7.0 Hz), 3.45 (t, 2H, J=6.8 Hz), 3.58-3.74 (m, 16H);

$^{13}$C NMR (75 MHz, $CDCl_3$) δ: 25.9, 26.6, 28.7, 29.0, 29.2, 29.3, 29.5, 51.3, 61.6, 69.9, 70.2, 70.42, 70.44, 70.47, 70.48, 71.4, 72.5;

IR (ATR) $cm^{-1}$: 3456, 2092;

MS (ESI) m/z: 384 $[M+Na]^+$;

HRMS (ESI) m/z: Calcd for $C_{17}H_{35}N_3NaO_5$: 384.2469; Found: 384.2471 $[M+Na]^+$.

(16-3) Synthesis of 1-azido-10,13,16,19,22-pentaoxadotriacontane (Compound (13c))

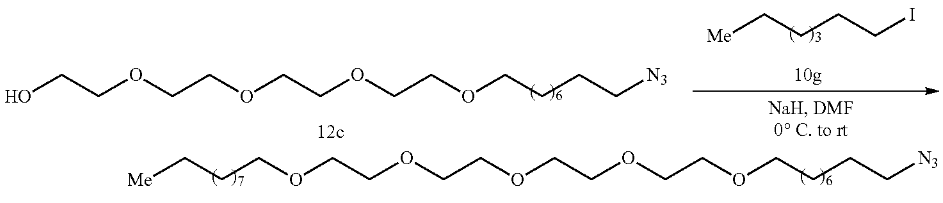

12c

13c

Under a nitrogen atmosphere, to a solution of compound (12c) (171 mg, 0.473 mmol) in dehydrated dimethylformamide (1.58 mL) was added, under ice-cooling, sodium hydride (60% in oil, 37.8 mg, 0.946 mmol), and the mixture was stirred at the same temperature for 10 min. 1-Iododecane (compound (10g)) (manufactured by Tokyo Chemical Industry Co., Ltd.) (0.211 mL, 0.946 mmol) was added thereto at room temperature, and the mixture was stirred at room temperature for 18 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane:ethyl acetate=5:1) to give 1-azido-10,13,16,19,22-pentaoxadotriacontane (compound (13c)) (191 mg, 81%) as a clear colorless oil.

$^1$H NMR (500 MHz, $CDCl_3$) δ: 0.88 (t, 3H, J=7.0 Hz), 1.26-1.38 (m, 24H), 1.55-1.69 (m, 6H), 3.26 (t, 2H, J=7.0 Hz), 3.45 (t, 4H, J=6.8 Hz), 3.57-3.60 (m, 4H), 3.62-3.66 (m, 12H);

$^{13}C$ NMR (75 MHz, $CDCl_3$) δ: 14.1, 22.6, 25.97, 26.02, 26.6 (2C), 28.8, 29.0, 29.25, 29.28, 29.33, 29.4, 29.50, 29.54, 29.6, 31.8, 51.4, 70.0 (2C), 70.52 (2C), 70.54 (2C), 71.4 (2C), 71.5 (2C);

IR (ATR) $cm^{-1}$: 2093, 1106;

MS (ESI) m/z: 524 $[M+Na]^+$;

HRMS (ESI) m/z: Calcd for $C_{27}H_{55}N_3NaO_5$: 524.4034; Found: 524.4035 $[M+Na]^+$.

(16-4) Synthesis of Compound (I-16)

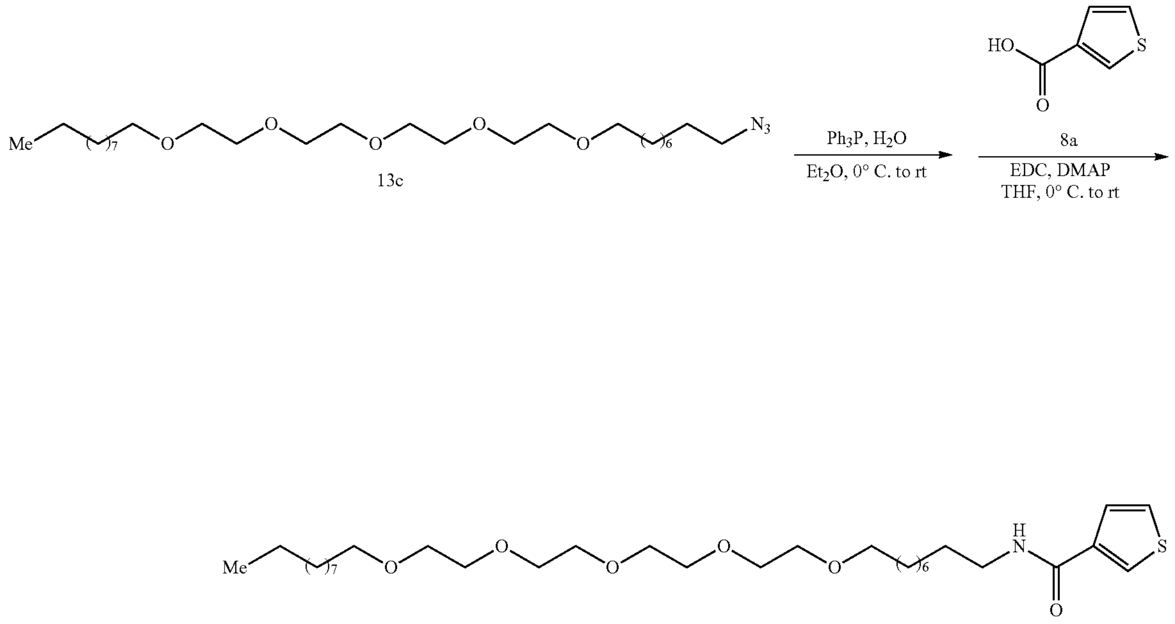

13c

I-16

To a solution of compound (13c) (169 mg, 0.337 mmol) in diethyl ether/water (1:1, 3.37 mL) was added triphenylphosphine (177 mg, 0.674 mmol) at room temperature, and the mixture was stirred at the same temperature for 68 hr. 3M Aqueous sodium hydroxide solution was added at room temperature, and the mixture was extracted with diethyl ether and dried over anhydrous sodium sulfate. The solvent was evaporated under reduced pressure. Under an argon atmosphere, to a solution of the residue in dehydrated tetrahydrofuran (6.74 mL) were added, under ice-cooling, 3-thiophenecarboxylic acid (compound (8a)) (144 mg, 1.01 mmol), 1-ethyl-3-(3-dimethylaminopropyl)carbodiimide hydrochloride (194 mg, 1.01 mmol) and N,N-dimethyl-4-aminopyridine (123 mg, 1.01 mmol), and the mixture was stirred at room temperature for 3 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=2:1→1:1) to give the title compound (compound (I-16)) (165 mg, 84%) as a white waxy solid.

M.p. 50.5-52.3° C.;

$^1H$ NMR (500 MHz, $CDCl_3$) δ: 0.88 (t, 3H, J=7.0 Hz), 1.23-1.40 (m, 24H), 1.55-1.63 (m, 6H), 3.43 (td, 2H, J=7.2, 6.0 Hz), 3.45 (t, 4H, J=6.8 Hz), 3.57-3.60 (m, 4H), 3.62-3.66 (m, 12H), 5.96 (br, 1H), 7.34 (dd, 1H, J=5.1, 3.1 Hz), 7.38 (dd, 1H, J=5.1, 1.3 Hz), 7.85 (dd, 1H, J=3.1, 1.3 Hz);

$^{13}C$ NMR (75 MHz, $CDCl_3$) δ: 14.0, 22.6, 25.9, 26.0, 26.8, 29.1, 29.21, 29.24, 29.3, 29.4 (2C), 29.45 (2C), 29.49, 29.6, 31.8, 39.7, 69.90, 69.91, 70.4 (3C), 70.5 (2C), 71.36, 71.43 (2C), 126.09, 126.10, 127.8, 137.7, 163.0;

IR (ATR) $cm^{-1}$: 3332, 1622;

MS (EI) m/z (%): 585 (78.3) $[M]^+$, 268 (69.6), 252 (71.2), 111 (100.0);

HRMS (EI) m/z: Calcd for $C_{32}H_{59}NO_6S$: 585.4063; Found: 585.4064 $[M]^+$.

Example 17

Synthesis of N-(13,16,19,22-tetraoxaoctacosan-1-yl)-1-methylpyrazole-5-carboxamide (Compound (I-17))

I-17

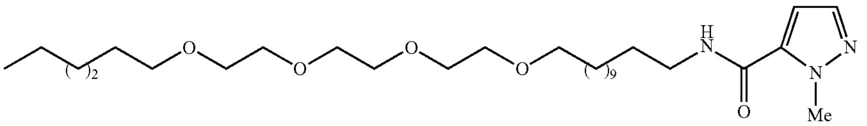

(17-1) Synthesis of 1-azido-13,16,19,22-tetraoxaoctacosane (Compound (13d))

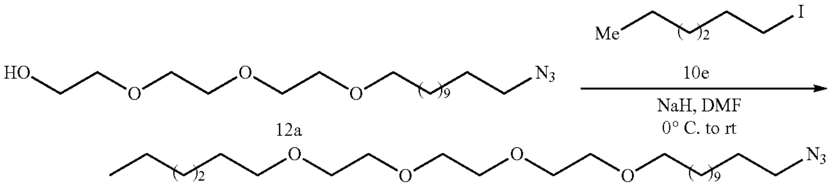

12a

13d

Under an argon atmosphere, to a solution of 21-azido-3,6,9-trioxa-1-heneicosanol (compound (12a)) (167 mg, 0.464 mmol) obtained in Example 8 (8-1) in dehydrated dimethylformamide (2.00 mL) was added, under ice-cooling, sodium hydride (60% in oil, 11.3 mg, 0.464 mmol), and the mixture was stirred at the same temperature for 10 min. Under ice-cooling, 1-iodohexane (compound (10e)) (manufactured by Tokyo Chemical Industry Co., Ltd.) (0.102 mL, 0.696 mmol) was added thereto, and the mixture was stirred at room temperature for 22 hr. To the reaction mixture was added water at room temperature, and the mixture was extracted with ethyl acetate. The organic layer was washed with water and saturated brine, and dried over anhydrous magnesium sulfate. The solvent was evaporated under reduced pressure. The residue was purified by silica gel column chromatography (n-hexane:ethyl acetate=10:1) to give 1-azido-13,16,19,22-tetraoxaoctacosane (compound (13d)) (87.7 mg, 43%) as a clear colorless oil.

$^{1}$H NMR (300 MHz, $CDCl_3$) δ: 0.88 (t, 3H, J=6.8 Hz), 1.27-1.35 (m, 22H), 1.53-1.64 (m, 6H), 3.25 (t, 2H, J=7.0 Hz), 3.45 (t, 4H, J=6.8 Hz), 3.56-3.66 (m, 12H);

$^{13}$C NMR (100 MHz, $CDCl_3$) δ: 14.0, 22.5, 25.7, 26.0, 26.6, 28.7, 29.1, 29.4 (3C), 29.5 (4C), 29.6, 51.4, 70.0 (2C), 70.5 (4C), 71.4 (2C);

IR (ATR) $cm^{-1}$: 2093;

MS (ESI) m/z: 466 $[M]^+$;

HRMS (ESI) m/z: Calcd for $C_{24}H_{49}N_3O_4$: 466.3615; Found: 466.3614 $[M+Na]^+$.

(17-2) Synthesis of Compound (I-17)

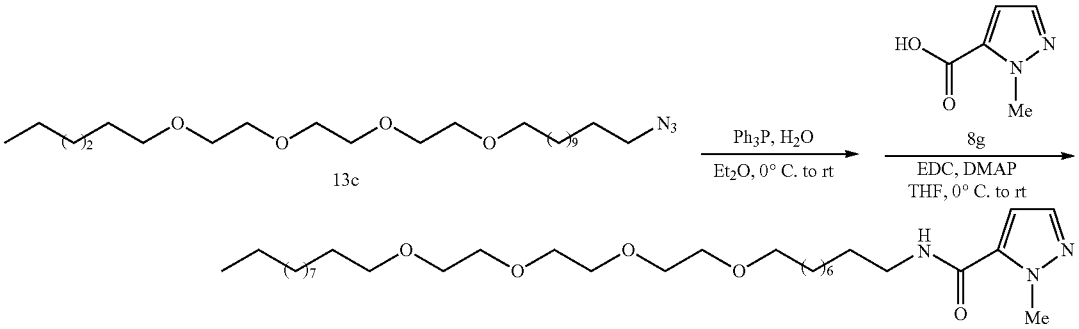

13c

I-17

To a mixed solution of compound (13d) (77.7 mg, 0.175 mmol) in diethyl ether/water (1:1, 3.50 mL) was added triphenylphosphine (69.0 mg, 0.263 mmol) at room temperature, and the mixture was stirred at the same temperature for 69 hr. To the reaction mixture was added, at room temperature, 1M aqueous sodium hydroxide solution to adjust the solution to basic (pH=11), and the mixture was extracted with diethyl ether and dried over anhydrous sodium sulfate. The solvent was evaporated under reduced pressure. Under an argon atmosphere, to a solution of the residue in dehydrated tetrahydrofuran (3.50 mL) were added, under ice-cooling, 1-methylpyrazole-5-carboxylic acid (compound (8g)) (44.1 mg, 0.175 mmol), 1-ethyl-3-(3-dimethylaminopropyl)carbodiimide hydrochloride (192 mg, 0.350 mmol) and N,N-dimethyl-4-aminopyridine (42.8 mg, 0.350 mmol), and the mixture was stirred at room temperature for 3 hr. To the reaction mixture was added water at room temperature, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane→n-hexane:ethyl acetate=5:1) to give the title compound (compound (I-17)) (63.3 mg, 69%) as a clear colorless oil.

$^{1}$H NMR (300 MHz, $CDCl_3$) δ: 0.88 (t, 3H, J=6.7 Hz), 1.22-1.37 (m, 22H), 1.53-1.59 (m, 6H), 3.37 (t, 2H, J=6.8 Hz), 3.44 (t, 4H, J=6.8 Hz), 3.56-3.66 (m, 12H), 4.17 (s, 3H) 6.28 (br, 1H), 6.51 (d, 1H, J=2.0 Hz), 7.42 (d, 1H, J=2.0 Hz);

$^{13}$C NMR (100 MHz, $CDCl_3$) δ: 13.9, 22.5, 25.7, 26.0, 26.9, 29.2, 29.4 (4C), 29.5 (3C), 31.6 (2C), 39.1, 39.5, 70.0 (2C), 70.5 (4C), 71.4 (2C), 105.9, 135.4, 137.4, 160.0;

IR (ATR) $cm^{-1}$: 3324, 1666;

MS (EI) m/z (%): 525 (15.3) $[M]^+$, 416 (25.1), 308 (100.0), 292 (82.2), 138 (38.8), 109 (100.0), 85 (51.2), 43 (75.9);

HRMS (EI) m/z: Calcd for $C_{29}H_{55}N_3O_5$: 525.4142; Found: 525.4141 $[M]^+$.

Example 18

Synthesis of N-(13,16,19,22-tetraoxadotriacontan-1-yl)-1-methylpyrazole-5-carboxamide (Compound (I-18))

I-18

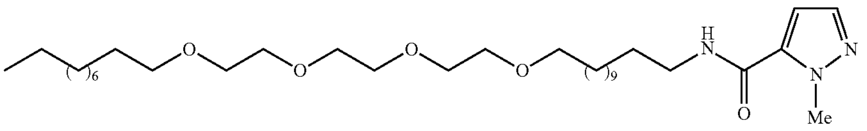

(18-1) Synthesis of 1-azido-13,16,19,22-tetraoxadotriacontane (Compound (13e))

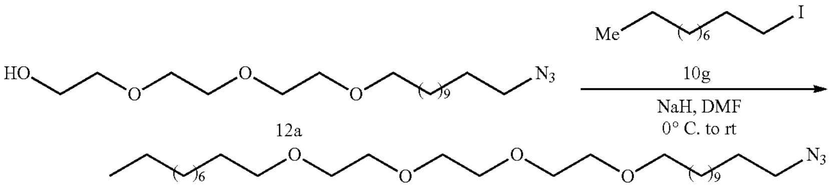

12a

13e

Under a nitrogen atmosphere, to a solution of 21-azido-3,6,9-trioxa-1-heneicosanol (compound (12a)) (104 mg, 0.288 mmol) obtained in Example 8 (8-1) in dehydrated dimethylformamide (0.961 mL) was added, under ice-cooling, sodium hydride (60% in oil, 6.9 mg, 0.288 mmol), and the mixture was stirred at the same temperature for 10 min. Under ice-cooling, 1-iodododecane (compound (10g)) (manufactured by Tokyo Chemical Industry Co., Ltd.) (92.2 μL, 0.432 mmol) was added thereto, and the mixture was stirred at room temperature for 20 hr. To the reaction mixture was added water at room temperature, and the mixture was extracted with ethyl acetate. The organic layer was washed with water and saturated brine, and dried over anhydrous magnesium sulfate. The solvent was evaporated under reduced pressure. The residue was purified by silica gel column chromatography (n-hexane:ethyl acetate=30:1→10:1) to give 1-azido-13,16,19,22-tetraoxadotriacontane (compound (13e)) as a clear colorless oil (86.5 mg, 60%).

$^1$H NMR (300 MHz, $CDCl_3$) δ: 0.88 (t, 3H, J=6.7 Hz), 1.22-1.38 (m, 30H), 1.53-1.62 (m, 6H), 3.26 (t, 2H, J=7.0 Hz), 3.45 (t, 4H, J=6.8 Hz), 3.56-3.66 (m, 12H);

$^{13}$C NMR (100 MHz, $CDCl_3$) δ: 14.0, 22.6, 25.7, 26.0, 26.6, 28.8 (2C), 29.0 (3C), 29.3 (4C), 29.5 (2C), 29.6, 29.7, 31.8, 51.4, 70.0 (2C), 70.5 (4C), 71.4 (2C);

IR (ATR) $cm^{-1}$: 2093;

MS (ESI) m/z: 522 $[M+Na]^+$;

HRMS (ESI) m/z: Calcd for $C_{28}H_{57}N_3O_4$: 522.4241; Found: 522.4250 $[M+Na]^+$.

(18-2) Synthesis of Compound (I-18)

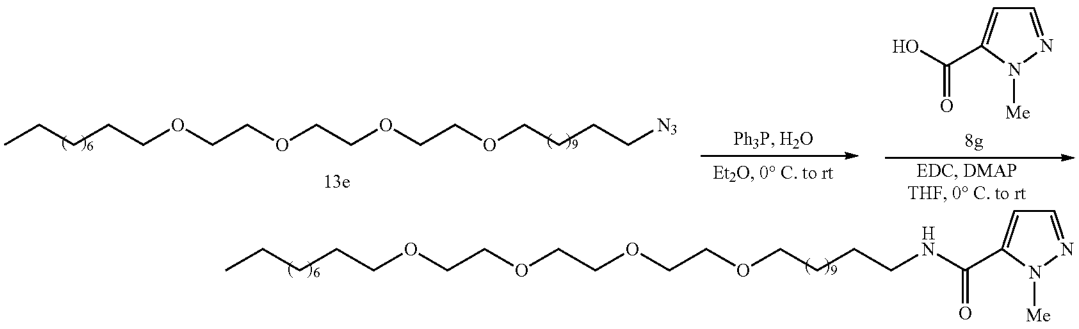

13e

I-18

To a mixed solution of compound (13e) (127 mg, 0.283 mmol) in diethyl ether/water (1:1, 2.83 mL) was added triphenylphosphine (112 mg, 0.424 mmol) at room temperature, and the mixture was stirred at the same temperature for 24 hr. To the reaction mixture was added 1M aqueous sodium hydroxide solution at room temperature, and the mixture was extracted with diethyl ether. The solvent was evaporated under reduced pressure. Under a nitrogen atmosphere, to a solution of the residue in dehydrated tetrahydrofuran (2.84 mL) were added, under ice-cooling, 1-methylpyrazole-5-carboxylic acid (compound (8g)) (357 mg, 2.83 mmol), 1-ethyl-3-(3-dimethylaminopropyl)carbodiimide hydrochloride (543 mg, 2.83 mmol) and N,N-dimethyl-4-aminopyridine (346 mg, 2.83 mmol), and the mixture was stirred at room temperature for 23 hr. Then, water was added thereto, and the mixture was extracted with ethyl acetate. The organic layer was washed with water and saturated brine, and dried over anhydrous sodium sulfate. The solvent was evaporated under reduced pressure. The residue was purified by silica gel column chromatography (n-hexane→n-hexane:ethyl acetate=2:1) to give the title compound (compound (I-18)) as a white solid (86.8 mg, 53%).

M.p. 35.8° C.-38.6° C.;

$^1$H NMR (400 MHz, $CDCl_3$) δ: 0.86 (t, 3H, J=6.7 Hz), 1.18-1.32 (m, 30H), 1.52-1.61 (m, 6H2), 3.52-3.45 (m, 6H), 3.55-3.65 (m, 12H), 4.16 (s, 3H) 5.95 (br, 1H), 6.45 (d, 1H, J=2.0 Hz), 7.42 (d, 1H, J=2.0 Hz);

$^{13}$C NMR (100 MHz, $CDCl_3$) δ: 14.1, 22.6, 26.0, 26.1, 26.9, 29.2, 29.3 (2C), 29.4 (4C), 29.5 (4C), 29.7 (2C), 31.8, 39.2, 39.5, 70.0, 70.5 (4C), 70.9 (2C), 71.5, 105.9, 135.4, 137.4, 160.0;

IR (ATR) $cm^{-1}$: 3271, 1641;

MS (EI) m/z (%): 581 (8.2) [M]Y, 308 (78.4), 270 (69.0), 109 (100.0);

HRMS (EI) m/z: Calcd for $C_{33}H_{63}N_3O_5$: 581.4768; Found: 581.4768 $[M]^+$.

Example 19

Synthesis of N-(13,16,19,22-tetraoxadotriacontan-1-yl)2-methylpyrazole-3-sulfonamide (I-19)

To a mixed solution of compound (13e) (50.0 mg, 0.100 mmol) in diethyl ether/water (1:1, 1.00 mL) was added triphenylphosphine (39.3 mg, 0.150 mmol) at room temperature, and the mixture was stirred at the same temperature for 23 hr. To the reaction mixture was added 3M aqueous sodium hydroxide solution at room temperature, and the mixture was extracted with diethyl ether. The organic layer was dried over anhydrous sodium sulfate and the solvent was evaporated under reduced pressure. Under a nitrogen atmosphere, to a solution of the residue in dehydrated dichloromethane (1.00 mL) were added, at room temperature, 3-methylpyrazole-2-sulfonyl chloride (compound (8h)) (27.1 mg, 0.150 mmol) obtained in Reference Example 6 and distilled triethylamine (0.419 mL, 0.300 mmol), and the mixture was stirred at room temperature for 19 hr. To the reaction mixture was added water at room temperature, and the mixture was extracted with dichloromethane. The organic layer was washed with saturated brine, and dried over anhydrous sodium sulfate. The solvent was evaporated under reduced pressure. The residue was purified by silica gel column chromatography (n-hexane→n-hexane:ethyl acetate=5:1→3:1) to give N-(13,16,19,22-tetraoxadotriacontan-1-yl)2-methylpyrazole-3-sulfonamide (compound (I-19)) (57.9 mg, 94%) as a white waxy solid.

M.p. 40° C. or lower;

$^1$H NMR (300 MHz, $CDCl_3$) δ: 0.86 (t, 3H, J=6.7 Hz), 1.22-1.32 (m, 30H), 1.48 (qn, 2H, J=6.7 Hz), 1.56 (qn, 4H, J=6.7 Hz), 3.04 (q, 2H, J=6.7 Hz), 3.45 (t, 4H, J=6.7 Hz), 3.55-3.58 (m, 4H), 3.61-6.65 (m, 8H), 4.08 (s, 3H), 4.89 (br s, 1H), 6.74 (d, 1H, J=2.0 Hz), 7.45 (d, 1H, J=2.0 Hz);

$^{13}$C NMR (75 MHz, $CDCl_3$) δ: 14.1, 22.6, 26.0, 26.1, 26.4, 29.0, 29.3, 29.35, 29.40 (2C), 29.44, 29.45 (2C), 29.48, 29.54, 29.57 (2C), 29.63, 31.9, 38.5, 43.3, 70.0, 70.56, 70.57 (2C), 71.50 (2C), 71.52 (2C), 111.0, 137.6, 139.0;

IR (ATR) $cm^{-1}$: 3291, 1325, 1143;

MS (FAB): m/z (%) 618 $[M+H]^+$;

HRMS (FAB): m/z $[M+H]^+$ calcd for $C_{32}H_{64}N_3O_6S$: 618.4516; found: 618.4511.

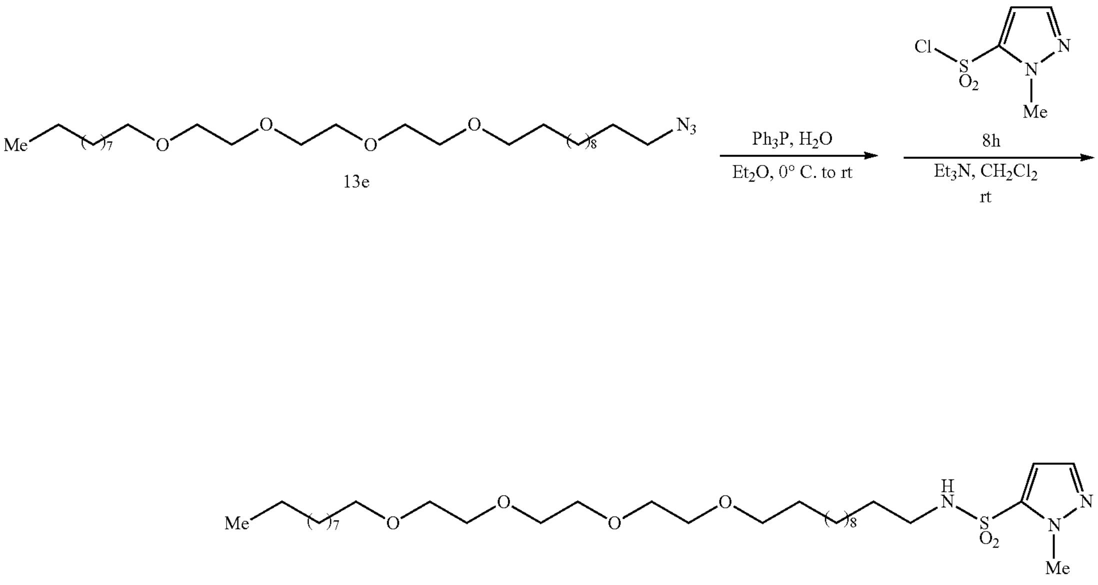

13e

I-19

Example 20

Synthesis of N-(13,16,19,22-tetraoxadotriacontan-1-yl)thiophene-2-carboxamide (I-20)

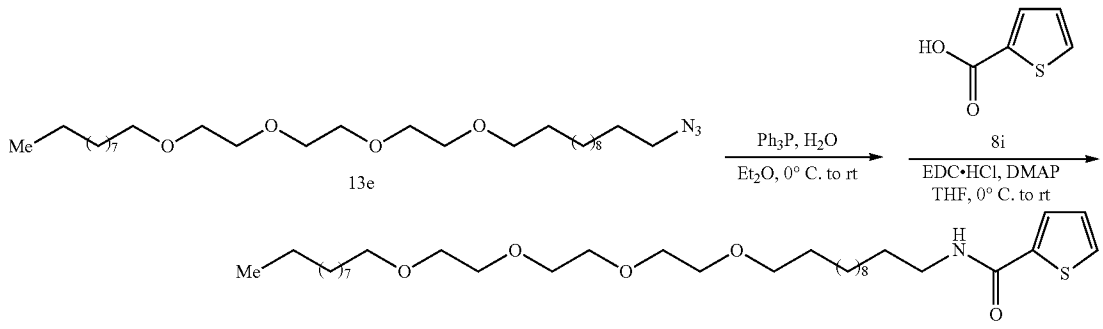

13e

I-20

To a mixed solution of compound (13e) (50.0 mg, 0.100 mmol) in diethyl ether/water (1:1, 1.00 mL) was added triphenylphosphine (39.3 mg, 0.150 mmol) at room temperature, and the mixture was stirred at the same temperature for 26 hr. To the reaction mixture was added 1M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated tetrahydrofuran (2.00 mL) were added, under ice-cooling, 2-thiophenecarboxylic acid (compound (8i)) (manufactured by Tokyo Chemical Industry Co., Ltd.) (25.6 mg, 0.200 mmol), 1-ethyl-3-(3-dimethylaminopropyl)carbodiimide hydrochloride (38.3 mg, 0.200 mmol) and N,N-dimethyl-4-aminopyridine (24.4 mg, 0.200 mmol), and the mixture was stirred at room temperature for 17 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=5:1) to give N-(13,16,19,22-tetraoxadotriacontan-1-yl)thiophene-2-carboxamide (compound (I-20)) (50.3 mg, 86%) as a white waxy solid.

M.p. 42.1-43.3° C.;

$^{1}H$ NMR (300 MHz, $CDCl_3$) δ: 0.87 (t, 3H, J=6.9 Hz), 1.25-1.38 (m, 30H), 1.57 (qn, 4H), 1.60 (qn, 2H), 3.41 (t, 2H, J=6.9 Hz), 3.44 (t, 4H, J=6.9 Hz), 3.56-3.58 (m, 4H), 3.63-3.66 (m, 8H), 5.98 (br s, 1H), 7.07 (dd, 1H, J=5.0, 3.8 Hz), 7.46 (d, 1H, J=5.0 Hz), 7.48 (d, 1H, J=3.8 Hz);

$^{13}C$ NMR (75 MHz, $CDCl_3$) δ: 14.1, 22.7, 26.0, 26.1, 26.9, 29.26, 29.29, 29.4, 29.46, 29.47, 29.50, 29.51, 29.52, 29.53, 29.58, 29.59, 29.65, 29.66, 31.9, 40.0, 70.0 (2C), 70.57 (2C), 70.59 (2C), 71.5 (2C), 127.5, 127.7, 129.5, 139.2, 161.8;

IR (ATR) $cm^{-1}$: 3321, 1622;

MS (EI): m/z (%) 584 (13.6) $[M+H]^+$, 472 (7.5), 310 (83.9), 294 (66.1), 111 (100), 83 (13.7);

HRMS (EI) m/z: Calcd for $C_{33}H_{61}NO_5S$: 583.4270; found: 583.4268 $[M]^+$.

Example 21

Synthesis of N-(13,16,19,22-tetraoxadotriacontan-1-yl)pyrimidine-4-carboxamide (I-21)

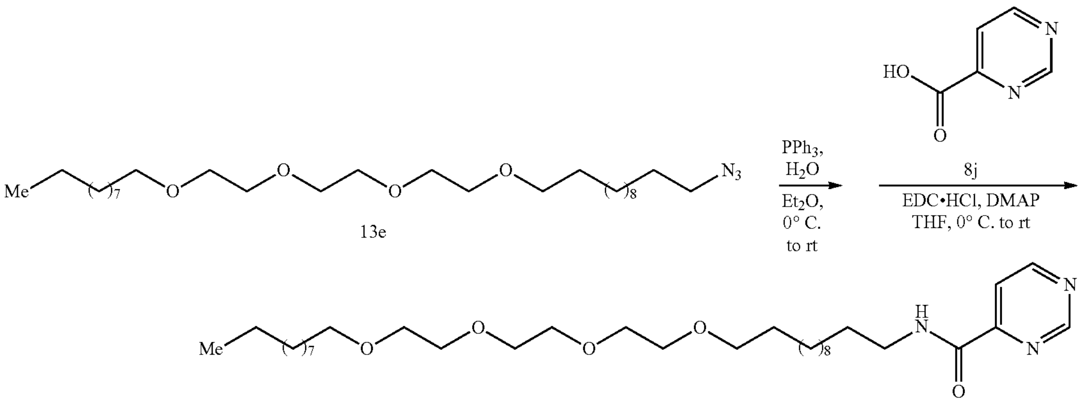

13e

I-21

To a mixed solution of compound (13e) (50.0 mg, 0.100 mmol) in diethyl ether/water (1:1, 1.00 mL) was added triphenylphosphine (39.3 mg, 0.150 mmol) at room temperature, and the mixture was stirred at the same temperature for 18 hr. To the reaction mixture was added 1M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated tetrahydrofuran (2.00 mL) were added, under ice-cooling, 4-pyrimidinecarboxylic acid (compound (8j)) (manufactured by Tokyo Chemical Industry Co., Ltd.) (24.8 mg, 0.200 mmol), 1-ethyl-3-(3-dimethylaminopropyl) carbodiimide hydrochloride (38.8 mg, 0.200 mmol) and N,N-dimethyl-4-aminopyridine (24.4 mg, 0.200 mmol), and the mixture was stirred at room temperature for 16 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=5:1) to give N-(13,16,19,22-tetraoxadotriacontan-1-yl)pyrimidine-4-carboxamide (compound (I-21)) (56.8 mg, 98%) as a white waxy solid.

M.p. 46.9-47.5° C.;

$^{1}$H NMR (300 MHz, $CDCl_3$) δ: 0.88 (t, 3H, J=6.7 Hz), 1.26-1.41 (m, 30H), 1.53-1.69 (m, 6H), 3.42-3.51 (m, 6H), 3.56-3.60 (m, 4H), 3.63-3.66 (m, 8H), 8.00 (br s, 1H), 8.13 (dd, 1H, J=5.2, 1.2 Hz), 8.97 (d, 1H, J=5.2 Hz), 9.23 (d, 1H, J=1.2 Hz);

$^{13}$C NMR (75 MHz, $CDCl_3$) δ: 14.1, 22.7, 26.1, 26.9, 29.27, 29.31, 29.45, 29.48, 29.49, 29.55, 29.56, 29.60, 29.62 (4C), 29.7 (2C), 31.9, 39.6, 70.0 (2C), 70.60 (2C), 70.62 (2C), 71.5 (2C), 118.5, 156.4, 157.7, 159.2, 162.5;

IR (ATR) $cm^{-1}$: 3364, 1656;

MS (ESI) m/z: 602 $[M+Na]^+$;

HRMS (FAB) m/z: Calcd for $C_{33}H_{61}N_3NaO_5$: 602.4509; found: 602.4504 $[M+Na]^+$.

Example 22

Synthesis of N-(13,16,19,22-tetraoxadotriacontan-1-yl)thiophene-3-sulfonamide (I-22)

To a mixed solution of compound (13e) (50.0 mg, 0.100 mmol) in diethyl ether/water (1:1, 1.00 mL) was added triphenylphosphine (39.3 mg, 0.150 mmol) at room temperature, and the mixture was stirred at the same temperature for 18 hr. To the reaction mixture was added 1M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated dichloromethane (1.00 mL) were added, at room temperature, 3-thiophenesulfonyl chloride (compound (8k)) (manufactured by combi-Blocks Inc.) (27.4 mg, 0.150 mmol) and distilled triethylamine (0.419 mL, 0.300 mmol), and the mixture was stirred at the same temperature for 19 hr. To the reaction mixture was added water at room temperature, and the mixture was extracted with dichloromethane. The organic layer was washed with saturated brine, and dried over anhydrous sodium sulfate. The solvent was evaporated under reduced pressure. The residue was purified by silica gel column chromatography (n-hexane:ethyl acetate=5:1) to give N-(13,16,19,22-tetraoxadotriacontan-1-yl)thiophene-3-sulfonamide (compound (I-22)) (21.4 mg, 35%) as a white waxy solid.

M.p. 40.6-41.7° C.;

$^{1}$H NMR (300 MHz, $CDCl_3$) δ: 0.88 (t, 3H, J=6.7 Hz), 1.22-1.33 (m, 30H), 1.42-1.58 (m, 6H), 3.00 (q, 2H, J=6.8 Hz), 3.45 (t, 4H, J=6.9 Hz), 3.56-3.60 (m, 4H), 3.63-3.66 (m, 8H), 4.33 (br t, 1H, J=6.0 Hz), 7.36 (dd, 1H, J=5.1, 1.3 Hz), 7.43 (dd, 1H, J=5.1, 3.0 Hz), 7.96 (dd, 1H, J=3.0, 1.3 Hz);

$^{13}$C NMR (75 MHz, $CDCl_3$) δ: 14.1, 22.7, 26.07, 26.08, 26.5, 29.0, 29.3, 29.4, 29.46, 29.49 (2C), 29.53, 29.57 (2C), 29.60, 29.62 (2C), 29.7, 31.9, 43.3, 70.0 (2C), 70.61 (2C), 70.62 (2C), 71.5, 71.6, 125.4, 127.9, 130.3, 140.1;

IR (ATR) $cm^{-1}$: 3277, 1320, 1146;

MS (ESI) m/z: 642 $[M+Na]^+$;

HRMS (ESI) m/z: Calcd for $C_{32}H_{61}NNaO_6S_2$: 642.3838; found: 642.3837 $[M+Na]^+$.

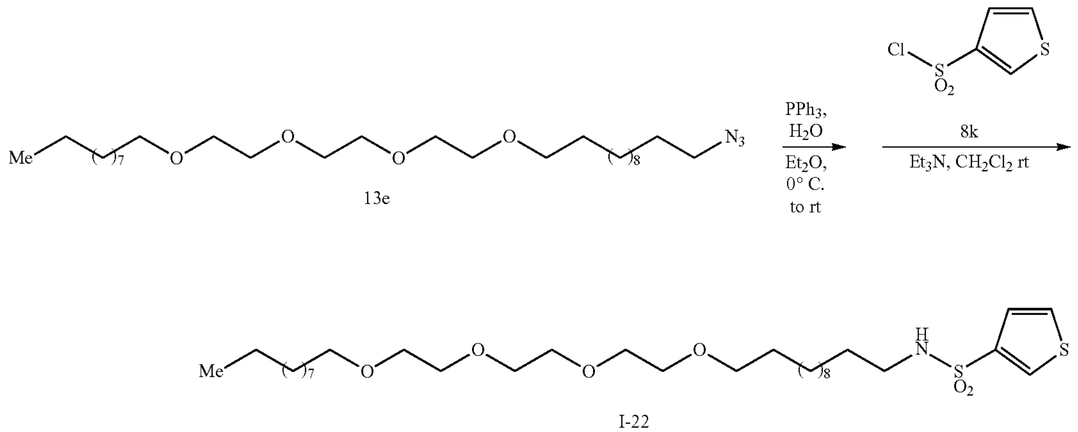

I-22

Example 23

Synthesis of N-(13,16,19,22-tetraoxadotriacontan-1-yl)thiophene-2-sulfonamide (I-23)

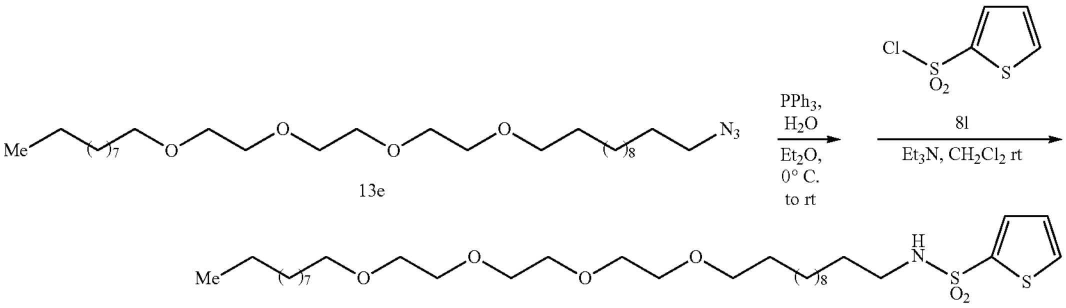

I-22

To a mixed solution of compound (13e) (354 mg, 0.708 mmol) in diethyl ether/water (1:1, 7.10 mL) was added triphenylphosphine (300 mg, 1.06 mmol) at room temperature, and the mixture was stirred at the same temperature for 24 hr. To the reaction mixture was added 1M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated dichloromethane (13.4 mL) were added, at room temperature, 2-thiophenesulfonyl chloride (compound (81)) (manufactured by Tokyo Chemical Industry Co., Ltd.) (369 mg, 2.02 mmol) and distilled triethylamine (0.564 mL, 4.04 mmol), and the mixture was stirred at the same temperature for 17 hr. To the reaction mixture was added water at room temperature, and the mixture was extracted with dichloromethane. The organic layer was washed with saturated brine, and the solvent was evaporated under reduced pressure. The residue was purified by silica gel column chromatography (n-hexane:ethyl acetate=5:1) to give N-(13,16,19,22-tetraoxadotriacontan-1-yl)thiophene-2-sulfonamide (compound (I-23)) (209 mg, 48%) as a white waxy solid.

M.p. 40° C. or lower;

$^{1}$H NMR (300 MHz, $CDCl_3$) δ: 0.88 (t, 3H, J=6.7 Hz), 1.23-1.33 (m, 30H), 1.44-1.60 (m, 6H), 3.04 (q, 2H, J=6.9 Hz), 3.45 (t, 4H, J=6.9 Hz), 3.56-3.60 (m, 4H), 3.63-3.66 (m, 8H), 4.43 (br t, 1H, J=6.0 Hz), 7.10 (dd, 1H, J=3.7, 1.4 Hz), 7.59 (dd, 1H, J=5.0, 1.4 Hz), 7.61 (dd, 1H, J=5.0, 3.7 Hz);

$^{13}$C NMR (75 MHz, $CDCl_3$) δ: 14.1, 22.7, 26.06, 26.08, 26.5, 29.0, 29.3, 29.4, 29.45 (3C), 29.49 (2C), 29.53, 29.57, 29.61, 29.62, 29.7, 31.9, 43.5, 70.0 (2C), 70.6 (2C), 71.5 (2C), 71.6 (2C), 127.3, 131.7, 132.0, 141.0;

IR (ATR) $cm^{-1}$: 3269, 1336, 1155;

MS (ESI) m/z: 642 $[M+Na]^+$;

HRMS (ESI) m/z: Calcd for $C_{32}H_{61}NNaO_6S_2$: 642.3838; found: 642.3827 $[M+Na]^+$.

Example 24

Synthesis of N-(13,16,19-trioxanonacosan-1-yl)thiophene-3-carboxamide (Compound (I-24))

I-24

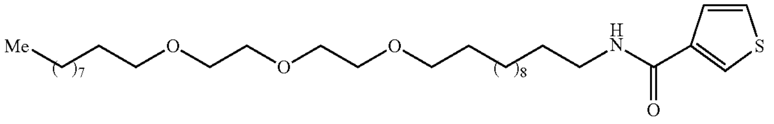

(24-1) Synthesis of 3,6-dioxa-1-hexadecanol (compound (15b))

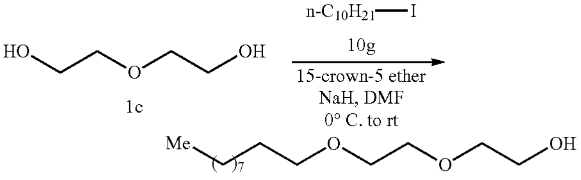

15b

Under a nitrogen atmosphere, to a solution of diethylene glycol (Nacalai Tesque) (compound (1c)) (0.893 mL, 9.42 mmol) in dehydrated dimethylformamide (9.42 mL) were added, under ice-cooling, sodium hydride (manufactured by Tokyo Chemical Industry Co., Ltd.) (60% in oil, 565 mg, 14.1 mmol) and 15-crown-5 ether (manufactured by Tokyo Chemical Industry Co., Ltd.) (1.87 mL, 9.42 mmol), and the mixture was stirred for 10 min. To the reaction mixture was added at the same temperature 1-iododecane (compound (10g)) (manufactured by Tokyo Chemical Industry Co., Ltd.) (3.00 mL, 14.1 mmol) over 30 min, and the mixture was stirred at room temperature for 23 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane→n-hexane:ethyl acetate=2:1) to give 3,6-dioxa-1-hexadecanol (compound (15b)) (873 mg, 38%) as a clear pale-yellow oil.

$^1$H NMR (500 MHz, $CDCl_3$) δ: 0.88 (t, 3H, J=6.7 Hz), 1.24-1.35 (m, 14H), 1.59 (qn, 2H, J=6.8 Hz), 2.51 (t, 1H, J=6.2 Hz), 3.47 (t, 2H, J=6.9 Hz), 3.57-3.76 (m, 8H);

$^{13}$C NMR (75 MHz, $CDCl_3$) δ: 14.1, 22.7, 26.1, 29.3, 29.5, 29.56, 29.57, 29.58, 31.9, 61.9, 70.2, 70.5, 71.6, 72.5;

IR (ATR) $cm^{-1}$: 3424;

MS (FAB) m/z: 247 $[M+H]^+$;

HRMS (FAB) m/z: Calcd for $C_{14}H_{31}O_3$: 247.2273; found: 247.2272 $[M+H]^+$.

(24-2) Synthesis of 1-azido-13,16,19-trioxanonacosane (Compound (13f)

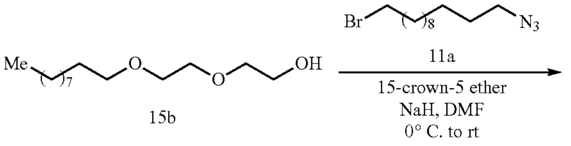

15b

-continued

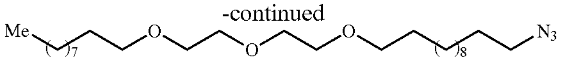

13f

Under a nitrogen atmosphere, to a solution of compound (15b) (873 mg, 3.54 mmol) in dehydrated dimethylformamide (10.0 mL) were added, under ice-cooling, 15-crown-5 ether (manufactured by Tokyo Chemical Industry Co., Ltd.) (1.41 mL, 7.08 mmol) and sodium hydride (manufactured by Tokyo Chemical Industry Co., Ltd.) (60% in oil, 283 mg, 7.08 mmol), and the mixture was stirred for 10 min. To the reaction mixture was added a solution of 1-azido-12-bromododecane (compound (11a)) (1.54 g, 5.31 mmol) in dehydrated dimethylformamide (1.80 mL) at the same temperature, and the mixture was stirred at room temperature for 23 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=30:1→10:1) to give 1-azido-13,16,19-trioxanonacosane (compound (13f)) (1.38 g, 71%) as a clear pale-yellow oil.

$^1$H NMR (500 MHz, $CDCl_3$) δ: 0.88 (t, 3H, J=7.0 Hz), 1.26-1.37 (m, 30H), 1.55-1.62 (m, 6H), 3.26 (t, 2H, J=7.0 Hz), 3.45 (t, 4H, J=6.8 Hz), 3.58-3.60 (m, 4H), 3.64-3.66 (m, 4H);

$^{13}$C NMR (75 Hz, $CDCl_3$) δ: 14.1, 22.7, 26.1 (2C), 26.7, 28.8, 29.1, 29.3, 29.45, 29.48, 29.51, 29.53, 29.54, 29.56 (2C), 29.60, 29.64 (2C), 31.9, 51.5, 70.1 (2C), 70.6 (2C), 71.5 (2C);

IR (ATR) $cm^{-1}$: 2094;

MS (FAB): m/z (%) 456 $[M+H]^+$;

HRMS (FAB) m/z: Calcd for $C_{26}H_{54}N_3O_3$: 456.4165; found: 456.4161 $[M+H]^+$.

(24-3) Synthesis of Compound (I-24)

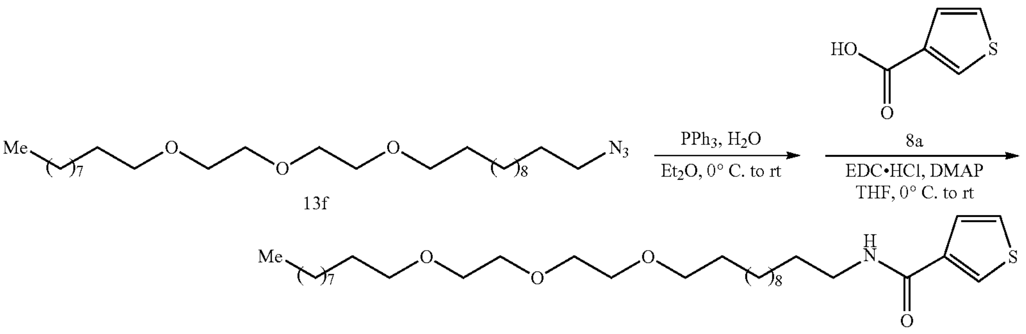

13f

I-24

To a mixed solution of compound (13f) (200 mg, 0.434 mmol) in diethyl ether/water (1:1, 4.34 mL) was added triphenylphosphine (231 mg, 0.878 mmol) at room temperature, and the mixture was stirred at the same temperature for 44 hr. To the reaction mixture was added 3M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated tetrahydrofuran (8.68 mL) were added, under ice-cooling, 3-thiophenecarboxylic acid (compound (8a)) (manufactured by FUJIFILM Wako Pure Chemical Corporation) (185 mg, 1.30 mmol), 1-ethyl-3-(3-dimethylaminopropyl)carbodiimide hydrochloride (250 mg, 1.30 mmol) and N,N-dimethyl-4-aminopyridine (159 mg, 1.30 mmol), and the mixture was stirred at room temperature for 18 hr. To the reaction mixture was added water at room temperature, and the mixture was extracted with diethyl ether. The organic layer was washed with saturated brine, and dried over anhydrous sodium sulfate. The solvent was evaporated under reduced pressure.

The residue was purified by silica gel column chromatography (n-hexane:ethyl acetate=2:1) to give N-(13,16,19-trioxanonacosan-1-yl)thiophene-3-carboxamide (compound (I-24)) (201 mg, 86%) as a white waxy solid.

M.p. 74.8-75.2° C.;

$^1$H NMR (500 MHz, $CDCl_3$) δ: 0.86 (t, 3H, J=6.7 Hz), 1.24-1.36 (m, 30H), 1.51-1.62 (m, 6H), 3.35-3.45 (m, 6H), 3.55-3.65 (m, 8H), 6.18 (br s, 1H), 7.30 (dd, 1H, J=5.0, 3.0 Hz), 7.37 (dd, 1H, J=5.0, 1.3 Hz), 7.84 (dd, 1H, J=3.0, 1.3 Hz);

$^{13}$C NMR (75 MHz, $CDCl_3$) δ: 14.1, 22.6, 26.0 (2C), 26.9, 29.3 (2C), 29.41, 29.43, 29.47, 29.50 (3C), 29.51, 29.55, 29.57 (2C), 29.7, 31.8, 39.8, 70.0 (2C), 70.6 (2C), 71.5 (2C), 126.0, 126.3, 127.8, 137.8, 163.0;

IR (ATR) $cm^{-1}$: 3330, 1623;

MS (FAB) m/z: 541 $[M+H]^+$;

HRMS (FAB) m/z: Calcd for $C_{31}H_{58}NO_4S$: 540.4087; found: 540.4083 $[M+H]^+$.

Example 25

Synthesis of N-(13,16,19,22,25-pentaoxapentatriacontan-1-yl)thiophene-3-carboxamide (Compound (I-25))

I-25

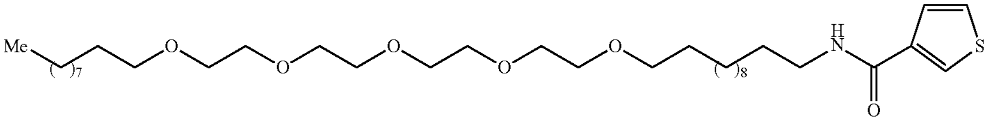

(25-1) Synthesis of 1-azido-13,16,19,22,25-pentaoxapentatriacontane (Compound (13g))

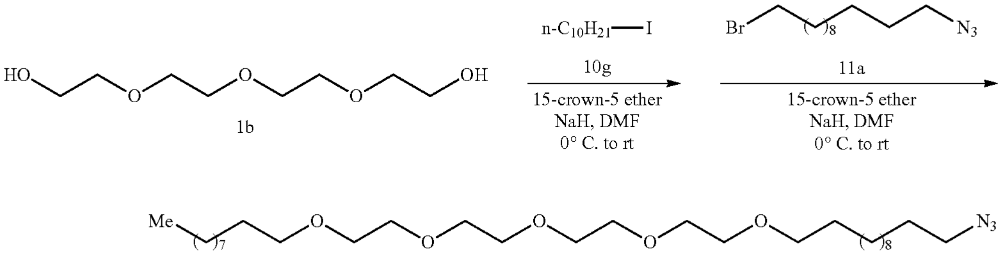

13g

Under a nitrogen atmosphere, to a solution of tetraethylene glycol (FUJIFILM Wako Pure Chemical Corporation) (compound (1b)) (0.885 mL, 5.15 mmol) in dehydrated dimethylformamide (4.2 mL) were added, under ice-cooling, sodium hydride (manufactured by Tokyo Chemical Industry Co., Ltd.) (60% in oil, 309 mg, 7.72 mmol) and 15-crown-5 ether (manufactured by Tokyo Chemical Industry Co., Ltd.) (1.53 mL, 7.72 mmol), and the mixture was stirred for 10 min. To the reaction mixture was added 1-iododecane (compound (10g)) (manufactured by Tokyo Chemical Industry Co., Ltd.) (1.64 mL, 7.72 mmol) at the same temperature, and the mixture was stirred at room temperature for 20 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=10:1→1:1→ethyl acetate) to give 3,6,9,12-tetraoxa-1-tricosanol (681 mg, 40%) as a clear pale-yellow oil. Under a nitrogen atmosphere, to a solution of 3,6,9,12-tetraoxa-1-tricosanol (681 mg, 2.04 mmol) in dehydrated dimethylformamide (3.0 mL) were added, under ice-cooling, sodium hydride (manufactured by Tokyo Chemical Industry Co., Ltd.) (60% in oil, 163 mg, 4.07 mmol) and 15-crown-5 ether (manufactured by Tokyo Chemical Industry Co., Ltd.) (0.809 mL, 4.07 mmol), and the mixture was stirred for 10 min. To the reaction mixture was added a solution of 1-azido-12-bromododecane (compound (11a)) (886 mg, 3.05 mmol) in dehydrated dimethylformamide (3.78 mL) at the same temperature, and the mixture was stirred at room temperature for 20 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=10:1-+1:1) to give 1-azido-13,16,19,22,25-pentaoxapentatriacontane (compound (13g)) (813 mg, 73%) as a clear colorless oil.

$^1$H NMR (500 MHz, $CDCl_3$) δ: 0.86 (t, 3H, J=6.7 Hz), 1.24-1.37 (m, 30H), 1.51-1.63 (m, 6H), 3.24 (t, 2H, J=7.0 Hz), 3.43 (t, 4H, J=6.8 Hz), 3.54-3.58 (m, 4H), 3.61-3.64 (m, 12H);

$^{13}$C NMR (75 MHz, $CDCl_3$) δ: 14.1, 22.6, 26.0, 26.7, 28.8, 29.1, 29.3, 29.41, 29.43, 29.45, 29.46, 29.49, 29.50, 29.52, 29.57, 29.59 (2C), 29.62, 31.9, 51.4, 70.0 (2C), 70.55 (4C), 70.58 (2C), 71.5 (2C);

IR (ATR) $cm^{-1}$: 2092;

MS (FAB) m/z: 544 $[M+H]^+$;

HRMS (FAB) m/z: Calcd for $C_{30}H_{62}N_3O_5$: 544.4689; found: 544.4700 $[M+H]^+$.

(25-2) Synthesis of Compound (I-25)

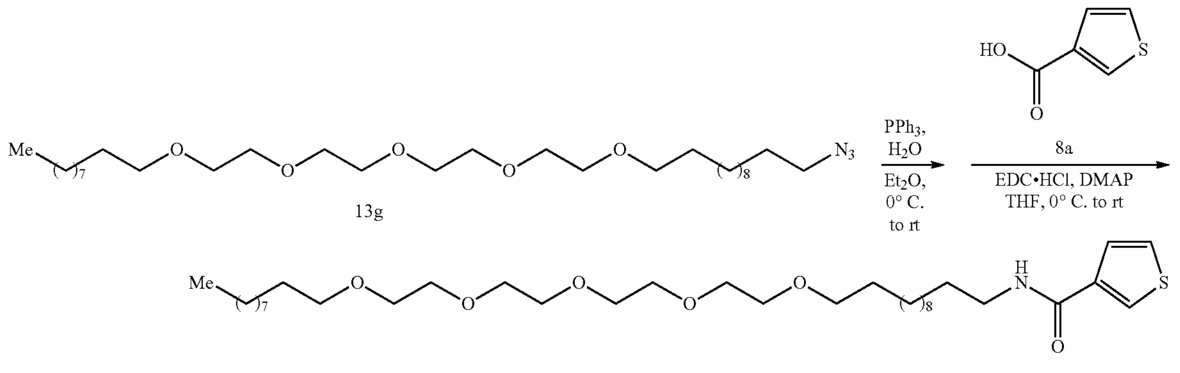

13g

I-25

To a mixed solution of compound (13g) (477 mg, 0.877 mmol) in diethyl ether/water (1:1, 3.68 mL) was added triphenylphosphine (193 mg, 0.736 mmol) at room temperature, and the mixture was stirred at the same temperature for 19 hr. To the reaction mixture was added 1M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated tetrahydrofuran (7.36 mL) were added, under ice-cooling, 3-thiophenecarboxylic acid (compound (8a)) (manufactured by FUJIFILM Wako Pure Chemical Corporation) (141 mg, 1.10 mmol), 1-ethyl-3-(3-dimethylaminopropyl) carbodiimide hydrochloride (212 mg, 1.10 mmol) and N,N-dimethyl-4-aminopyridine (135 mg, 1.10 mmol), and the mixture was stirred at room temperature for 24 hr. To the reaction mixture was added water at room temperature, and the mixture was extracted with chloroform. The organic layer was washed with saturated brine, and dried over anhydrous sodium sulfate. The solvent was evaporated under reduced pressure. The residue was purified by silica gel column chromatography (chloroform→chloroform:methanol=50:1→20:1) to give N-(13,16,19,22,25-pentaoxapentatriacontan-1-yl)thiophene-3-carboxamide (compound (I-25)) (210 mg, 38%) as a white waxy solid.

M.p. 60.2-61.1° C.;

$^1H$ NMR (500 MHz, $CDCl_3$) δ: 0.88 (t, 3H, J=6.7 Hz), 1.26-1.39 (m, 30H), 1.57 (qn, 6H, J=6.7 Hz), 3.38-3.47 (m, 6H), 3.56-3.59 (m, 4H), 3.62-3.66 (m, 12H), 5.93 (br s, 1H) 7.34 (dd, 1H, J=5.1, 3.0 Hz), 7.37 (dd, 1H, J=5.1, 1.5 Hz), 7.84 (dd, 1H, J=3.0, 1.5 Hz);

$^{13}C$ NMR (75 MHz, $CDCl_3$) δ: 14.1, 22.6, 26.0 (2C), 26.9, 29.3 (2C), 29.40, 29.43, 29.45, 29.48 (2C), 29.50, 29.55, 29.56, 29.57 (2C), 29.7, 31.8, 39.8, 70.0 (2C), 70.5 (4C), 70.6 (2C), 71.5 (2C), 126.0, 126.3, 127.8, 137.8, 163.0;

IR (ATR) $cm^{-1}$: 1623;

MS (FAB) m/z: 628 $[M+H]^+$;

HRMS (FAB) m/z: Calcd for $C_{35}H_{66}NO_6S$: 628.4611; found: 628.4619 $[M+H]^+$.

Example 26

Synthesis of N-(13,16,19,22,25,28-hexaoxaoctatriacontan-1-yl)thiophene-3-carboxamide (Compound (I-26))

I-26

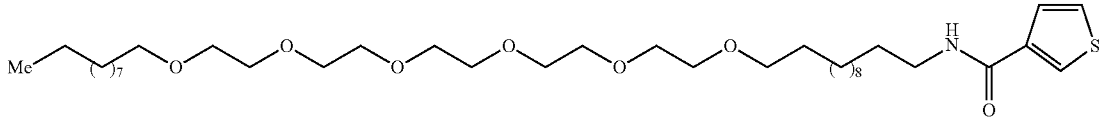

(26-1) Synthesis of 1-azido-13,16,19,22,25,28-hexaoxaoctatriacontane (Compound (13h))

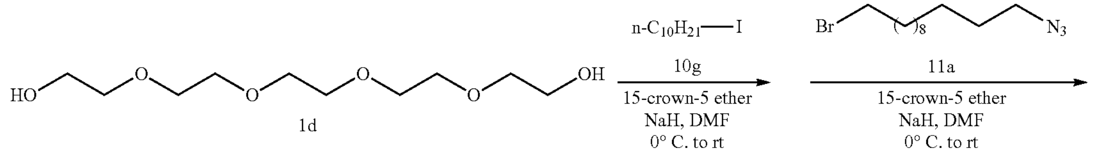

1d

-continued

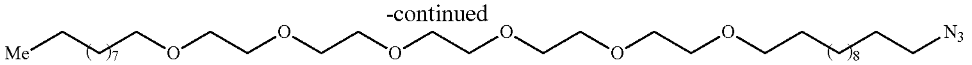

13h

Under a nitrogen atmosphere, to a solution of pentaethylene glycol (FUJIFILM Wako Pure Chemical Corporation) (compound (1d)) (0.885 mL, 4.20 mmol) in dehydrated dimethylformamide (4.2 mL) were added, under ice-cooling, sodium hydride (manufactured by Tokyo Chemical Industry Co., Ltd.) (60% in oil, 252 mg, 6.30 mmol) and 15-crown-5 ether (manufactured by Tokyo Chemical Industry Co., Ltd.) (1.25 mL, 6.30 mmol), and the mixture was stirred at the same temperature for 10 min. To the reaction mixture was added 1-iododecane (compound (10g)) (manufactured by Tokyo Chemical Industry Co., Ltd.) (1.34 mL, 6.30 mmol) at the same temperature, and the mixture was stirred at room temperature for 17 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=10:1-+1:1) to give 3,6,9,12,15-pentaoxa-1-pentacosanol (723 mg, 45%) as a clear pale-yellow oil. Under a nitrogen atmosphere, to a solution of 3,6,9,12,15-pentaoxa-1-pentacosanol (723 mg, 1.91 mmol) in dehydrated dimethylformamide (1.59 mL) were added, under ice-cooling, sodium hydride (manufactured by Tokyo Chemical Industry Co., Ltd.) (60% in oil, 153 mg, 3.82 mmol) and 15-crown-5 ether (manufactured by Tokyo Chemical Industry Co., Ltd.) (0.759 mL, 3.82 mmol), and the mixture was stirred for 10 min. To the reaction mixture was added a solution of 1-azido-12-bromododecane (compound (11a)) (833 mg, 2.87 mmol) in dehydrated dimethylformamide (4.78 mL) at the same temperature, and the mixture was stirred at room temperature for 19 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=10:1→1:1) to give 1-azido-13,16,19,22,25,28-hexaoxaoctatriacontane (compound (13h)) (705 mg, 63%) as a white waxy solid.

M.p. 40° C. or lower;

$^{1}H$ NMR (500 MHz, $CDCl_3$) δ: 0.85 (t, 3H, J=6.8 Hz), 1.24-1.36 (m, 30H), 1.50-1.62 (m, 6H), 3.23 (t, 2H, J=7.0 Hz), 3.42 (t, 4H, J=6.8 Hz), 3.53-3.57 (m, 4H), 3.60-3.63 (m, 16H);

$^{13}C$ NMR (75 MHz, $CDCl_3$) δ: 14.0, 22.6, 26.0 (2C), 26.3, 28.8, 29.1, 29.2, 29.39, 29.40 (2C), 29.43, 29.47, 29.49 (2C), 29.52, 29.6 (2C), 31.8, 51.4, 70.0 (2C), 70.51 (5C), 70.54 (3C), 71.5 (2C);

IR (ATR) $cm^{-1}$: 2094;

MS (FAB) m/z: 610 $[M+Na]^+$;

HRMS (FAB) m/z: Calcd for $C_{32}H_{65}N_3NaO_6$: 610.4771; found: 610.4762 $[M+Na]^+$.

(26-2) Synthesis of Compound (I-26)

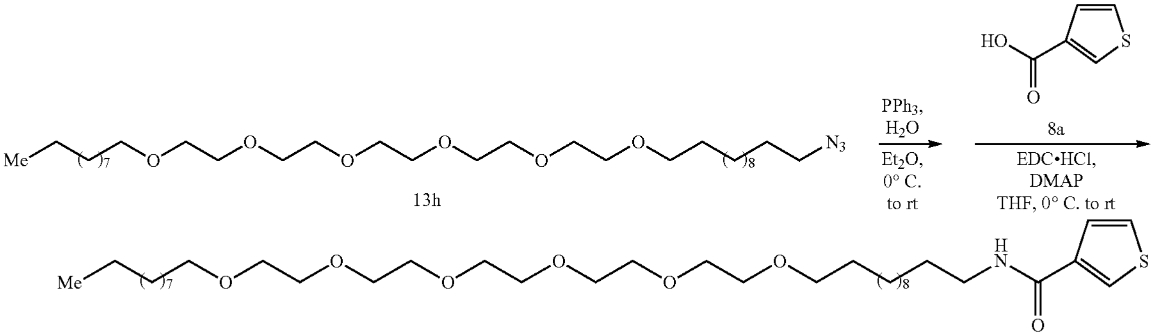

13h

I-26

To a mixed solution of compound (13h) (389 mg, 0.661 mmol) in diethyl ether/water (1:1, 6.8 mL) was added, under ice-cooling, triphenylphosphine (357 mg, 1.36 mmol), and the mixture was stirred at the same temperature for 22.5 hr. To the reaction mixture was added 1M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated tetrahydrofuran (13.6 mL) were added, under ice-cooling, 3-thiophenecarboxylic acid (compound (8a)) (manufactured by FUJIFILM Wako Pure Chemical Corporation) (261 mg, 2.04 mmol), 1-ethyl-3-(3-dimethylaminopropyl) carbodiimide hydrochloride (391 mg, 2.04 mmol) and N,N-dimethyl-4-aminopyridine (249 mg, 2.04 mmol), and the mixture was stirred at room temperature for 20 hr. To the reaction mixture was added water at room temperature, and the mixture was extracted with chloroform. The solvent was evaporated under reduced pressure. The residue was purified by silica gel column chromatography (n-hexane:ethyl acetate=10:1-+1:1) to give the title compound (compound (I-26)) (306 mg, 69%) as a white waxy solid.

M.p. 57.4-57.8° C.;

$^{1}H$ NMR (500 MHz, $CDCl_3$) δ: 0.88 (t, 3H, J=6.7 Hz), 1.26-1.33 (m, 30H), 1.57 (qn, 6H, J=7.0 Hz), 3.38-3.46 (m, 6H), 3.56-3.59 (m, 4H), 3.62-3.65 (m, 16H), 5.97 (br s, 1H), 7.35 (dd, 1H, J=5.1, 2.9 Hz), 7.37 (dd, 1H, J=5.1, 1.4 Hz), 7.84 (dd, 1H, J=2.9, 1.4 Hz);

$^{13}C$ NMR (75 MHz, $CDCl_3$) δ: 14.1, 22.6, 26.01, 26.03, 26.9, 29.3 (2C), 29.40, 29.43, 29.45, 29.48 (2C), 29.51, 29.55, 29.56 (2C), 29.57, 29.7, 31.8, 39.8, 70.0 (2C), 70.5 (5C), 70.6 (3C), 71.48, 71.49, 126.0, 126.3, 127.8, 137.8, 163.0;

IR (ATR) $cm^{-1}$: 3334, 1623;

MS (FAB) m/z: 672 $[M+H]^+$;

HRMS (FAB) m/z: Calcd for $C_{37}H_{70}NO_7S$: 672.4873; found: 672.4879 $[M+H]^+$.

Example 27

Synthesis of N-(7,10,13,16,19,22-hexaoxadotriacontan-1-yl)thiophene-3-carboxamide (Compound (I-27)

raphy (n-hexane:ethyl acetate=1:1→ethyl acetate:methanol=10:1) to give 3,6,9,12,15-pentaoxa-1-pentacosanol (785 mg, 49%) as a clear pale-yellow oil. Under a nitrogen atmosphere, to a solution of 3,6,9,12,15-pentaoxa-1-pentacosanol (785 mg, 2.07 mmol) in dehydrated dimethylformamide (1.7 mL) were added, under ice-cooling, sodium hydride (manufactured by Tokyo Chemical Industry Co., Ltd.) (60% in oil, 166 mg, 4.15 mmol) and 15-crown-5 ether (manufactured by Tokyo Chemical Industry Co., Ltd.) (0.824 mL, 4.15 mmol), and the mixture was stirred at the same temperature for 10 min. To the reaction mixture was added a solution of 1-benzyloxy-6-bromohexane (compound (19a)) (846 mg, 3.12 mmol) obtained in Reference Example 7 in dehydrated dimethylformamide (5.2 mL) at the same temperature, and the mixture was stirred at room temperature for 24 hr. To the reaction mixture was added

I-27

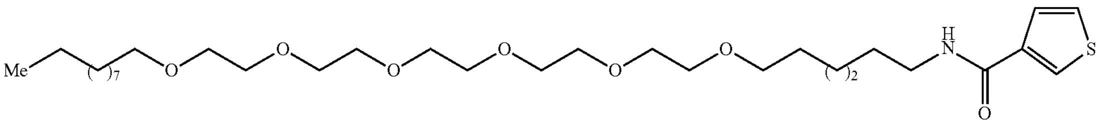

(27-1) Synthesis of 1-benzyloxy-7,10,13,16,19,22-hexaoxadotriacontane (Compound (18a))

water at room temperature, and the mixture was extracted with ethyl acetate. The organic layer was washed with saturated brine, and dried over anhydrous sodium sulfate. The solvent was evaporated under reduced pressure. The

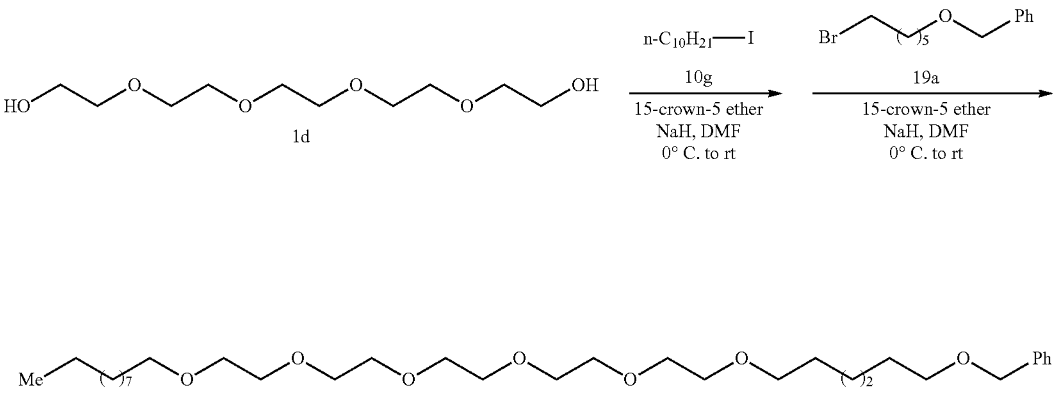

18a

Under a nitrogen atmosphere, to a solution of pentaethylene glycol (FUJIFILM Wako Pure Chemical Corporation) (compound (1d)) (0.885 mL, 4.20 mmol) in dehydrated dimethylformamide (4.2 mL) were added, under ice-cooling, sodium hydride (manufactured by Tokyo Chemical Industry Co., Ltd.) (60% in oil, 252 mg, 6.30 mmol) and 15-crown-5 ether (manufactured by Tokyo Chemical Industry Co., Ltd.) (1.25 mL, 6.30 mmol), and the mixture was stirred at the same temperature for 10 min. To the reaction mixture was added 1-iododecane (compound (10g)) (manufactured by Tokyo Chemical Industry Co., Ltd.) (1.34 mL, 6.30 mmol) at the same temperature, and the mixture was stirred at room temperature for 7 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane→n-hexane:ethyl acetate=2:1) to give 1-benzyloxy-7,10,13,16,19,22-hexaoxadotriacontane (compound (18a)) (705 mg, 61%) as a clear colorless oil.

$^{1}H$ NMR (500 MHz, $CDCl_3$) δ: 0.88 (3H, t, J=6.7 Hz), 1.25-1.43 (m, 18H), 1.52-1.66 (m, 6H), 3.44 (t, 4H, J=6.7 Hz), 3.45 (t, 2H, J=6.7 Hz), 3.55-3.58 (m, 4H), 3.61-3.65 (m, 16H), 4.49 (s, 2H), 7.23-7.37 (5H, m);

$^{13}C$ NMR (75 MHz, $CDCl_3$) δ: 14.0, 22.6, 25.9, 25.98, 26.00, 29.2, 29.4, 29.49 (2C), 29.52, 29.54, 29.6, 31.8, 70.0 (2C), 70.3, 70.50 (6C), 70.53 (2C), 71.3, 71.5, 72.8, 127.4, 127.5 (2C), 128.2 (2C), 138.6;

IR (ATR) $cm^{-1}$: No characteristic peak

MS (EI): m/z (%) 568 (3.8) $[M]^+$, 477 (2.0), 91 (100);

HRMS (EI): m/z Calcd for $C_{33}H_{60}O_7$: 568.4339; found: 568.4338 $[M]^+$.

(27-2) Synthesis of 7,10,13,16,19,22-hexaoxa-1-dotriacontanol (Compound (16b))

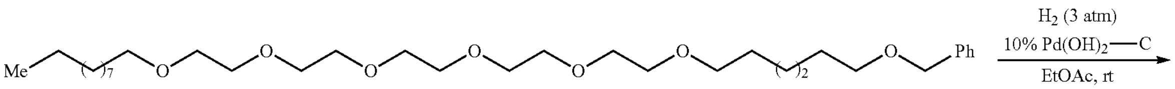

18a

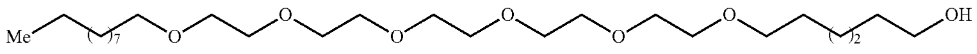

16b

To a solution of compound (18a) (614 mg, 1.08 mmol) in dehydrated ethyl acetate (10.8 mL) was added palladium hydroxide-activated carbon (FUJIFILM Wako Pure Chemical Corporation) (palladium 20%, containing water (about 50%), 61.4 mg) at room temperature, and the mixture was stirred under 3 atm hydrogen atmosphere at the same temperature for 3 hr. The mixture was filtered through celite, washed with ethyl acetate, and the solvent was evaporated under reduced pressure. The residue was purified by silica gel column chromatography (ethyl acetate) to give 7,10,13,16,19,22-hexaoxa-1-dotriacontanol (compound (16b)) (475 mg, 89%) as a clear colorless oil.

$^1H$ NMR (500 MHz, $CDCl_3$) δ: 0.84 (t, 3H, J=6.8 Hz), 1.22-1.36 (m, 18H), 1.49-1.58 (m, 6H), 1.80 (br s, 1H), 3.41 (t, 2H, J=6.6 Hz), 3.42 (t, 2H, J=6.6 Hz), 3.52-3.56 (m, 4H), 3.59-3.62 (m, 18H);

$^{13}C$ NMR (75 MHz, $CDCl_3$) δ: 14.0, 22.6, 25.5, 25.8, 26.0, 29.2, 29.38, 29.44, 29.46, 29.50, 29.51, 31.8, 32.6, 62.6, 69.9, 70.0, 70.48 (6C), 70.50 (2C), 71.2, 71.4;

IR (ATR) $cm^{-1}$: 3472;

MS (FAB) m/z: 479 $[M+H]^+$;

HRMS (FAB) m/z: Calcd for $C_{26}H_{55}O_7$: 479.3948; found: 479.3949 $[M+H]^+$.

(27-3) Synthesis of 7,10,13,16,19,22-hexaoxa-1-iododotriacontane (Compound (17b))

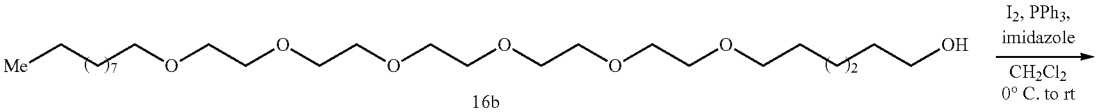

16b

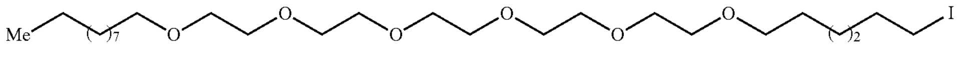

17b

Under a nitrogen atmosphere, to a solution of triphenylphosphine (278 mg, 1.06 mmol) in dehydrated dichloromethane (1.1 mL) were added, under ice-cooling, imidazole (72.1 mg, 1.06 mmol) and iodine (269 mg, 1.06 mmol), and the mixture was stirred at the same temperature for 1 hr. To the reaction mixture was added, under ice-cooling, a solution of compound (16b) (392 mg, 0.818 mmol) in dehydrated dichloromethane (3.0 mL), and the mixture was stirred at room temperature for 45 min. To the reaction mixture was added saturated aqueous sodium thiosulfate solution at room temperature, and the mixture was extracted with ethyl acetate. The organic layer was washed with saturated brine, and dried over anhydrous magnesium sulfate. The solvent was evaporated under reduced pressure, and the residue was purified by silica gel column chromatography (n-hexane:ethyl acetate=10:1) to give 7,10,13,16,19,22-hexaoxa-1-iododotriacontane (compound (17b)) (441 mg, 91%) as a clear pale-yellow oil.

$^1H$ NMR (500 MHz, $CDCl_3$) δ: 0.85 (t, 3H, J=6.7 Hz), 1.23-1.44 (m, 18H), 1.50-1.61 (m, 4H), 1.80 (qn, 2H, J=7.0 Hz), 3.16 (t, 2H, J=7.0 Hz), 3.42 (t, 2H, J=7.0 Hz), 3.43 (t, 2H, J=6.6 Hz), 3.53-3.57 (m, 4H), 3.60-3.63 (m, 16H);

$^{13}C$ NMR (75 Hz, $CDCl_3$) δ: 7.0, 14.1, 22.6, 25.0, 26.0, 29.3, 29.4, 29.49, 29.53 (2C), 29.6, 30.2, 31.8, 33.4, 69.97, 70.03, 70.5 (6C), 70.6 (2C), 71.1, 71.5;

IR (ATR) $cm^{-1}$: No characteristic peak

MS (FAB) m/z: 589 $[M+H]^+$;

HRMS (FAB) m/z: Calcd for $C_{26}H_{54}IO_6$: 589.2965; found: 589.2980 $[M+H]^+$.

(27-4) Synthesis of 1-azido-7,10,13,16,19,22-hexaoxadotriacontane (Compound (13i))

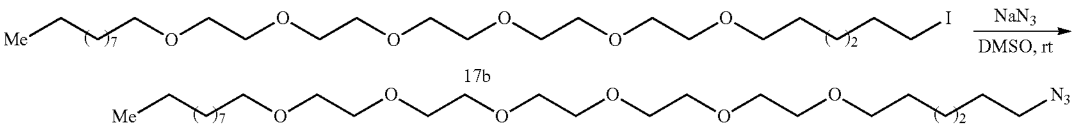

17b

13i

To a solution of compound (17b) (382 mg, 0.649 mmol) in dehydrated dimethyl sulfoxide (2.2 mL) was added sodium azide (85.7 mg, 1.30 mmol) at room temperature, and the mixture was stirred at room temperature for 2 hr. To the reaction mixture was added water at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (n-hexane:ethyl acetate=20:1-+10:1-+5:1-+1:1) to give 1-azido-7,10,13,16,19,22-hexaoxadotriacontane (compound (13i)) (308 mg, 94%) as a clear colorless oil.

$^1$H NMR (500 MHz, $CDCl_3$) δ: 0.85 (t, 3H, J=6.7 Hz), 1.23-1.38 (m, 18H), 1.50-1.62 (m, 6H), 3.23 (t, 2H, J=6.8 Hz), 3.42 (t, 2H, J=6.8 Hz), 3.43 (t, 2H, J=6.8 Hz), 3.53-3.56 (m, 4H), 3.60-3.63 (m, 16H);

$^{13}$C NMR (75 MHz, $CDCl_3$) δ: 14.0, 22.59, 25.61, 26.0, 26.5, 28.7, 29.24, 29.39, 29.41, 29.48, 29.52, 29.6, 31.8, 51.3, 69.96, 70.02, 70.5 (8C), 71.1, 71.5;

IR (ATR) $cm^{-1}$: 2092;

MS (FAB) m/z: 504 $[M+H]^+$;

HRMS (FAB) m/z: Calcd for $C_{26}H_{54}N_3O_6$: 504.4013; found: 504.4034 $[M+H]^+$.

(27-5) Synthesis of Compound (I-27)

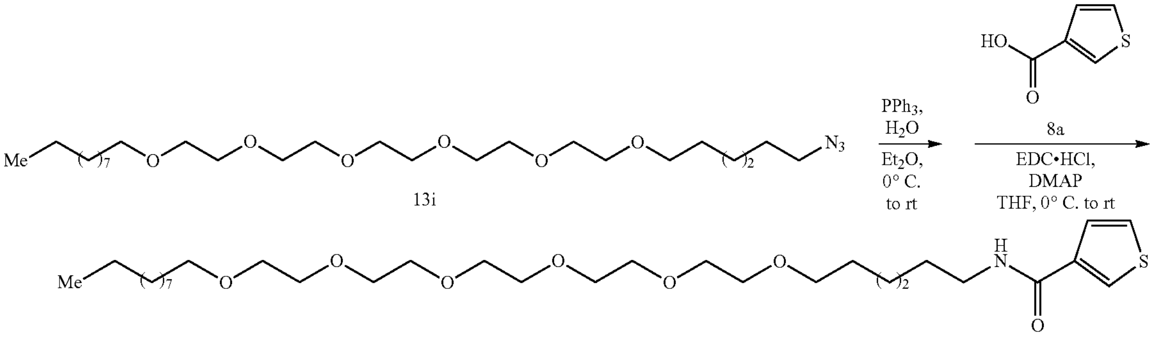

13i

I-27

To a mixed solution of compound (13i) (239 mg, 0.474 mmol) in diethyl ether/water (1:1, 4.7 mL) was added triphenylphosphine (249 mg, 0.950 mmol) at room temperature, and the mixture was stirred at the same temperature for 24 hr. To the reaction mixture was added 1M aqueous sodium hydroxide solution at room temperature, and the mixture was extracted with diethyl ether. The organic layer was dried over anhydrous sodium sulfate, and the solvent was evaporated under reduced pressure. Under a nitrogen atmosphere, to a solution of the residue in dehydrated tetrahydrofuran (9.4 mL) were added, under ice-cooling, 3-thiophenecarboxylic acid (compound (8a)) (manufactured by FUJIFILM Wako Pure Chemical Corporation) (181 mg, 1.41 mmol), 1-ethyl-3-(3-dimethylaminopropyl) carbodiimide hydrochloride (270 mg, 1.41 mmol) and N,N-dimethyl-4-aminopyridine (172 mg, 1.41 mmol), and the mixture was stirred at room temperature for 20 hr. To the reaction mixture was added water at room temperature, and the solvent was evaporated under reduced pressure. The mixture was extracted with chloroform, and the solvent was evaporated under reduced pressure. The residue was purified by silica gel column chromatography (n-hexane:chloroform=5:1→3:1→1:1-chloroform) to give N-(7,10,13,16,19,22-hexaoxadotriacontan-1-yl)thiophene-3-carboxamide (compound (I-27)) (205 mg, 74%) as a light brown waxy solid.

M.p. 40° C. or lower;

$^1$H NMR (500 MHz, $CDCl_3$) δ: 0.88 (t, 3H, J=6.7 Hz), 1.26-1.42 (m, 18H), 1.52-1.65 (m, 6H), 3.38-3.48 (m, 6H), 3.55-3.59 (m, 4H), 3.62-3.65 (m, 16H), 6.07 (br s, 1H), 7.33 (dd, 1H, J=5.1, 3.1 Hz), 7.39 (dd, 1H, J=5.1, 1.4 Hz), 7.86 (dd, 1H, J=3.1, 1.4 Hz);

$^{13}$C NMR (75 MHz, $CDCl_3$) δ: 14.1, 22.6, 25.7, 26.0, 26.6, 29.3, 29.37, 29.42, 29.50, 29.54 (2C), 29.6, 31.8, 39.6, 69.97, 69.99, 70.5 (6C), 70.6 (2C), 71.1, 71.5, 126.1, 126.2, 127.9, 137.7, 163.1;

IR (ATR) cml: 3329, 1622;

MS (FAB) m/z: 588 $[M+H]^+$;

HRMS (FAB) m/z: Calcd for $C_{31}H_{58}NO_7S$: 588.3934; found: 588.3925 $[M+H]^+$.

Experimental Example 1: Proliferation Suppressive Action on Murine Glioblastoma Stem Cells

Experimental Method

According to the method described in a literature (Tanigawa S, et al. Cancer Gene Therapy (2021). https://doi.org/10.1038/s41417-020-00282-5), murine glioblastoma stem cells were established, and cultured as neurosphere cells in a 5% $CO_2$ incubator at 37° C. using Neurobasal medium supplemented with B27 and N2 supplements (Gibco/Thermo Fisher Scientific, Waltham, MA, USA) and 10 ng/mL of EGF and bFGF (R&D Systems, Minneapolis, MN, USA). The neurospheres were made into a single cell suspension by Accutase (Innovative Cell Technologies, San Diego, CA, USA) treatment, $1\times10^5$ cells were seeded in a 6-well dish (Thermo Fisher Scientific, Waltham, MA, USA), and the compound of the present invention was diluted with culture medium to a final concentration of 100 nM and 500 nM, and allowed to act for 72 hr. Proliferation of these cells was evaluated using Trypan blue (FUJIFILM Wako Pure Chemical Corporation, Japan) staining method and counting the number of viable cells using a Countess II automatic cell counter (Thermo Fisher Scientific, Waltham, MA).

The compound of the present invention used in the experimental was dissolved at 2 mM using dimethyl sulfoxide (Nacalai Tesque, Kyoto, Japan) as a solvent.

Experimental Results

The evaluation results are shown in FIG. 1. From the results shown in FIG. 1, it was confirmed that the compound group of the present invention suppresses the proliferation of murine glioblastoma stem cells.

Experimental Example 2: Enhancement Effect of Temozolomide's Proliferation Suppressive Action on Human Glioblastoma Cells

Experimental Method

According to the method described in a literature (Matsumura K, et al. BMC Cancer (2016) 16(1):748.), human glioblastoma cell line U251 was cultured in a 5% $CO_2$ incubator at 37° C. using DMEM (FUJIFILM Wako Pure Chemical Corporation, Japan) supplemented with 10% bovine fetal serum (FBS, HyClone, GE Healthcare Life Sciences, Buckinghamshire, England) and 1% penicillin/streptomycin (FUJIFILM Wako Pure Chemical Corporation, respectively 100 units/mL, 100 μg/mL). Temozolomide (Sigma Chemical, St. Louis, MO, USA) which is used as a standard drug for the treatment of glioblastoma was dissolved at 200 mM using dimethyl sulfoxide (Nacalai Tesque, Kyoto, Japan) as a solvent. U251 cells were suspended in trypsin (Lonza, Walkersville, MD, USA), and $2.5\times10^3$ cells were seeded in a 6-well dish (Thermo Fisher Scientific, Waltham, MA, USA). After 24 hr, temozolomide diluted using a culture medium to final concentrations of 12.5, 25, and 50 μM, and the compound of the present invention (compound (I-5)) diluted with a culture medium to final concentrations of 25, 50, and 100 nM were allowed to act alone or in combination for 6 days. Proliferation of these cells was evaluated using Trypan blue (FUJIFILM Wako Pure Chemical Corporation, Japan) staining method and counting the number of viable cells using a Countess II automatic cell counter (Thermo Fisher Scientific, Waltham, MA). Combination index (CI) values of temozolomide and the compound of the present invention were calculated using CalcuSyn 2.11 software (Biosoft, Cambridge, UK), and Isobologram analysis was performed. The CI value of less than 0.9 was determined to be a synergistic effect, the CI value of 0.9 or more and less than 1.1 was determined to be an additive effect, and the CI value of 1.1 or more was determined to be an antagonistic effect.

Experimental Results

The evaluation results are shown in FIG. 2. From the results of FIG. 2, it was confirmed that the compound (I-5) of the present invention synergistically potentiates the proliferation suppressive ability of temozolomide against human glioblastoma U251 cells. In addition, the $ED_{50}$ value calculated from the number of viable cells of U251 after allowing the compound (I-5) of the present invention to act alone for 6 days was 43.1 nM.

Experimental Example 3: In Vivo Antitumor Effect in a Mouse Glioblastoma Transplantation Model

Experimental Method

According to the method described in a literature (Tanigawa S, et al. Cancer Gene Therapy (2021). https://doi.org/10.1038/s41417-020-00282-5), murine glioblastoma stem cells introduced with the Luciferase gene were established, and cultured as neurosphere cells in a 5% $CO_2$ incubator at 37° C. using Neurobasal medium supplemented with B27 and N2 supplements (Gibco/Thermo Fisher Scientific, Waltham, MA, USA) and 10 ng/mL of EGF and bFGF (R&D Systems, Minneapolis, MN, USA). The neurospheres were made into a single cell suspension by Accutase (Innovative Cell Technologies, San Diego, CA, USA) treatment, and $1\times10^3$ cells suspended in 2 μL of PBS were transplanted into the cerebrum of a 6-week-old male C57BL6J mouse (Oriental Bioservice, Kyoto, Japan) fixed on a Stereotaxic Instrument (51730D; Stoelting Co., Wood Dale, IL, USA) using a 30-gauge Hamilton syringe with autoinjector (Legato130; KD Scientific, Holliston, MA, USA). The compound of the present invention (compound (I-5)) dissolved in 10% dimethyl sulfoxide (Nacalai Tesque, Kyoto, Japan), 10% Cremophor EL (Sigma Chemical, St. Louis, MO, USA), and 80% saline (Nacalai Tesque, Kyoto, Japan) was intraperitoneally administered at a dose of 10 mg/kg three times a week from immediately after transplantation. Three weeks after cell transplantation, D-luciferin was administered intraperitoneally at a dose of 150 mg/kg and in vivo tumor size was evaluated using the IVIS Lumina XR imaging system (Summit Pharmaceuticals International, Tokyo, Japan).

Experimental Results

The evaluation results are shown in FIG. 3. From the results of FIG. 3, it was confirmed that the compound (I-5) of the present invention suppresses proliferation of glioblastoma transplanted tumor in vivo in mouse.

Experimental Example 4: Proliferation Suppressive Action on Human Colon Cancer SW48 Cells

Experimental Method

Human colon cancer SW48 cells were cultured in a 5% $CO_2$ incubator at 37° C. using DMEM (FUJIFILM Wako Pure Chemical Corporation, Japan) supplemented with 10% bovine fetal serum (FBS, HyClone, GE Healthcare Life Sciences, Buckinghamshire, England) and 1% penicillin/streptomycin (FUJIFILM Wako Pure Chemical Corporation, respectively 100 units/mL, 100 μg/mL). SW48 cells were suspended in trypsin (Lonza, Walkersville, MD, USA), and $1\times10^5$ cells were seeded in a 6-well dish (TPP, Trasadingen, Switzerland). After 24 hr, a group of the compounds of the present invention (compound (I-4), compound (I-5), and compound (I-10)) diluted with a culture medium to a final concentration of 500 nM was allowed to act for 3 days. Proliferation of these cells was evaluated using Trypan blue (FUJIFILM Wako Pure Chemical Corporation, Japan) staining method and counting the number of viable cells using a Countess II automatic cell counter (Thermo Fisher Scientific, Waltham, MA).

Experimental Results

The evaluation results are shown in FIG. 4. From the results of FIG. 4, it was confirmed that the compound group of the present invention suppresses proliferation of human colon cancer SW48 cells.

Experimental Example 5: AMP/ATP Ratio Increasing Action on Human Colon Cancer SW48 Cells Experimental Method Human colon cancer SW48 cells were cultured in a 5% $CO_2$ incubator at 37° C. using DMEM (FUJIFILM Wako Pure Chemical Corporation, Japan) supplemented with 10% bovine fetal serum (FBS, HyClone, GE Healthcare Life Sciences, Buckinghamshire, England) and 1% penicillin/streptomycin (FUJIFILM Wako Pure Chemical Corporation, respectively 100 units/mL, 100 μg/mL). SW48 cells were suspended in trypsin (Lonza, Walkersville, MD, USA), and $1\times10^5$ cells were seeded in a 6-well dish (TPP, Trasadingen, Switzerland). After 24 hr, the cells were treated with the compound of the present invention (compound (I-5)) diluted with a culture medium to final concentrations of 500 nM and 1 μM and allowed to act for 2 days. Intracellular AMP was measured with the AMP Glo assay kit (Promega, Madison, WI, USA), and intracellular ATP was measured with the Cell Titer Glo Luminescent Cell Viability Assay Kit (Promega, Madison, WI, USA) using a SYNERGY HT (BioTek Instruments, Inc. Winooski, VT, USA), and the AMP/ATP ratio was calculated.

Experimental Results

The evaluation results are shown in FIG. 5. From the results of FIG. 5, it was confirmed that the compound (I-5) of the present invention has action to increase the AMP/ATP ratio of human colon cancer SW48 cells.

Experimental Example 6: Phosphorylated AMPK Increasing Action on Human Colon Cancer SW48 Cells Experimental Method Human colon cancer SW48 cells were cultured in a 5% $CO_2$ incubator at 37° C. using DMEM (FUJIFILM Wako Pure Chemical Corporation, Japan) supplemented with 10% bovine fetal serum (FBS, HyClone, GE Healthcare Life Sciences, Buckinghamshire, England) and 1% penicillin/streptomycin (FUJIFILM Wako Pure Chemical Corporation, respectively 100 units/mL, 100 μg/mL). SW48 cells were suspended in trypsin (Lonza, Walkersville, MD, USA), and $1\times10^5$ cells were seeded in a 6-well dish (TPP, Trasadingen, Switzerland). After 24 hr, the cells were treated with the compounds of the present invention (compound (I-4), compound (I-5), and compound (I-10)) diluted with a culture medium to a final concentration of 100 nM and allowed to act for 2 days. Cellular proteins were dissolved in 1% SDS buffer supplemented with a protease inhibitor cocktail mix (Nacalai Tesque, Kyoto, Japan), and SDS-PAGE was performed. After transferring to PVDF membrane (Millipore, Billerica, MA, USA), Western blot analysis was performed using anti-phospho-AMPKα (Thr172, 1:1000, #2535; CST) antibody. GAPDH protein was analyzed as a loading control.

Experimental Results

The evaluation results are shown in FIG. 6. From the results of FIG. 6, it was confirmed that the compound group of the present invention has a phosphorylated AMPK increasing action on human colon cancer SW48 cells.

Experimental Example 7: In Vivo Antitumor Effect in a Human Colon Cancer SW48 Cell Transplantation Model Experimental Method According to the method described in a literature (Ii H, et al. ChemMedChem. (2018) 13(2):155-163), human colon cancer SW48 cells were cultured in a 5% $CO_2$ incubator at 37° C. using DMEM (FUJIFILM Wako Pure Chemical Corporation, Japan) supplemented with 10% bovine fetal serum (FBS, HyClone, GE Healthcare Life Sciences, Buckinghamshire, England) and 1% penicillin/streptomycin (FUJIFILM Wako Pure Chemical Corporation, respectively 100 units/mL, 100 μg/mL). SW48 cells were suspended in trypsin (Lonza, Walkersville, MD, USA), and $3\times10^6$ cells were suspended in 100 μL of PBS/Matrigel (1:1, Corning, Corning, NY, USA), and subcutaneously injected into 6-week-old male or female CB17 SCID mice (Japan Clea, Osaka, Japan) to create a subcutaneous transplantation tumor model. The compound of the present invention was dissolved in 10% ethanol (FUJIFILM Wako Pure Chemical Corporation, Japan), 10% dimethyl sulfoxide (Nacalai Tesque, Kyoto, Japan), 10% Cremophor EL (Sigma Chemical, St. Louis, MO, USA), and 70% saline (Nacalai Tesque, Kyoto, Japan), and administered intraperitoneally at a dose of 20 mg/kg every day from 4 days after transplantation. The major diameter and minor diameter were measured twice a week using calipers, and the tumor volume was calculated by 0.5× major diameter×minor diameter$^2$. 3.5 Weeks after cell transplantation, the tumor was removed and the weight was measured.

The compound of the present invention (compound (I-5)) used in the experiment was dissolved at 10 mg/mL in dimethyl sulfoxide/ethanol (1:1) as a solvent.

Experimental Results

The evaluation results are shown in FIGS. 7 (A), (B) and (C). From the results of FIG. 7, it was confirmed that the compound (I-5) of the present invention suppresses proliferation of human colon cancer SW48 transplanted tumors in the body of the mice. In addition, it was confirmed that no significant body weight change occurred when the compound of the present invention was administered daily at 20 mg/kg for 3.5 weeks.

Experimental Example 8: Proliferation Suppressive Effect on Human Lung Cancer A549 Cells Experimental Method According to the method described in a literature (Ii H, et al. ChemMedChem. (2018) 13(2):155-163), human lung cancer A549 cells were cultured in a 5% $CO_2$ incubator at 37° C. using DMEM (FUJIFILM Wako Pure Chemical Corporation, Japan) supplemented with 10% bovine fetal serum (FBS, HyClone, GE Healthcare Life Sciences, Buckinghamshire, England) and 1% penicillin/streptomycin (FUJIFILM Wako Pure Chemical Corporation, respectively 100 units/mL, 100 μg/mL). A549 cells were suspended in trypsin (Lonza, Walkersville, MD, USA), and $1\times10^3$ cells were seeded in a 96-well dish (TPP, Trasadingen, Switzerland). After 24 hr, they were treated with the compound of the present invention diluted in a culture medium to a final concentration of 500 nM and allowed to act for 3 days. WST-8 assay was performed using Cell Count Reagent SF (Nacalai Tesque, Kyoto, Japan) and absorbance at 450 nm was measured using SYNERGY HT (BioTek Instruments, Inc. Winooski, VT, USA), and cell proliferation was evaluated.

The compound of the present invention used in the test was dissolved at 2 mM using dimethyl sulfoxide (Nacalai Tesque, Kyoto, Japan) as a solvent.

Experimental Results

The evaluation results are shown in FIG. 8. From the results of FIG. 8, it was confirmed that the compound group of the present invention suppresses proliferation of human lung cancer A549 cells.

Experimental Example 9: Phosphorylated AMPK Increasing Action on Human Lung Cancer A549 Cells

Experimental Method

Human lung cancer A549 cells were cultured in a 5% $CO_2$ incubator at 37° C. using DMEM (FUJIFILM Wako Pure Chemical Corporation, Japan) supplemented with 10% bovine fetal serum (FBS, HyClone, GE Healthcare Life Sciences, Buckinghamshire, England) and 1% penicillin/streptomycin (FUJIFILM Wako Pure Chemical Corporation, respectively 100 units/mL, 100 μg/mL). A549 cells were suspended in trypsin (Lonza, Walkersville, MD, USA), and $1\times10^5$ cells were seeded in a 6-well dish (TPP, Trasadingen, Switzerland). After 24 hr, they were treated with the compound of the present invention diluted in a culture medium to final concentrations of 100 nM to 1 μM and allowed to act for 3 days. Cellular proteins were dissolved in 1% SDS buffer supplemented with a protease inhibitor cocktail mix (Nacalai Tesque, Kyoto, Japan), and SDS-PAGE was performed. After transferring to PVDF membrane (Millipore, Billerica, MA, USA), Western blot analysis was performed using anti-phospho-AMPKα (Thr172, 1:1000, #2535; CST) antibody. GAPDH protein was analyzed as a loading control.

Experimental Results

The evaluation results are shown in FIG. 9. From the results of FIG. 9, it was confirmed that the compound group of the present invention has a phosphorylated AMPK increasing action on human lung cancer A549 cells.

Formulation Example 1: Production of Capsule

| | |
|---|---|
| 1) compound (I-5) | 50 mg |
| 2) microcrystalline cellulose | 10 mg |

-continued

| | |
|---|---|
| 3) lactose | 19 mg |
| 4) magnesium stearate | 1 mg |

1), 2), 3), and 4) are mixed and filled in a gelatin capsule.

Formulation Example 2: Production of Tablet

| | |
|---|---|
| 1) compound (I-5) | 50 g |
| 2) lactose | 50 g |
| 3) cornstarch | 15 g |
| 4) carmellose calcium | 44 g |
| 5) magnesium stearate | 1 g |

The total amount of 1), 2), and 3), and 30 g of 4) are kneaded with water, vacuum dried, and sieved. The sieved powder is mixed with 4) (14 g) and 5) (1 g), and the mixture is punched by a tableting machine, whereby 1000 tablets containing 50 mg of compound (I-5) per tablet are obtained.

INDUSTRIAL APPLICABILITY

The compound of the present invention shows a superior AMP-activated protein kinase activating action. Hence, the medicaments (pharmaceutical compositions) containing the compound of the present invention are useful for the prophylaxis and/or treatment of the diseases caused by decreased activity of AMP-activated protein kinase (e.g., diabetes, obesity, cancer, etc.). Particularly, they can be superior agents for the prophylaxis and/or treatment of solid tumors such as glioblastoma, gastric cancer, colon cancer, lung cancer, breast cancer, germ cell cancer, liver cancer, skin cancer, bladder cancer, prostate cancer, uterine cancer, cervical cancer, ovarian cancer and the like. In addition, the compound of the present invention has advantages in that it is easy to synthesize, stable, and easy to handle.

This application is based on a patent application No. 2021-094481 filed in Japan (filing date: Jun. 4, 2021), the contents of which are incorporated in full herein.

The invention claimed is:

1. A compound represented by the formula (I):

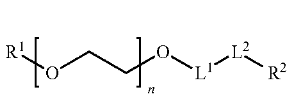

(I)

wherein $R^1$ is a propyl group or a $C_{8-10}$ alkyl group, each of which is optionally substituted by a hydroxy group or a $C_{2-6}$ alkynyl group;

$R^2$ is a thienyl group or a pyrazolyl group, each of which is optionally substituted by a substituent selected from the group consisting of a halogen atom, an optionally substituted $C_{1-6}$ alkyl group, an optionally substituted $C_{6-10}$ aryl group, a cyano group, a nitro group, a carboxy group, a $C_{1-6}$ alkoxy-carbonyl group, and an acyl group, $L^1$ is a $C_{1-20}$ alkylene group optionally substituted by a hydroxy group, $L^2$ is a divalent group represented by the formula:

*NHC(═O)**

or the formula:

*NHS(O)$_2$** wherein * represents a bonding position to $L^1$; and ** represents a bonding position to $R^2$; and n is an integer of 1 to 8, or a pharmaceutically acceptable salt thereof, or a hydrate thereof.

2. The compound according to claim 1, wherein $R^1$ is a $C_{8-10}$ alkyl group optionally substituted by a hydroxy group or an ethynyl group, $R^2$ is a 2-thienyl group, a 3-thienyl group, or a 5-pyrazolyl group, each of which is optionally substituted by a substituent selected from the group consisting of a halogen atom, a $C_{1-6}$ alkyl group, a cyano group, a nitro group, a carboxy group, and a $C_{1-6}$ alkoxy-carbonyl group, $L^1$ is a $C_{6-12}$ alkylene group, and n is an integer of 1 to 6, or a pharmaceutically acceptable salt thereof, or a hydrate thereof.

3. The compound according to claim 1, wherein the compound of the formula (I) is any of the following a to k, or a pharmaceutically acceptable salt thereof:

a. N-(13,16,19,22-tetraoxapentacosan-1-yl)thiophene-3-carboxamide, b. N-(13,16,19,22-tetraoxahentriacontan-1-yl)thiophene-3-carboxamide, c. N-(13,16,19,22-tetraoxadotriacontan-1-yl)thiophene-3-carboxamide, d. N-(13,16,19,22-tetraoxa-33-tetratriacontyn-1-yl)thiophene-3-carboxamide, e. N-(13,16,19,22-tetraoxa-32-tritriacontyn-1-yl)thiophene-3-carboxamide, f. N-(13,16,19,22,25-pentaoxadotriacontan-1-yl)thiophene-3-carboxamide, g. N-(10,13,16,19,22-pentaoxadotriacontan-1-yl)thiophene-3-carboxamide, h. N-(13,16,19,22-tetraoxadotriacontan-1-yl)-1-methylpyrazole-5-carboxamide, i. N-(13,16,19,22-tetraoxadotriacontan-1-yl)thiophene-2-carboxamide, j. N-(13,16,19,22,25-pentaoxapentatriacontan-1-yl)thiophene-3-carboxamide, and k. N-(13,16,19,22,25,28-hexaoxaoctatriacontan-1-yl)thiophene-3-carboxamide.

4. A pharmaceutical composition comprising (a) the compound according to claim 1, or a pharmaceutically acceptable salt thereof, or a hydrate thereof as an active ingredient, and (b) a pharmaceutically acceptable carrier.

5. A pharmaceutical composition comprising (a) the compound according to claim 2, or a pharmaceutically acceptable salt thereof, or a hydrate thereof as an active ingredient, and (b) a pharmaceutically acceptable carrier.

6. A method of treating a disease caused by decreased activity of AMP-activated protein kinase in a subject, comprising administering an effective amount of the compound according to claim 1, or a pharmaceutically acceptable salt thereof, or a hydrate thereof, as an active ingredient to the subject.

7. A method of treating a disease caused by decreased activity of AMP-activated protein kinase in a subject, comprising administering an effective amount of the compound according to claim 2, or a pharmaceutically acceptable salt thereof, or a hydrate thereof, as an active ingredient to the subject.

8. The method of claim 6, wherein the disease caused by decreased activity of AMP-activated protein kinase is diabetes, obesity, or cancer.

9. The method of claim 7, wherein the disease caused by decreased activity of AMP-activated protein kinase is diabetes, obesity, or cancer.

10. The method of claim 6, wherein the disease caused by decreased activity of AMP-activated protein kinase is cancer.

11. The method of claim 7, wherein the disease caused by decreased activity of AMP-activated protein kinase is cancer.

* * * * *